(12) United States Patent
Sakai et al.

(10) Patent No.: US 9,957,260 B2
(45) Date of Patent: May 1, 2018

(54) ORGANIC METAL COMPLEX, LIGHT EMITTING MATERIAL, DELAYED FLUORESCENT MATERIAL, AND ORGANIC LIGHT EMITTING DEVICE

(71) Applicants: KYUSHU UNIVERSITY, NATIONAL UNIVERSITY CORPORATION, Fukuoka-shi, Fukuoka (JP); NIPPON STEEL & SUMIKIN CHEMICAL CO., LTD., Tokyo (JP); DYDEN CO, Kurume-shi, Fukuoka (JP)

(72) Inventors: Yumi Sakai, Kurume (JP); Hiroshi Miyazaki, Kitakyushu (JP); Chihaya Adachi, Fukuoka (JP); Naoto Noutsuka, Fukuoka (JP)

(73) Assignees: KYUSHU UNIVERSITY, NATIONAL UNIVERSITY CORPORATION, Fukuoka (JP); NIPPON STEEL & SUMIKIN CHEMICAL CO., LTD., Tokyo (JP); DYDEN CO., Fukuoka (JP)

(*) Notice: Subject to any disclaimer, the term of this patent is extended or adjusted under 35 U.S.C. 154(b) by 123 days.

(21) Appl. No.: 14/910,791

(22) PCT Filed: Jun. 23, 2014

(86) PCT No.: PCT/JP2014/066502
§ 371 (c)(1),
(2) Date: Feb. 8, 2016

(87) PCT Pub. No.: WO2015/019725
PCT Pub. Date: Feb. 12, 2015

(65) Prior Publication Data
US 2016/0185765 A1    Jun. 30, 2016

(30) Foreign Application Priority Data

Aug. 9, 2013  (JP) .................................. 2013-166915
Mar. 27, 2014 (JP) .................................. 2014-065283

(51) Int. Cl.
*C07D 413/10*    (2006.01)
*H01L 51/00*    (2006.01)
(Continued)

(52) U.S. Cl.
CPC ......... *C07D 413/10* (2013.01); *C07D 401/10* (2013.01); *C07D 403/10* (2013.01);
(Continued)

(58) Field of Classification Search
None
See application file for complete search history.

(56) References Cited

U.S. PATENT DOCUMENTS 5,779,937 A    7/1998    Sano et al.
6,358,633 B1   3/2002    Sano et al.
(Continued)

FOREIGN PATENT DOCUMENTS

CN    101481613 A    7/2009
CN    101654442 A    2/2010
(Continued)

OTHER PUBLICATIONS

Sakai et al., Chem. Commun., 2015, 51, 3181.*
(Continued)

*Primary Examiner* — Vu A Nguyen
(74) *Attorney, Agent, or Firm* — Browdy and Neimark, PLLC

(57) ABSTRACT

An organic metal complex represented by the following general formula is useful as a light emitting material for an
(Continued)

organic electroluminescent device and others. X represents O, S or —N($R^7$)—; Y represents O, S or —N(—$SO_2$—$R^8$)—; $R^1$ to $R^8$ represent H, an alkyl group or an aryl group; at least one of $Z^1$ and $Z^2$ represents a phenoxazin-10-yl group, a phenothiazin-10-yl group, a phenazin-10-yl group, etc.; M represents an element of the group 1 except for hydrogen, the group 2, the group 11, the group 12, or the group 13 of the periodic table; L represents a ligand; n is 1 to 3; and m is 0 to 2:

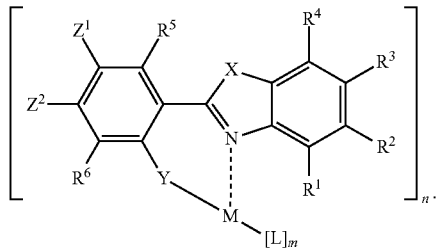

14 Claims, 18 Drawing Sheets

(51) Int. Cl.

| | |
|---|---|
| C09K 11/06 | (2006.01) |
| C07D 417/10 | (2006.01) |
| C07D 401/10 | (2006.01) |
| C07D 403/10 | (2006.01) |
| C07F 5/06 | (2006.01) |
| C09B 17/00 | (2006.01) |
| C09B 19/00 | (2006.01) |
| C09B 21/00 | (2006.01) |
| C09B 57/10 | (2006.01) |
| C09B 69/00 | (2006.01) |
| H01L 51/50 | (2006.01) |

(52) U.S. Cl.
CPC ............ *C07D 417/10* (2013.01); *C07F 5/069* (2013.01); *C09B 17/00* (2013.01); *C09B 19/00* (2013.01); *C09B 21/00* (2013.01); *C09B 57/10* (2013.01); *C09B 69/008* (2013.01); *C09K 11/06* (2013.01); *H01L 51/0059* (2013.01); *H01L 51/0077* (2013.01); *H01L 51/0081* (2013.01); *H01L 51/0092* (2013.01); *C09K 2211/1029* (2013.01); *C09K 2211/1033* (2013.01); *C09K 2211/1037* (2013.01); *C09K 2211/1044* (2013.01); *C09K 2211/1096* (2013.01); *C09K 2211/181* (2013.01); *C09K 2211/186* (2013.01); *C09K 2211/188* (2013.01); *H01L 51/5012* (2013.01); *H01L 51/5016* (2013.01)

(56) References Cited

U.S. PATENT DOCUMENTS

| | | | |
|---|---|---|---|
| 2005/0006625 | A1 | 1/2005 | Heinz-Werner et al. |
| 2010/0046704 | A1 | 2/2010 | Song et al. |
| 2010/0051106 | A1 | 5/2010 | Kim et al. |

FOREIGN PATENT DOCUMENTS

| | | |
|---|---|---|
| CN | 101891895 | 11/2010 |
| JP | 2000100569 A | 4/2000 |
| JP | 2000355687 A | 12/2000 |
| JP | 06336586 A1 | 1/2005 |
| JP | 200511610 A | 1/2005 |
| JP | 2005154396 A | 6/2005 |
| JP | 2007203040 A | 8/2007 |
| JP | 2008515466 A | 5/2008 |
| JP | 4278186 B2 | 6/2009 |
| JP | 09279136 A | 12/2009 |
| JP | 201059144 | 3/2010 |
| JP | 2010060572 A | 3/2010 |
| JP | 2010230532 A | 10/2010 |
| JP | 2010230676 A | 10/2010 |
| JP | 2013546040 A | 12/2013 |
| JP | 2014064957 A | 4/2014 |
| JP | 2014508954 A | 4/2014 |
| KR | 1020110061920 A | 6/2011 |
| WO | 9851757 A1 | 11/1998 |
| WO | 2004081019 A1 | 9/2004 |

OTHER PUBLICATIONS

Office action with machine translation from corresponding Chinese application No. 201480044013.7, dated May 10, 2017.
International Search Report, dated Aug. 26, 2014, in corresponding application No. PCT/JP2014/066502.
Santra, Mithun et al, "Dramatic Substituent Effects on the Photoluminescence of Baron Complexes of 2-(Benzothiazol-2-yl)phenols" A European Journal, 18 ( 32) 9886-9893 (2012).
Li, Di et al, "Construction of full-color-tunable and strongly emissive materials by functionalizing a boron-chelate four-ring-fused-conjugated core" Journal of Materials Chemistry, 22 (10) 4319-4328 (2012).
Megherbi, et al "Fully Automatic 3D Threat Image Projection: Application to Densely Cluttered 3D Computed Tomography Baggage Images" Image Processing Theory, Tools and Applications. 1-7 (2012).
Yildiz et al "3-D Threat Image Projection" Three-Dimensional Image Capture and Application. XP002625062 1-8 (2008).
Rusu et al "Close-range Scene Segmentation and Reconstruction of 3D Point Cloud Maps for Mobile Manipulation in Domestic Environments" International Conference on Intelligent Robots and Systems. 1-6 (2009).
Partial European Search Report, dated Nov. 20, 2015 in corresponding application No. 15173714.5.
European Search report for European Application No. 14834011.0 dated Mar. 1, 2017.
International Preliminary Report on Patentability, dated Feb. 18, 2016. In corresponding application No. PCT/JP2014/066502.

* cited by examiner

ORGANIC METAL COMPLEX, LIGHT EMITTING MATERIAL, DELAYED FLUORESCENT MATERIAL, AND ORGANIC LIGHT EMITTING DEVICE

TECHNICAL FIELD

The present invention relates to an organic metal complex that is useful as a light emitting material, and an organic light emitting device using the same.

BACKGROUND ART

An organic light emitting device, such as an organic electroluminescent device (organic EL device), has been actively studied for enhancing the light emission efficiency thereof. In particular, various studies for enhancing the light emission efficiency have been made by newly developing and combining an electron transporting material, a hole transporting material, a light emitting material and the like constituting an organic electroluminescent device. There are studies relating to an organic electroluminescent device utilizing an organic metal complex having a heterocyclic compound as a ligand.

Patent Documents 1 and 2 describe the use of the chelate compound represented by the following general formula as a light emitting material or a host material of a light emitting layer. In the following general formula, each of X and Z represents any one element selected from C, S, Se, Te, N, and P, Y represents any one element selected from C, N, and P, A1 represents a group of an aromatic compound or a heterocyclic compound having a hydroxyl group bonded to the ortho-position with respect to the atom represented by Y, and A2 constitutes an aromatic compound or a heterocyclic compound by bonding to the carbon atoms bonded to X and Z, provided that A1 and A2 may have a substituent.

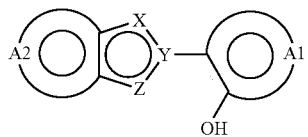

Patent Document 3 describes an example of the use of the oxazole metal complex represented by the following general formula as a material of an organic light emitting layer. In the following general formula, $R^1$ to $R^8$ each independently represent a hydrogen atom, a halogen atom, an alkyl group, an aralkyl group, an alkenyl group, an aryl group, a cyano group, an amino group, an amide group, an alkoxycarbonyl group, a carboxyl group, an alkoxy group, an aromatic hydrocarbon group, which may have a substituent, or an aromatic heterocyclic group, which may have a substituent, M represents beryllium, zinc, cadmium, aluminum, gallium, indium, scandium, yttrium, magnesium, calcium, strontium, cobalt, copper, or nickel, and n represents an integer of from 1 to 3.

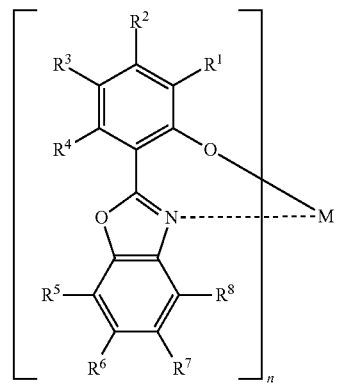

Patent Documents 4 and 5 describes the use of a metal complex having the same skeleton as the oxazole skeleton described in Patent Document 3 as a light emitting material of a host material of a light emitting layer, and Patent Documents 6 and 7 describe the use of the metal complex having phenylbenzoxazole as a ligand as a host material of a light emitting layer.

CITATION LIST

Patent Literatures

Patent Document 1: JP-A-9-279136
Patent Document 2: U.S. Pat. No. 5,779,937
Patent Document 3: JP-A-6-336586
Patent Document 4: JP-A-2000-100569
Patent Document 5: JP-A-2005-11610
Patent Document 6: Japanese Patent No. 4,278186
Patent Document 7: WO 98/51757

SUMMARY OF INVENTION

Technical Problem

However, the organic metal complexes described in the aforementioned patent literatures are not sufficiently satisfactory in the light emission characteristics. Under the circumstances, the present inventors have made earnest investigations for an object of providing a general formula of an organic metal complex that is useful as a light emitting material, and generalizing a structure of an organic light emitting device that has a higher light emission efficiency.

Solution to Problem

The inventors have thought that in the organic metal complexes described in the literatures, the ligand functions mainly as an acceptor, and the reason why the light emission characteristics cannot be sufficiently improved is the shortage of the donor property, and have found that the light emission characteristics of the organic metal complexes are remarkably improved by introducing a heterocyclic group having a donor property to a ligand having an oxazole skeleton or an analogous skeleton thereof. Furthermore, the inventors have found that the group of organic metal complexes includes ones that is useful as a delayed fluorescent material, and have clarified that an organic light emitting device having a high light emission efficiency may be provided inexpensively. Based on the knowledge, the inventors have thus achieved the invention described below as a measure for solving the problems.

(1) An organic metal complex represented by the following general formula (1):

General Formula (1)

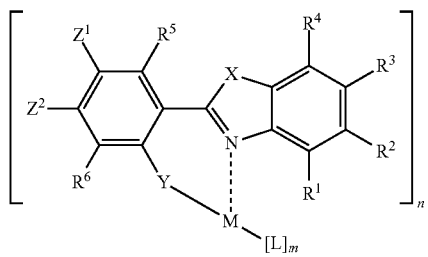

wherein in the general formula (1), X represents an oxygen atom, a sulfur atom, or —N($R^7$)—; Y represents an oxygen atom, a sulfur atom, or —N(—$SO_2$—$R^8$)—; $R^1$ to $R^8$ each independently represent a hydrogen atom, a substituted or unsubstituted alkyl group, or a substituted or unsubstituted aryl group; $Z^1$ and $Z^2$ each independently represent a hydrogen atom, a substituted or unsubstituted alkyl group, a substituted or unsubstituted aryl group, or a group represented by any of the following general formulae (A) to (E), provided that at least one of $Z^1$ and $Z^2$ represents a group represented by any of the following general formulae (A) to (E); M represents an element of the group 1 except for hydrogen, the group 2, the group 11, the group 12, or the group 13 of the periodic table; L represents a ligand of M that is not encompassed by the general formula of the ligand shown above M; n represents an integer of from 1 to 3; and m represents an integer of from 0 to 2:

General Formula (A)

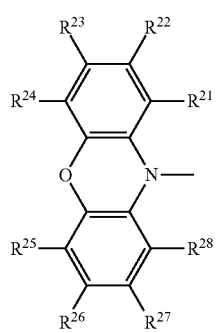

General Formula (B)

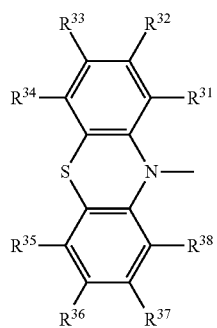

General Formula (C)

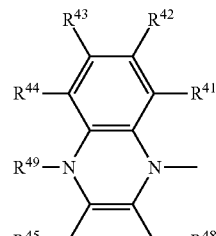

General Formula (D)

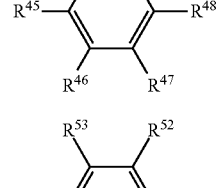

General Formula (E)

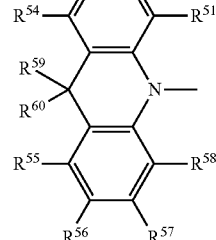

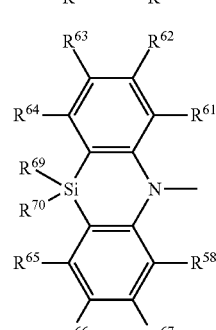

wherein in the general formulae (A) to (E), $R^{21}$ to $R^{28}$, $R^{31}$ to $R^{38}$, $R^{41}$ to $R^{49}$, and $R^{51}$ to $R^{70}$ each independently represent a hydrogen atom or a substituent, provided that $R^{21}$ and $R^{22}$, $R^{22}$ and $R^{23}$, $R^{23}$ and $R^{24}$, $R^{25}$ and $R^{26}$, $R^{26}$ and $R^{27}$, $R^{27}$ and $R^2$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{59}$ and $R^{60}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, and $R^{69}$ and $R^{70}$ each may be bonded to each other to form a cyclic structure.

(2) The organic metal complex according to the item (1), wherein in the general formula (1), $Z^2$ represents a group represented by any of the general formulae (A) to (E).

(3) The organic metal complex according to the item (1), wherein in the general formula (1), $Z^1$ represents a group represented by any of the general formulae (A) to (E).

(4) The organic metal complex according to any one of the items (1) to (3), wherein in the general formula (1), $Z^1$ or $Z^2$ represents a group represented by the general formula (A) or the general formula (B).

(5) The organic metal complex according to any one of the items (1) to (4), wherein in the general formula (1), M represents Zn or Li.

(6) The organic metal complex according to any one of the items (1) to (5), wherein in the general formula (1), Y represents an oxygen atom.

(7) The organic metal complex according to any one of the items (1) to (6), wherein in the general formula (1), m represents 1 or 2.

(8) The organic metal complex according to the item (7), wherein L represents a substituted or unsubstituted aryloxy ligand.

(9) The organic metal complex according to the item (8), wherein L represents an aryloxy ligand substituted with a substituted or unsubstituted diarylamino group.

(10) An organic metal complex satisfying the following expressions (I) and (II):

$$S_C - T_C \leq 0.2 \text{ eV} \quad \text{Expression (I)}$$

$$S_L - T_L \leq 0.2 \text{ eV} \quad \text{Expression (II)}$$

wherein in the expressions (I) and (II), $S_C$ represents energy of a singlet excited state of the organic metal complex; $T_C$ represents energy of a triplet excited state of the organic metal complex; $S_L$ represents energy of a singlet excited state of a ligand constituting the organic metal complex; and $T_L$ represents energy of a triplet excited state of a ligand constituting the organic metal complex.

(11) A light emitting material containing the organic metal complex according to any one of the items (1) to (10).

(12) A delayed fluorescent material containing the organic metal complex according to any one of the items (1) to (10).

(13) An organic light emitting device containing the light emitting material according to the item (11).

(14) The organic light emitting device according to the item (13), wherein the organic light emitting device emits delayed fluorescent light.

(15) The organic light emitting device according to the item (13) or (14), wherein the organic light emitting device is an organic electroluminescent device.

Advantageous Effects of Invention

The organic metal complex of the invention is useful as a light emitting material. The organic metal complex of the invention includes one that emits delayed fluorescent light. The organic light emitting device using the organic metal complex of the invention as a light emitting material is capable of achieving a high light emission efficiency.

DESCRIPTION OF EMBODIMENTS

Figure 1:
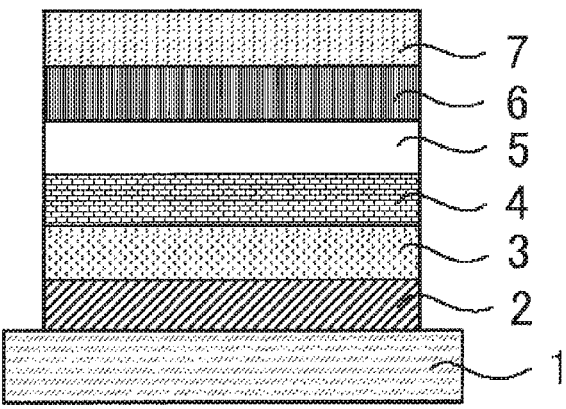
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the molecule of the compound used in the invention is not particularly limited in isotope species, and for example, all the hydrogen atoms in the molecule may be $^1$H, and all or a part of them may be $^2$H (deuterium (D)).

Organic Metal Complex
Organic Metal Complex Represented by General Formula (1)

In the organic metal complex represented by the general formula (1), as described later, it is considered that an interlevel transition of an exciton frequently occurs within the ligand due to the presence of the group represented by any of the general formulae (A) to (E) at the 4-position ($Z^2$) or the 5-position ($Z^1$) of the heterocyclic compound as the ligand. According thereto, the organic metal complex may provide a high light emission efficiency. The organic metal complex represented by the general formula (1) will be described in detail below.

The organic metal complex represented by the general formula (1) is a novel compound. The organic metal complex has a heterocyclic compound as a ligand and a center metal M.

General Formula (1)

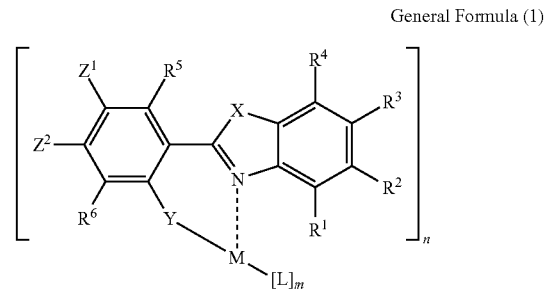

In the general formula (1), X represents an oxygen atom, a sulfur atom, or —N($R^7$)—. $R^7$ represents a hydrogen atom, a substituted or unsubstituted alkyl group, or a substituted or unsubstituted aryl group. For example, the organic metal complex, in which X is an oxygen atom, is preferably used.

The alkyl group that is capable of being used as $R^7$ may be linear, branched, or cyclic. A linear or branched alkyl group is preferred. The alkyl group preferably has from 1 to 20 carbon atoms, more preferably from 1 to 12 carbon atoms, further preferably from 1 to 6 carbon atoms, and still further preferably from 1 to 3 carbon atoms (i.e., a methyl group, an ethyl group, a n-propyl group, and an isopropyl group are still further preferred). Examples of the cyclic alkyl group include a cyclopentyl group, a cyclohexyl group, and a cycloheptyl group.

The aryl group that is capable of being used as $R^7$ may contain only one aromatic ring, or may have a structure containing two or more aromatic rings fused to each other. The aryl group preferably has from 6 to 22 carbon atoms, more preferably from 6 to 18 carbon atoms, further preferably from 6 to 14 carbon atoms, and still further preferably from 6 to 10 carbon atoms (i.e., a phenyl group, a 1-naphthyl group, and a 2-naphthyl group are still further preferred).

The alkyl group may be further substituted or may not be substituted. Examples of the substituent in the case where the alkyl group is substituted include an alkoxy group, an aryl group, and an aryloxy group, and for the descriptions and the preferred ranges of the aryl group as the substituent, reference may be made to the descriptions for the aforementioned aryl group.

The aryl group may be further substituted or may not be substituted. Examples of the substituent in the case where the aryl group is substituted include an alkyl group, an alkoxy group, an aryl group, and an aryloxy group, and for the descriptions and the preferred ranges of the alkyl group and the aryl group, reference may be made to the descriptions for the aforementioned alkyl group and the aforementioned aryl group.

The alkoxy group that is capable of being used as the substituent may be linear, branched, or cyclic. A linear or branched alkoxy group is preferred. The alkoxy group preferably has from 1 to 20 carbon atoms, more preferably from 1 to 12 carbon atoms, further preferably from 1 to 6 carbon atoms, and still further preferably from 1 to 3 carbon atoms (i.e., a methoxy group, an ethoxy group, a n-propoxy group, and an isopropoxy group are still further preferred). Examples of the cyclic alkoxy group include a cyclopentyloxy group, a cyclohexyloxy group, and a cycloheptyloxy group.

The aryloxy group that is capable of being used as the substituent may contain only one aromatic ring, or may have a structure containing two or more aromatic rings fused to each other. The aryloxy group preferably has from 6 to 22 carbon atoms, more preferably from 6 to 18 carbon atoms, further preferably from 6 to 14 carbon atoms, and still further preferably from 6 to 10 carbon atoms (i.e., a phenoxy group, a 1-naphthyloxy group, and a 2-naphthyloxy group are still further preferred).

Preferred examples of the group that is capable of being used as $R^7$ include an alkyl group having from 1 to 6 carbon atoms, an aralkyl group having from 7 to 15 carbon atoms, and an aryl group having from 6 to 14 carbon atoms, among the substituted or unsubstituted alkyl groups and the substituted or unsubstituted aryl group exemplified above.

Y represents an oxygen atom, a sulfur atom, or —N($-SO_2-R^8$)—. $R^8$ represents a hydrogen atom, a substituted or unsubstituted alkyl group, or a substituted or unsubstituted aryl group. For the substituted or unsubstituted alkyl group and the substituted or unsubstituted aryl group that are capable of being used as $R^8$, reference may be made to the descriptions and the preferred ranges of the substituted or unsubstituted alkyl group and the substituted or unsubstituted aryl group that are capable of being used as $R^7$. For example, the organic metal complex, in which Y is an oxygen atom, is preferably used.

$R^1$ to $R^6$ each independently represent a hydrogen atom, a substituted or unsubstituted alkyl group, or a substituted or unsubstituted aryl group. For the substituted or unsubstituted alkyl group and the substituted or unsubstituted aryl group that are capable of being used as $R^1$ to $R^6$, reference may be made to the descriptions and the preferred ranges of the substituted or unsubstituted alkyl group and the substituted or unsubstituted aryl group that are capable of being used as $R^7$.

$Z^1$ and $Z^2$ each independently represent a hydrogen atom, a substituted or unsubstituted alkyl group, a substituted or unsubstituted aryl group, or a group represented by any of the following general formulae (A) to (E), provided that at least one of $Z^1$ and $Z^2$ represents a group represented by any of the following general formulae (A) to (E). For the substituted or unsubstituted alkyl group and the substituted or unsubstituted aryl group that are capable of being used as $Z^1$ and $Z^2$, reference may be made to the descriptions and the preferred ranges of the substituted or unsubstituted alkyl group and the substituted or unsubstituted aryl group that are capable of being used as $R^7$. $R^1$ to $R^6$, $R^7$, $R^8$, $Z^1$, and $Z^2$ may be the same as or different from each other.

The group represented by any of the following general formulae (A) to (E) is a heterocyclic group having a donor property. Accordingly, in the organic metal complex that has the group as a ligand, it is considered that an interlevel transition of an exciton frequently occurs within the ligand, and thereby the organic metal complex may provide a high light emission efficiency. The group represented by any of the following general formulae (A) to (E) may be any of $Z^1$ (i.e., the 5-position) and $Z^2$ (i.e., the 4-position), and is preferably $Z^2$.

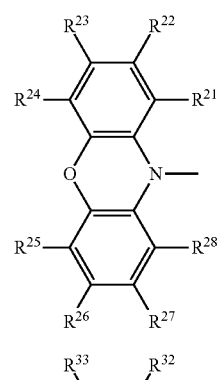

General Formula (A)

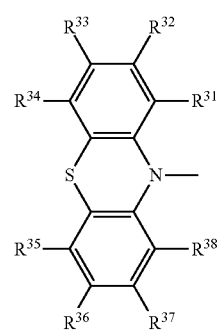

General Formula (B)

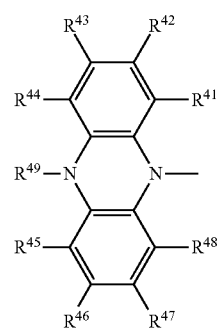

General Formula (C)

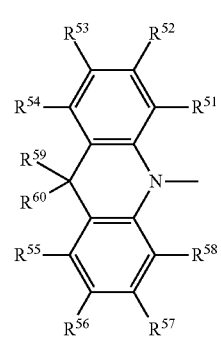

General Formula (D)

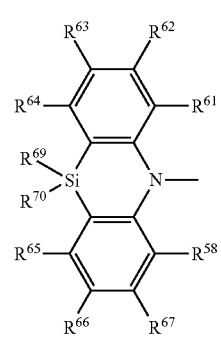

General Formula (E)

In the general formulae (A) to (E), $R^{21}$ to $R^{28}$, $R^{31}$ to $R^{38}$, $R^{41}$ to $R^{49}$, and $R^{51}$ to $R^{70}$ each independently represent a hydrogen atom or a substituent.

Examples of the substituent that is capable of being used as $R^{21}$ to $R^{28}$, $R^{31}$ to $R^{38}$, $R^{41}$ to $R^{49}$, and $R^{51}$ to $R^{70}$ include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

The number of the substituent in the general formulae (A) to (E) is not particularly limited, and all $R^{21}$ to $R^{28}$, $R^{31}$ to $R^{38}$, $R^{41}$ to $R^{49}$, and $R^{51}$ to $R^{70}$ may be unsubstituted (i.e., hydrogen atoms). In the case where there are two or more substituents in the general formulae (A) to (E), the substituents may be the same as or different from each other. In the case where the general formulae (A) to (E) have a substituent, the substituent is preferably any of $R^{12}$ to $R^{27}$ for the general formula (A), any of $R^{32}$ to $R^{37}$ for the general formula (B), any of $R^{42}$ to $R^{47}$ and $R^{49}$ for the general formula (C), any of $R^{52}$, $R^{53}$, $R^{56}$, $R^{57}$, $R^{59}$, and $R^{60}$ for the general formula (D), and any of $R^{62}$, $R^{63}$, $R^{66}$, $R^{67}$, $R^{69}$, and $R^{70}$ for the general formula (E).

In the general formulae (A) to (E), $R^{21}$ and $R^{22}$, $R^{22}$ and $R^{23}$, $R^{23}$ and $R^{24}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{59}$ and $R^{60}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, and $R^{69}$ and $R^{70}$ each may be bonded to each other to form a cyclic structure.

The cyclic structure may be an aromatic ring or an aliphatic ring, and may contain a heteroatom, and the cyclic structure may be a condensed ring containing two or more rings. The hetero atom referred herein is preferably selected from a group consisting of a nitrogen atom, an oxygen atom, and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring, and a cycloheptene ring.

The groups represented by the general formulae (A) to (E) present in the general formula (1) are preferably groups that are represented by any one of the general formulae (A) to (E). Preferred examples thereof include a case where the substituents are groups represented by the general formula (A), and a case where all the substituents are represented by the general formula (B).

The number n of the ligand having the particular structure constituting the organic metal complex represented by the general formula (1) is an integer of from 1 to 3. In the case where the organic metal complex represented by the general formula (1) has plural ligands (i.e., in the case where n is 2 or more), the plural ligands may be the same as or different from each other, and are preferably the same as each other.

The organic metal complex represented by the general formula (1) may have L, i.e., a ligand that is not encompassed by the general formula of the ligand shown above M. The number m of the ligand L is an integer of from 0 to 2, and m is preferably 0 or 1, and may be 0.

Examples of the ligand L include a substituted or unsubstituted aryloxy ligand. Examples of the substituted or unsubstituted aryloxy ligand include a substituted or unsubstituted phenoxy ligand and a substituted or unsubstituted naphthoxy ligand. Examples of the substituent substituted on the aryloxy group include the substituents exemplified for the substituent that is capable of being represented by $R^{21}$ to $R^{28}$, $R^{31}$ to $R^{38}$, $R^{41}$ to $R^{49}$, and $R^{51}$ to $R^{70}$. Among these, a substituted or unsubstituted diarylamino group is preferably used, and for example, a diphenylamino group is preferably used.

M represents the center metal of the organic metal complex represented by the general formula (1). M represents an element of the group 1 except for hydrogen, the group 2, the group 11, the group 12, or the group 13 of the periodic table. The element of the group 1 except for hydrogen specifically includes lithium, sodium, potassium, rubidium, cesium, and francium. The element of the group 2 includes beryllium, magnesium, calcium, strontium, barium, and radium, the element of the group 11 includes copper, silver, gold, and roentgenium, the element of the group 12 includes zinc, cadmium, mercury, and copernicium, and the element of the group 13 includes boron, aluminum, gallium, indium, and thallium. Among these, M is preferably lithium, magnesium, aluminum, or zinc.

In the case where M is a trivalent metal, such as aluminum, it is preferred that in the general formula (1), n is 2, and m is 1. In the case where M is a divalent metal, such as zinc, it is preferred that in the general formula (1), n is 2, and m is 0.

Specific examples of the organic metal complex represented by the general formula (1) are shown below. However, the organic metal complex represented by the general formula (1) capable of being used in the invention is not construed as being limited to the specific examples.

Compound 1
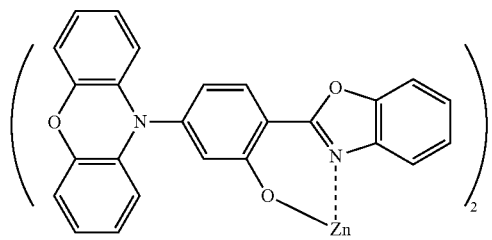
Compound 2
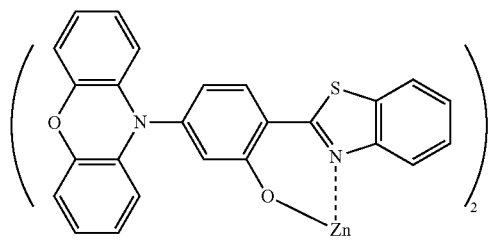
Compound 3
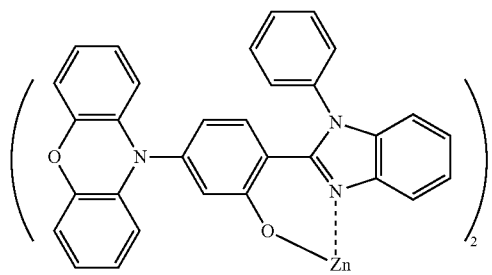
Compound 4
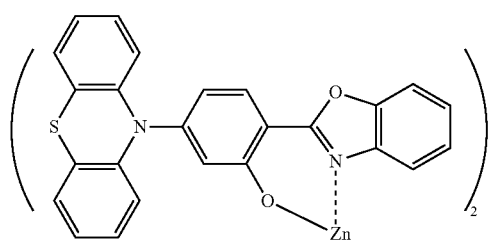
Compound 5
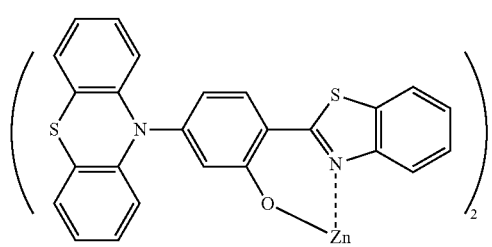
Compound 6
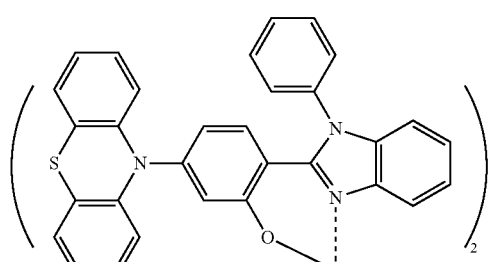
-continued
Compound 7
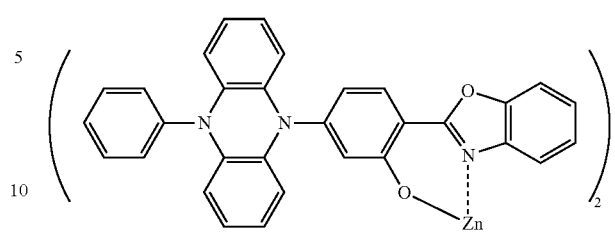
Compound 8
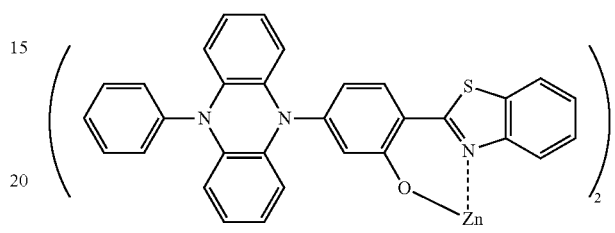
Compound 9
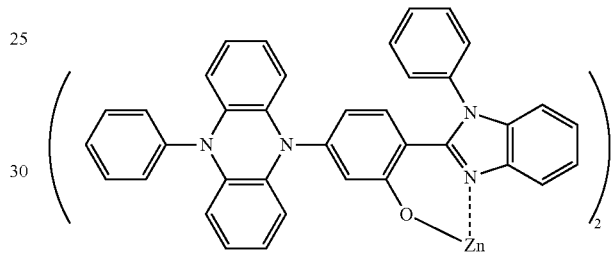
Compound 10
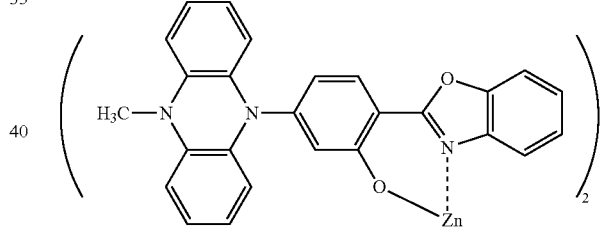
Compound 11
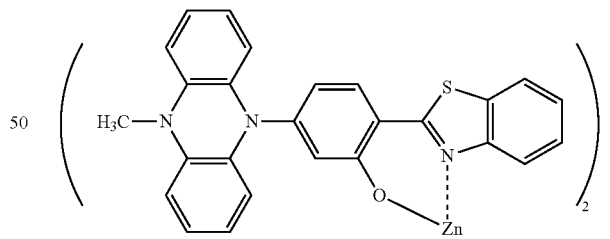
Compound 12

Compound 13
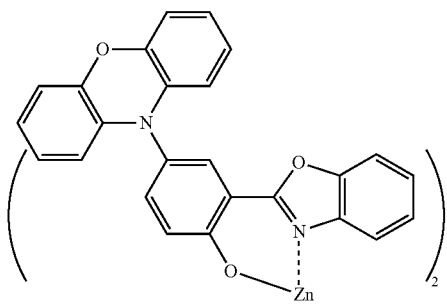
Compound 14
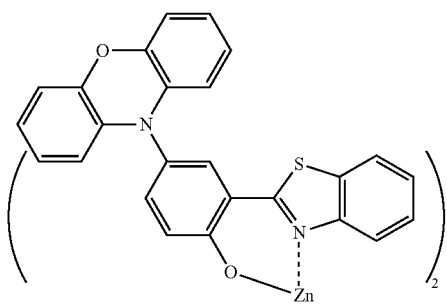
Compound 15
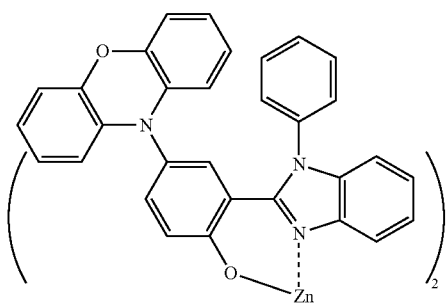
Compound 16
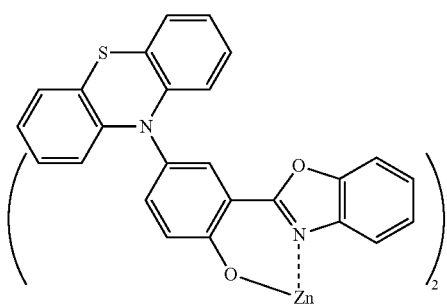
Compound 17
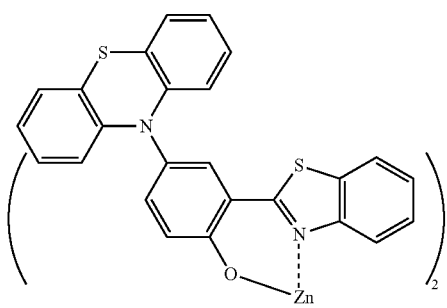
Compound 18
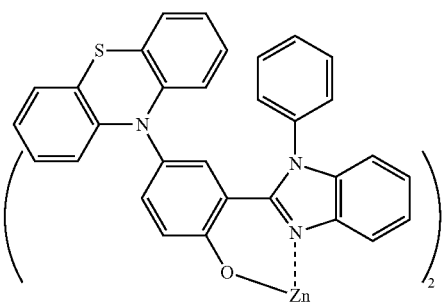
Compound 19
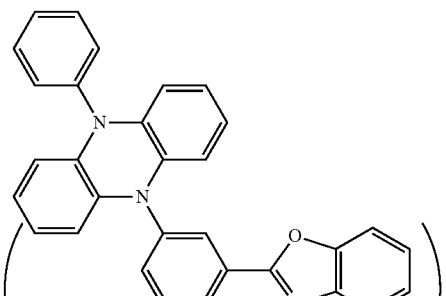
Compound 20
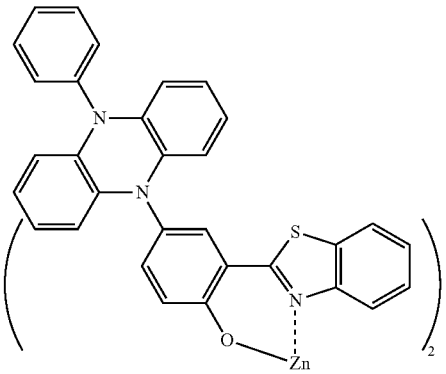
Compound 21
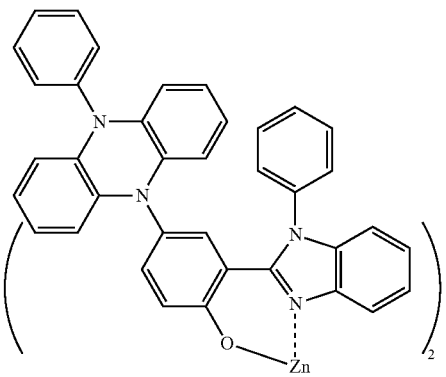

Compound 22
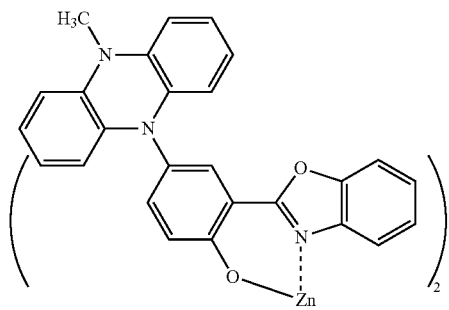
Compound 23
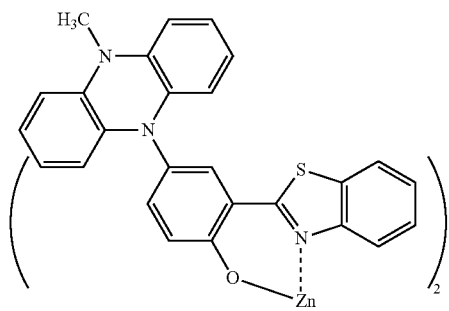
Compound 24
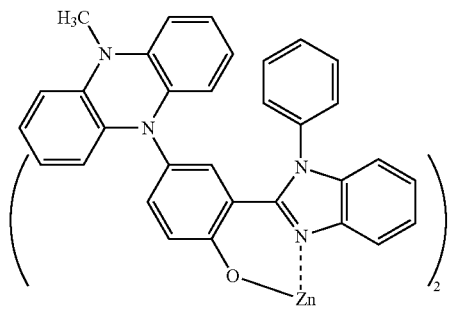
Compound 25
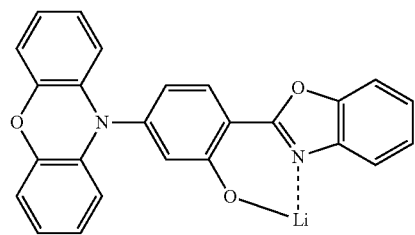
Compound 26
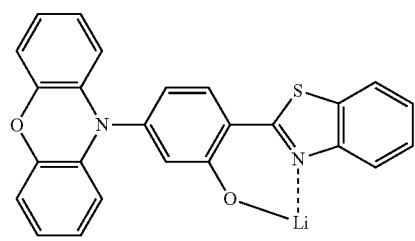
Compound 27
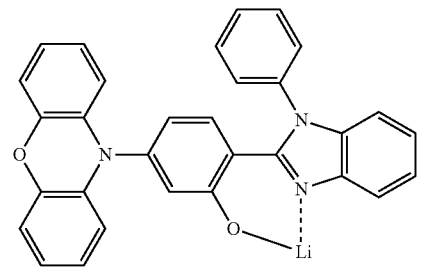
Compound 28
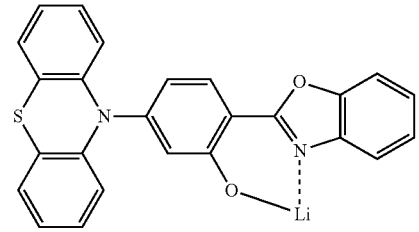
Compound 29
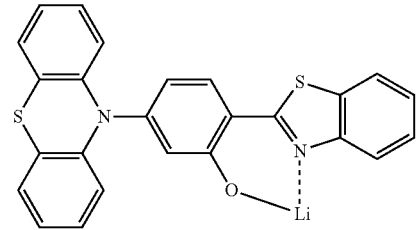
Compound 30
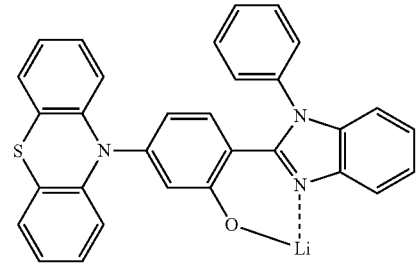
Compound 31
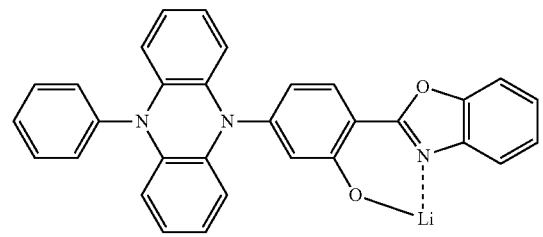
Compound 32
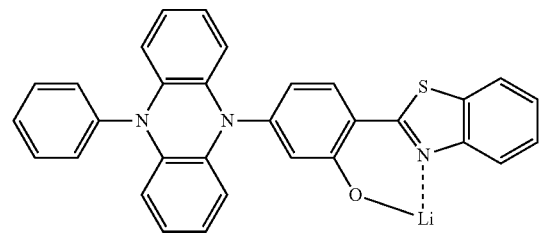

Compound 33
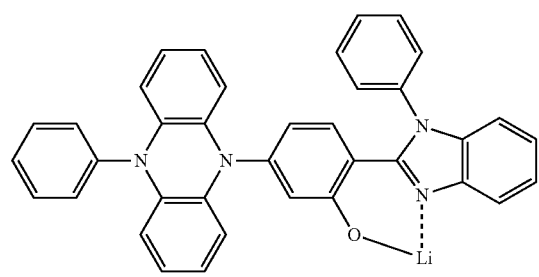
Compound 34
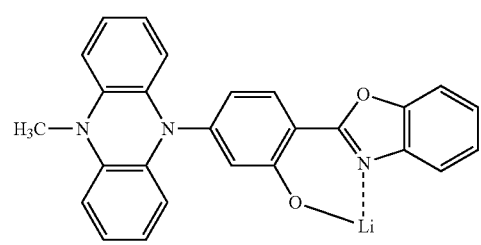
Compound 35
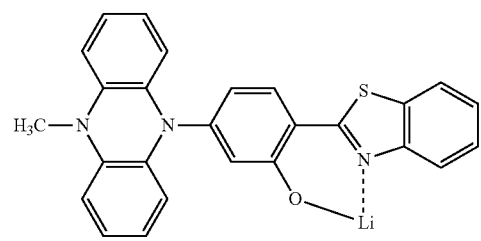
Compound 36
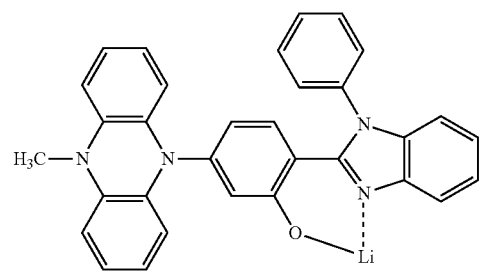
Compound 37
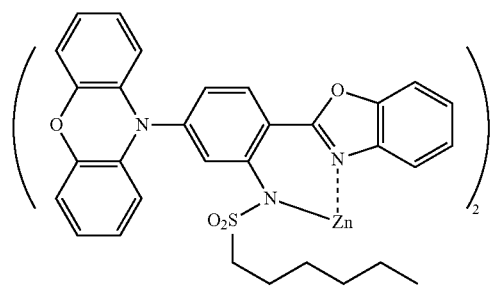
Compound 38
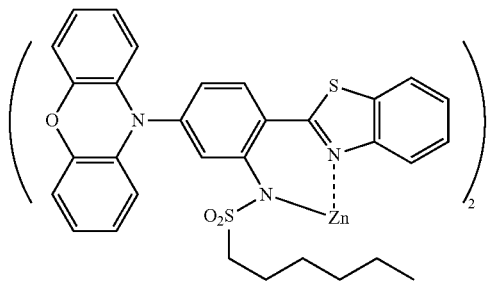
Compound 39
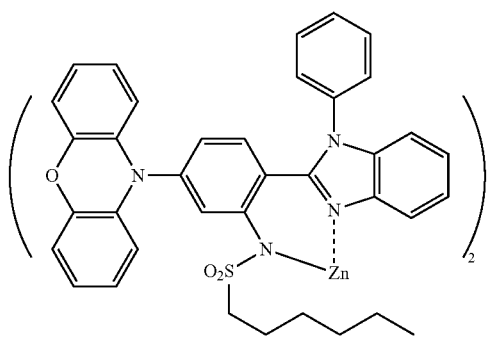
Compound 40
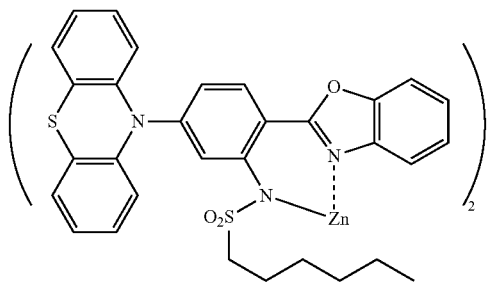
Compound 41
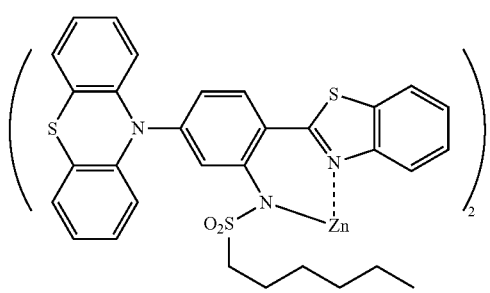
Compound 42
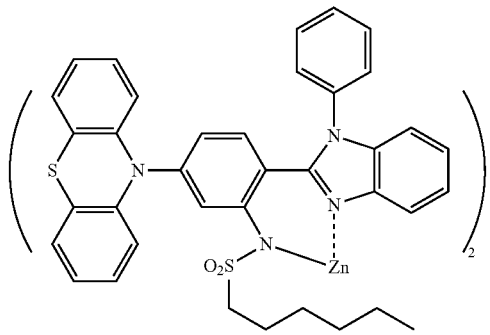

Compound 43
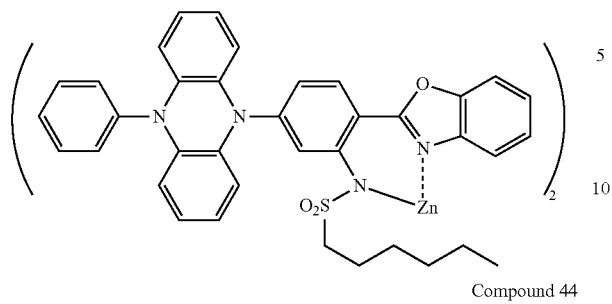
Compound 44
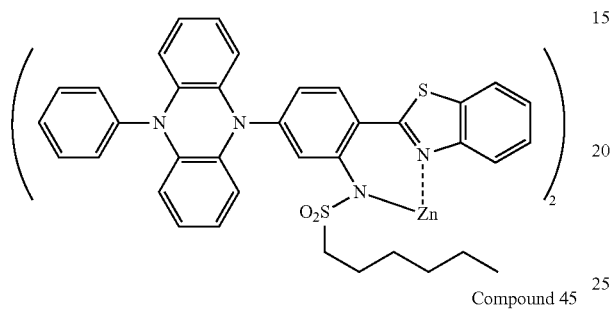
Compound 45
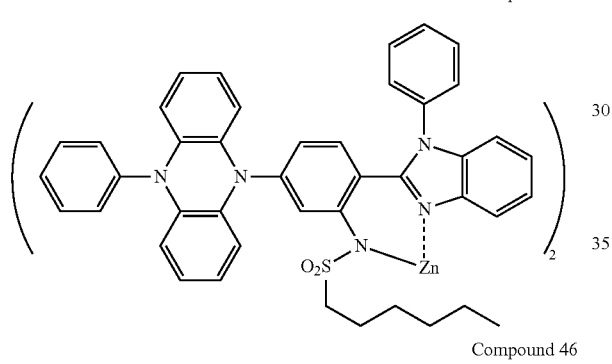
Compound 46
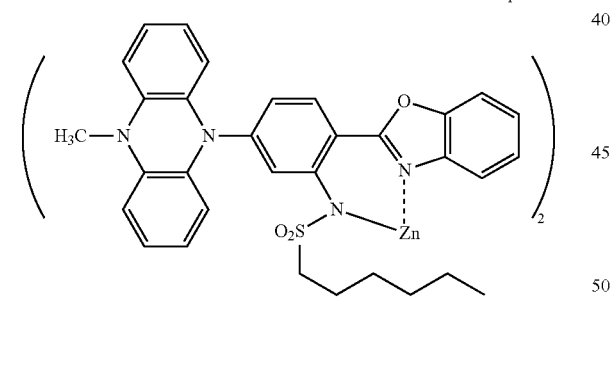
Compound 47
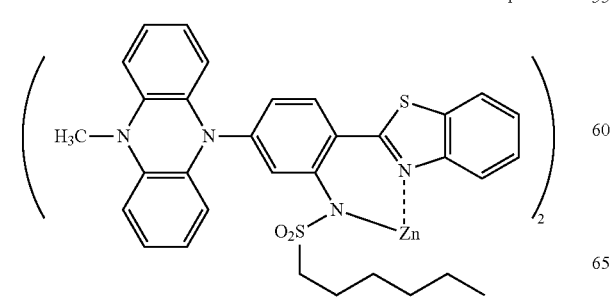
Compound 48
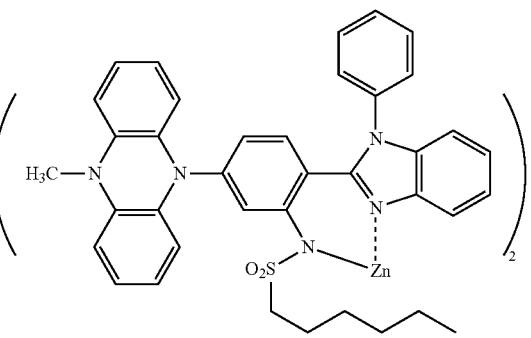
Compound 49
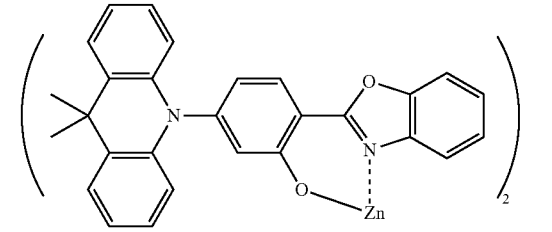
Compound 50
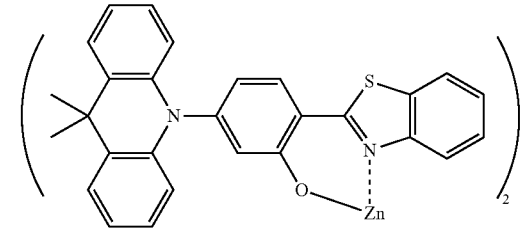
Compound 51
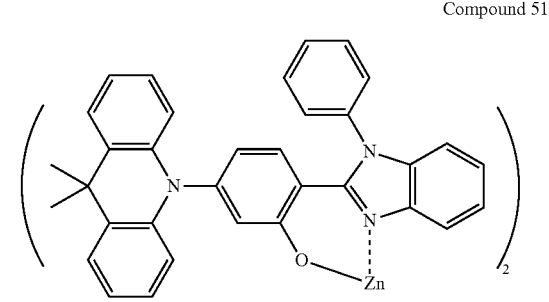
Compound 52
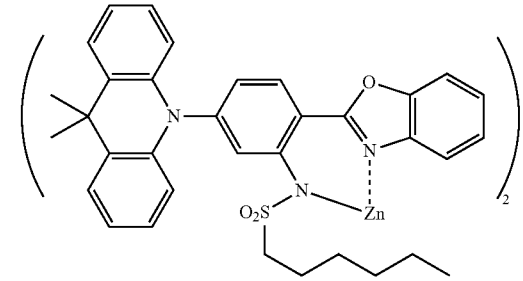

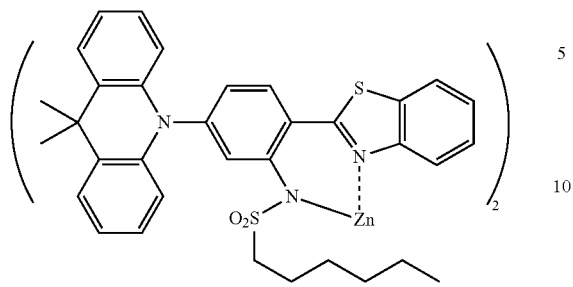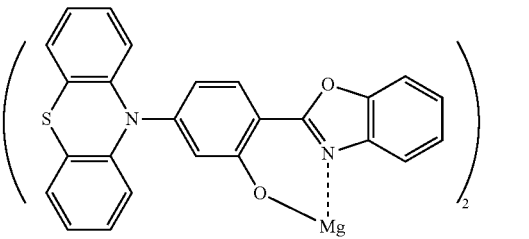

Compound 64
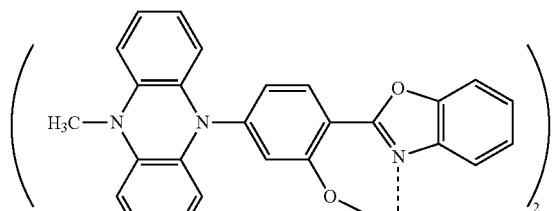

Compound 65
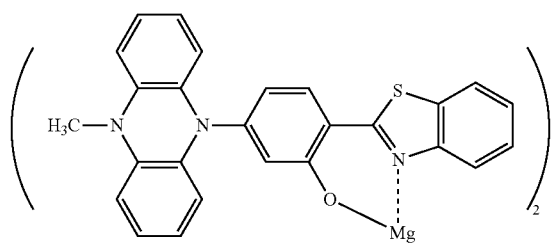

Compound 66
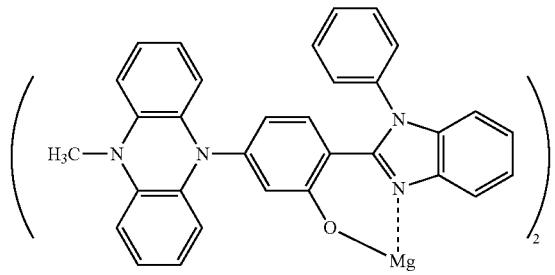

Compound 67
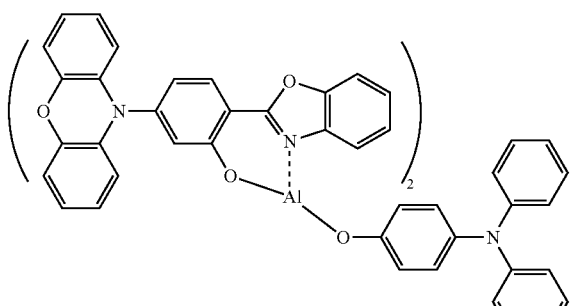

Compound 68
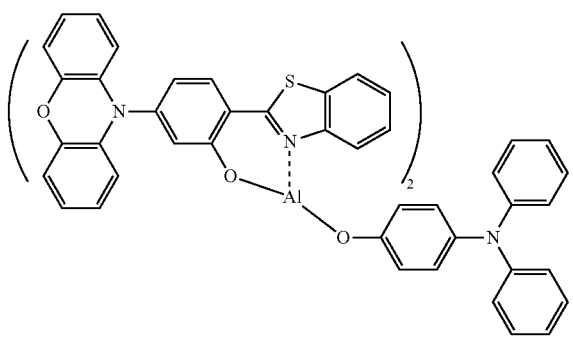

Compound 69
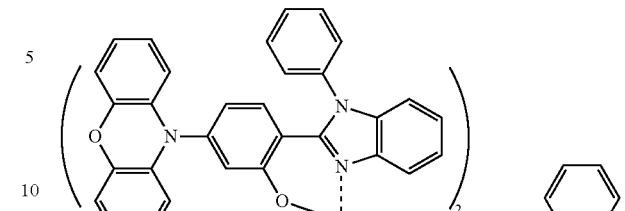

Compound 70
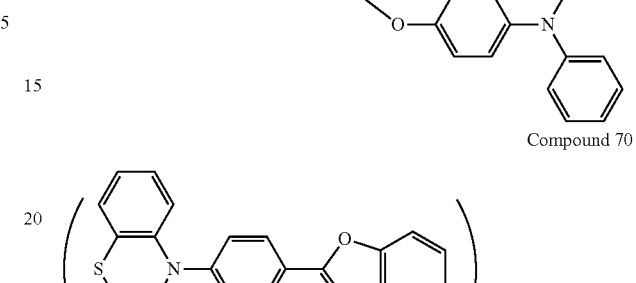

Compound 71
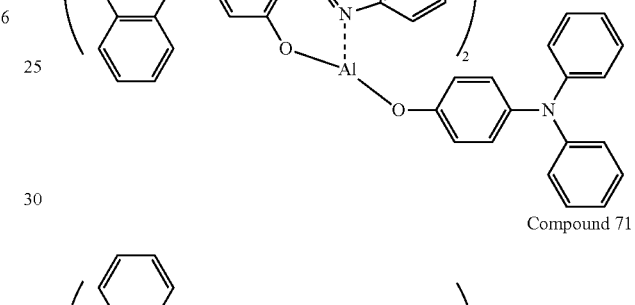

Compound 72
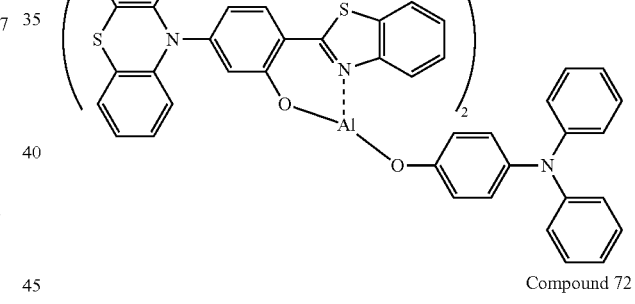

The molecular weight of the organic metal complex represented by the general formula (1) is preferably 1,500 or less, more preferably 1,200 or less, further preferably 1,000 or less, and still further preferably 800 or less, for example, in the case where an organic layer containing the organic metal complex represented by the general formula (1) is intended to be formed as a film by a vapor deposition method. The lower limit of the molecular weight is the molecular weight of the smallest compound represented by the general formula (1).

The organic metal complex represented by the general formula (1) may be formed into a film by a coating method irrespective of the molecular weight thereof. The organic metal complex that has a relatively large molecular weight may be formed into a film by a coating method.

As an application of the invention, it may be considered that a compound that contains plural structures each represented by the general formula (1) in the molecule is used as a light emitting material.

For example, it may be considered that a polymerizable group is introduced in advance to the structure represented by the general formula (1), and a polymer obtained by polymerizing the polymerizable group is used as a light emitting material. Specifically, it may be considered that a monomer that has a polymerizable functional group at any of $R^1$ to $R^8$ in the general formula (1) is prepared, and is homopolymerized or copolymerized with another monomer to prepare a polymer containing repeating units, and the polymer is used as a light emitting material. In alternative, it may be considered that the compounds that has the structure represented by the general formula (1) are reacted to form a dimer or a trimer, and the dimer or the trimer is used as a light emitting material.

Examples of the polymer having the repeating unit containing the structure represented by the general formula (1) include a polymer containing a structure represented by the following general formula (2) or (3).

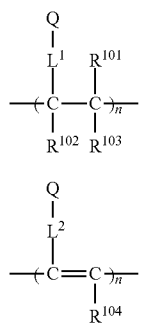

General Formula (2)

General Formula (3)

In the general formulae (2) and (3), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (2) and (3), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $R^1$ to $R^8$ of the structure of the general formula (1), $R^9$ of the structure of the general formula (C), $R^{10}$ or $R^{11}$ of the structure of the general formula (D), and $R^{12}$ or $R^{13}$ of the structure of the general formula (E) constituting Q. Two or more of the linking groups may be boded to one group represented by Q to form a crosslinked structure or a network structure.

Specific examples of the structure of the repeating unit include structures represented by the following formulae (4) to (7).

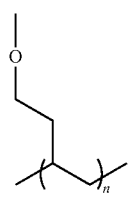

Formula (4)

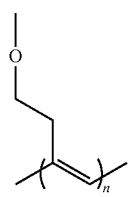

Formula (5)

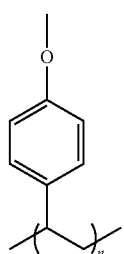

Formula (6)

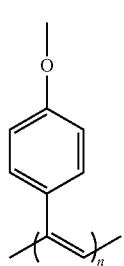

Formula (7)

The polymer having the repeating unit containing the structure represented by any of the formulae (4) to (7) may be synthesized in such a manner that a hydroxyl group is introduced to any of $R^1$ to $R^8$ in the structure represented by the general formula (1), and the hydroxyl group as a linker is reacted with the following compound to introduce a polymerizable group thereto, followed by polymerizing the polymerizable group.

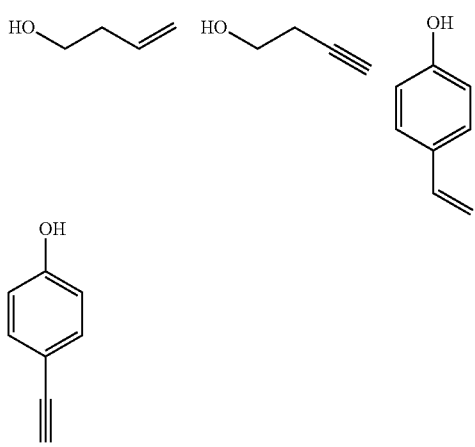

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene, but the invention is not limited to the repeating units shown herein.

Synthesis Method of Organic Metal Complex Represented by General Formula (1)

The organic metal complex represented by the general formula (1) may be synthesized by combining the known reactions. For example, the organic metal complex represented by the general formula (1), in which X and Y are oxygen atoms, $Z^2$ is a group represented by the general formula (A), and M is zinc, may be synthesized in such a manner that the ligand is synthesized according to the following synthesis route, and the ligand is coordinated to zinc. In the synthesis of the ligand, the synthesis route used for the intermediate product 1 may be any of the route A and the route B, and the route A is preferably used. According thereto, the intermediate product 1 may be obtained at a high yield.

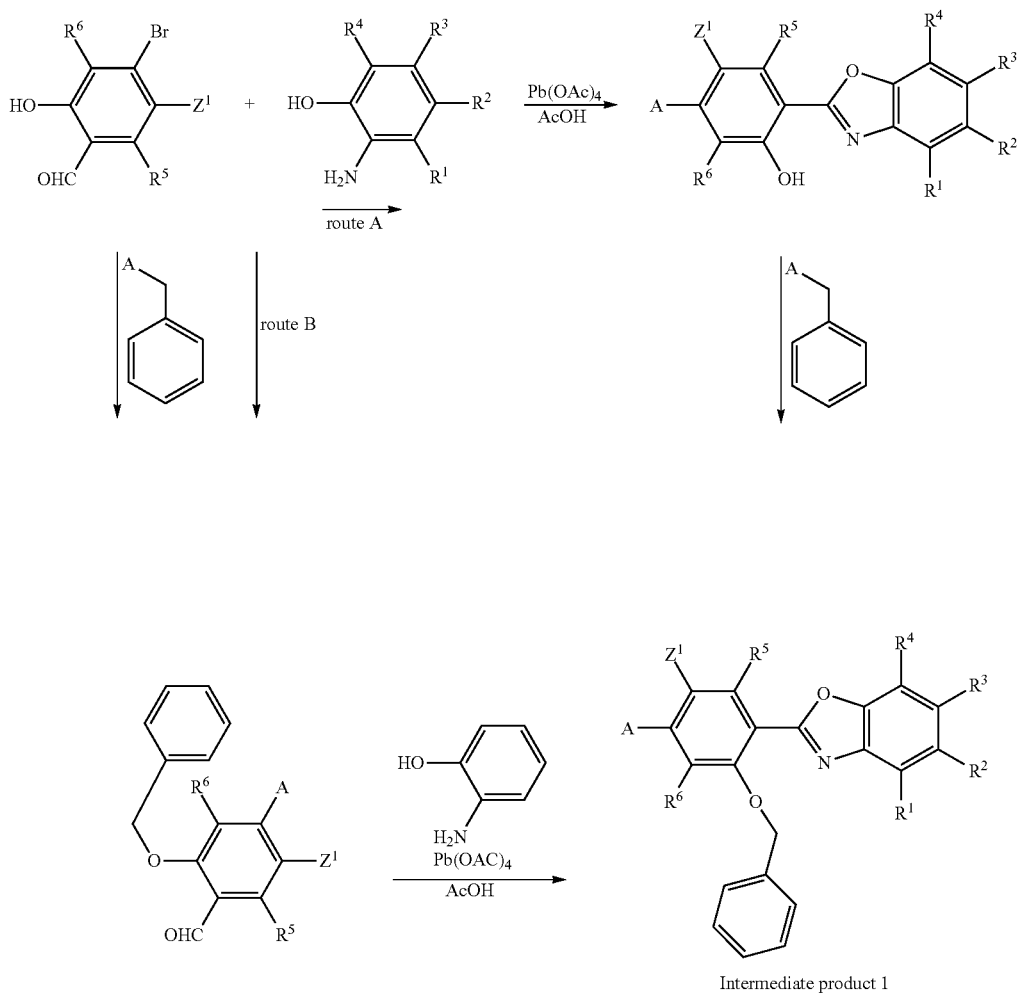

Intermediate product 1

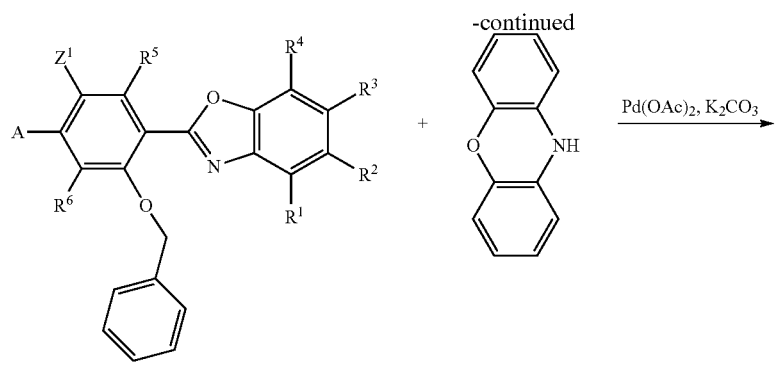

Intermediate product 1

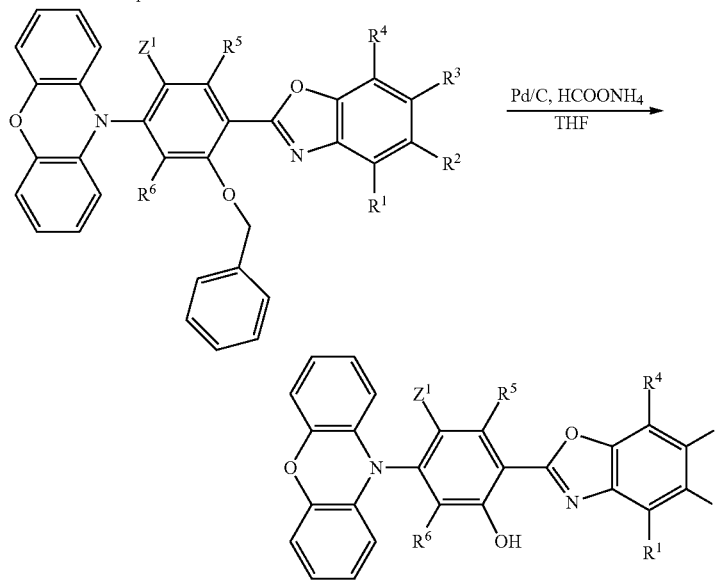

Ligand

Synthesis of Complex

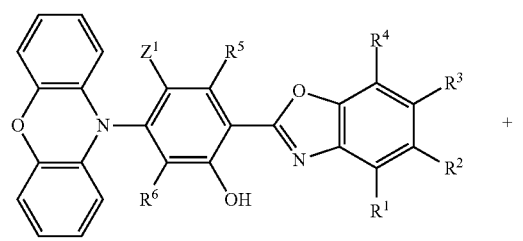

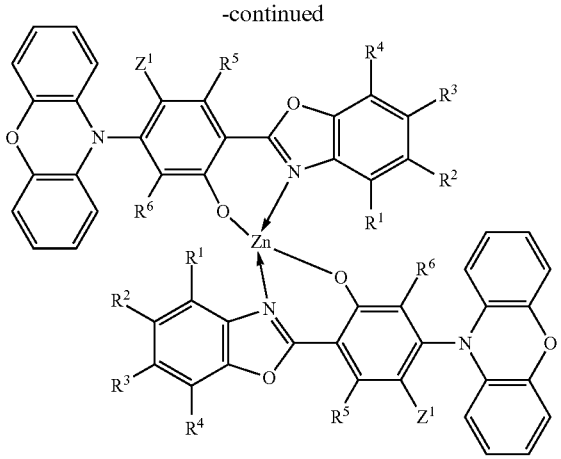

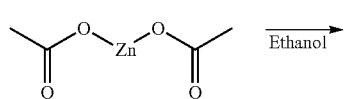

For the descriptions of $R^1$ to $R^6$ and $Z^1$ in the reaction scheme, reference may be made to the corresponding descriptions in the general formula (1). In the reaction scheme, A represents a halogen atom, examples of which include a fluorine atom, a chlorine atom, a bromine atom and an iodine atom, and a chlorine atom, a bromine atom and an iodine atom are preferred.

For the details of the reaction, reference may be made to the synthesis examples described later. The organic metal complex represented by the general formula (1) may also be synthesized by combining the other known synthesis reactions.

Energy Difference $\Delta E_{ST}$ of Organic Metal Complex

The inventors have found that an organic metal complex that satisfies the following expressions (I) and (II) is excellent in light emission characteristics and is useful.

$$S_C - T_C \leq 0.2 \text{ eV} \quad \text{Expression (I)}$$

$$S_L - T_L \geq 0.2 \text{ eV} \quad \text{Expression (II)}$$

In the expressions (I) and (II), Sc represents the energy of the singlet excited state of the organic metal complex; $T_C$ represents the energy of the triplet excited state of the organic metal complex; $S_L$ represents the energy of the singlet excited state of the ligand constituting the organic metal complex; and $T_L$ represents the energy of the triplet excited state of the ligand constituting the organic metal complex. In the description herein, the energy of the singlet excited state and the energy of the triplet excited state mean: the values that are measured described in the examples later, respectively. In the following description, the values of $S_C - T_C$ and $S_L - T_L$ each may be referred to as the energy difference $\Delta E_{ST}$ in some cases.

The organic metal complex of the invention has the energy differences $\Delta E_{ST}$ of the organic metal complex itself and the ligand constituting the organic metal complex that are both 0.2 eV or less, and thereby can provide a high light emission efficiency. In particular, due to the small energy differences $\Delta E_{ST}$ of the ligand, the light emission efficiency can be remarkably enhanced, as compared to the ordinary organic metal complex light emitting materials.

Accordingly, an organic metal complex excellent in light emission characteristics can be provided by designing the molecule to satisfy the expressions (I) and (II). For example, an organic metal complex excellent in light emission characteristics can be provided in such a manner that the values of $S_C - T_C$ and $S_L - T_L$ are calculated for various chemical structures by using a known calculation method, and an organic metal complex is actually produced to have a structure that results in calculation results satisfying the expressions (I) and (II). Furthermore, the general formula of an organic metal complex excellent in light emission characteristics can be provided by generalizing the structure that results in calculation results satisfying the expressions (I) and (II) through calculation for various structure.

The value of $S_C - T_C$ (energy difference $\Delta E_{ST}$) of the organic metal complex is preferably 1.0 eV or less, more preferably 0.7 eV or less, and further preferably 0.3 eV or less. The value of $S_L - T_L$ (energy difference $\Delta E_{ST}$) of the ligand constituting the organic metal complex is preferably 1.0 eV or less, more preferably 0.7 eV or less, and further preferably 0.3 eV or less.

The energy of the singlet excited state of the organic metal complex $S_C$ is preferably from 1.5 to 3.5 eV, more preferably from 1.7 to 3.3 eV, and further preferably from 1.9 to 3.1 eV. The energy of the triplet excited state of the organic metal complex Tc is preferably from 0.5 to 3.5 eV, more preferably from 1.0 to 3.2 eV, and further preferably from 1.7 to 3.1 eV.

Organic Light Emitting Device

The organic metal complex represented by the general formula (1) of the invention is useful as a light emitting material of an organic light emitting device. Accordingly, the organic metal complex represented by the general formula (1) of the invention may be effectively used as a light emitting material in a light emitting layer of an organic light emitting device. The organic metal complex represented by the general formula (1) includes a delayed fluorescent material emitting delayed fluorescent light. Thus, the invention provides an invention relating to a light emitting material containing the organic metal complex represented by the general formula (1), an invention relating to a delayed fluorescent material having the structure represented by the general formula (1), an invention relating to the use of the organic metal complex represented by the general formula (1) as a delayed fluorescent material, and an invention relating to a method for emitting delayed fluorescent light with the organic metal complex represented by the general formula (1). An organic light emitting device that uses the compound as a light emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light emitting material to form an excited state for the light emitting material, with which light is emitted. In the case of a carrier injection type organic electroluminescent device, in general, excitons that are excited to the singlet excited state are 25% of the total excitons generated, and the remaining 75% thereof are excited to the triplet excited state. Accordingly, the use of phosphorescence, which is light emission from the triplet excited state, provides a high energy use efficiency. However, the triplet excited state has a long lifetime and thus causes saturation of the excited state and deactivation of energy through mutual action with the excitons in the triplet excited state, and therefore the quantum yield of phosphorescence may generally be often not high. A delayed fluorescent material emits fluorescent light through the mechanism that the energy of excitons transits to the triplet excited state through intersystem crossing or the like, and then transits to the singlet excited state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the singlet excited state normally emit fluorescent light. On the other hand, the excitons in the triplet excited state emit fluorescent light through intersystem crossing to the singlet excited state by absorbing the heat generated by the device. At this time, the light emitted through reverse intersystem crossing from the triplet excited state to the singlet excited state has the same wavelength as fluorescent light since it is light emission from the singlet excited state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the singlet excited state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the triplet excited state to the singlet excited state sufficiently with the heat of the device, thereby emitting delayed fluorescent light, and thus the use of the compound may drastically enhance the light emission efficiency.

The use of the organic metal complex represented by the general formula (1) of the invention as a light emitting material of a light emitting layer may provide an excellent organic light emitting device, such as an organic photoluminescent device (organic PL device) and an organic electroluminescent device (organic EL device). At this time, the compound represented by the general formula (1) of the invention may have a function of assisting light emission of another light emitting material contained in the light emitting layer, i.e., as a so-called assist dopant. Specifically, the compound represented by the general formula (1) of the invention contained in the light emitting layer may have a lowest excited singlet energy level that is between the lowest excited singlet energy level of the host material contained in the light emitting layer and the lowest excited singlet energy level of the another light emitting material contained in the light emitting layer.

The organic photoluminescent device has a structure containing a substrate having formed thereon at least a light emitting layer. The organic electroluminescent device has a structure containing at least an anode, a cathode and an organic layer formed between the anode and the cathode. The organic layer contains at least a light emitting layer, and may be formed only of a light emitting layer, or may have one or more organic layer in addition to the light emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light emitting layer, 6 denotes an electron transporting layer, and 7 denotes a cathode.

The members and the layers of the organic electroluminescent device will be described below. The descriptions for the substrate and the light emitting layer may also be applied to the substrate and the light emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thing film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light Emitting Layer

The light emitting layer is a layer, in which holes and electrons injected from the anode and the cathode, respectively, are recombined to form excitons, and then the layer emits light. A light emitting material may be solely used as the light emitting layer, but the light emitting layer preferably contains a light emitting material and a host material. The light emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light emitting material are confined in the light emitting material. Accordingly, a host material is preferably used in addition to the light emitting material in the light emitting layer. The host material used may be an organic compound that has excited singlet energy and excited triplet energy, at least one of which is higher than those of the light emitting material of the invention. As a result, the singlet excitons and the triplet excitons generated in the light emitting material of the invention are capable of being confined in the molecules of the light emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light emitting device and the organic electroluminescent device of the invention, the light emission occurs in the light emitting material of the invention contained in the light emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light emitting material contained in the light emitting layer is preferably 0.1% by weight or more, and more preferably 1% by weight or more, and is preferably 50% by weight or less, more preferably 20% by weight or less, and further preferably 10% by weight or less.

The host material in the light emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light emitting layer or the hole transporting layer and between the cathode and the light emitting layer or the electron transporting layer. The injection layer may be provided depending on necessity.

Barrier Layer

The barrier layer is a layer that is capable of inhibiting charges (electrons or holes) and/or excitons present in the light emitting layer from being diffused outside the light emitting layer. The electron barrier layer may be disposed between the light emitting layer and the hole transporting layer, and inhibits electrons from passing through the light emitting layer toward the hole transporting layer. Similarly, the hole barrier layer may be disposed between the light emitting layer and the electron transporting layer, and inhibits holes from passing through the light emitting layer toward the electron transporting layer. The barrier layer may also be used for inhibiting excitons from being diffused outside the light emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light emitting layer.

Exciton Barrier Layer

The exciton barrier layer is a layer for inhibiting excitons generated through recombination of holes and electrons in the light emitting layer from being diffused to the charge transporting layer, and the use of the layer inserted enables effective confinement of excitons in the light emitting layer, and thereby enhances the light emission efficiency of the device. The exciton barrier layer may be inserted adjacent to the light emitting layer on any of the side of the anode and the side of the cathode, and on both the sides. Specifically, in the case where the exciton barrier layer is present on the side of the anode, the layer may be inserted between the hole transporting layer and the light emitting layer and adjacent to the light emitting layer, and in the case where the layer is inserted on the side of the cathode, the layer may be inserted between the light emitting layer and the cathode and adjacent to the light emitting layer. Between the anode and the exciton barrier layer that is adjacent to the light emitting layer on the side of the anode, a hole injection layer, an electron barrier layer and the like may be provided, and between the cathode and the exciton barrier layer that is adjacent to the light emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the organic metal complex represented by the general formula (1) may be used not only in the light emitting layer but also in the other layers than the light emitting layer.

In this case, the organic metal complex represented by the general formula (1) used in the light emitting layer and the organic metal complex represented by the general formula (1) used in the other layers than the light emitting layer may be the same as or different from each other. For example, the organic metal complex represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and n represents an integer of from 3 to 5.

Preferred examples of a compound that may also be used as the host material of the light emitting layer are shown below.

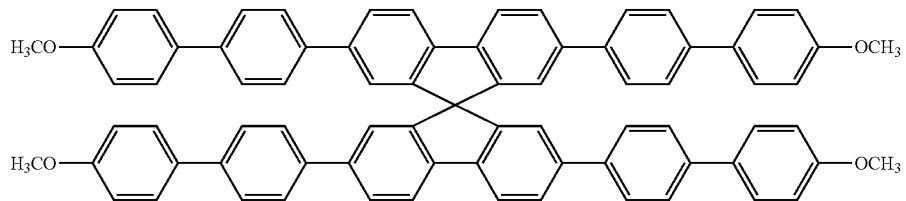

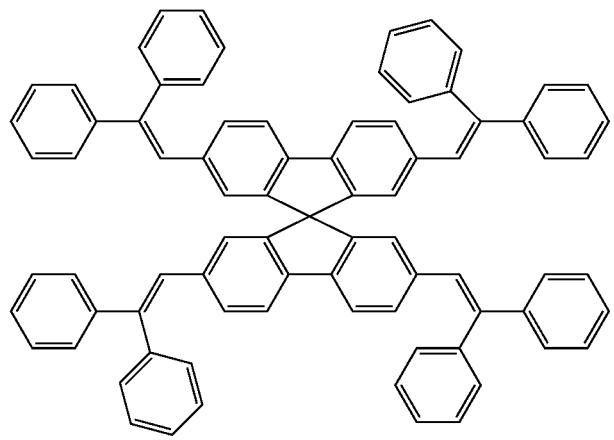

41 42
-continued
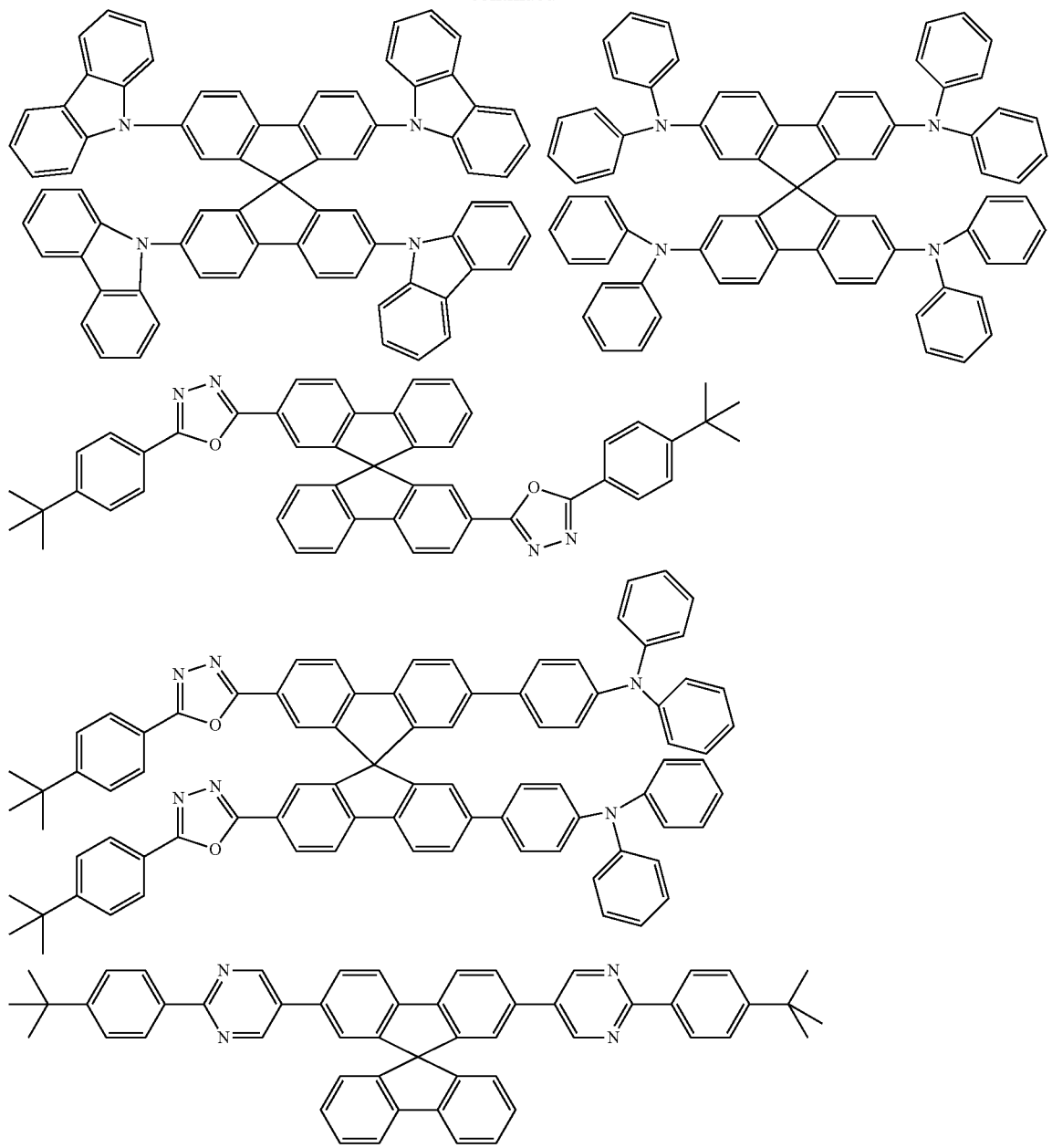
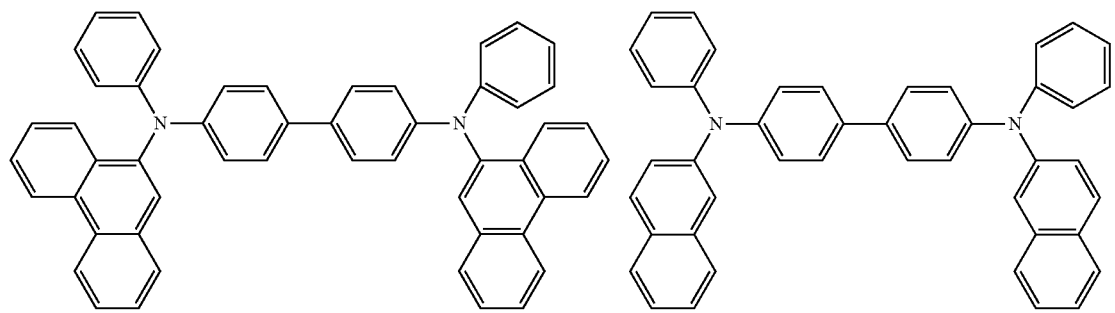

-continued
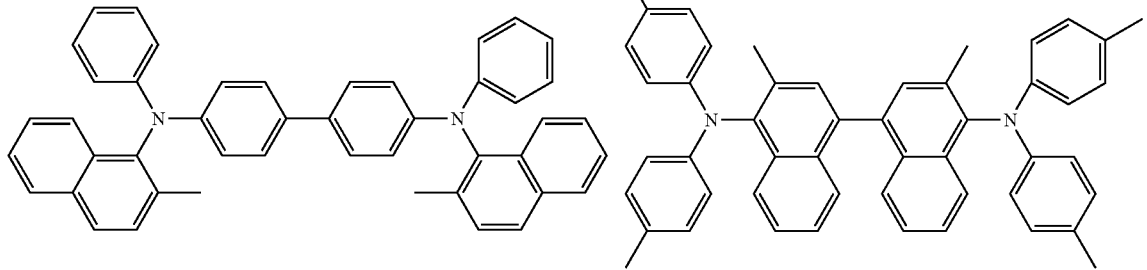
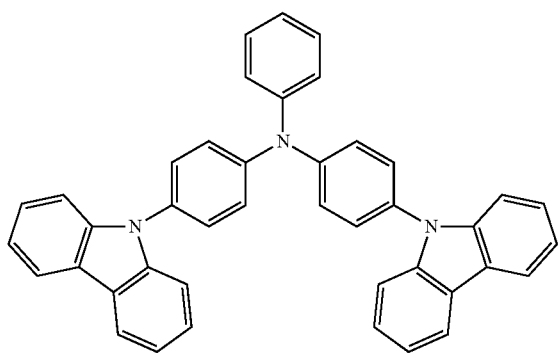
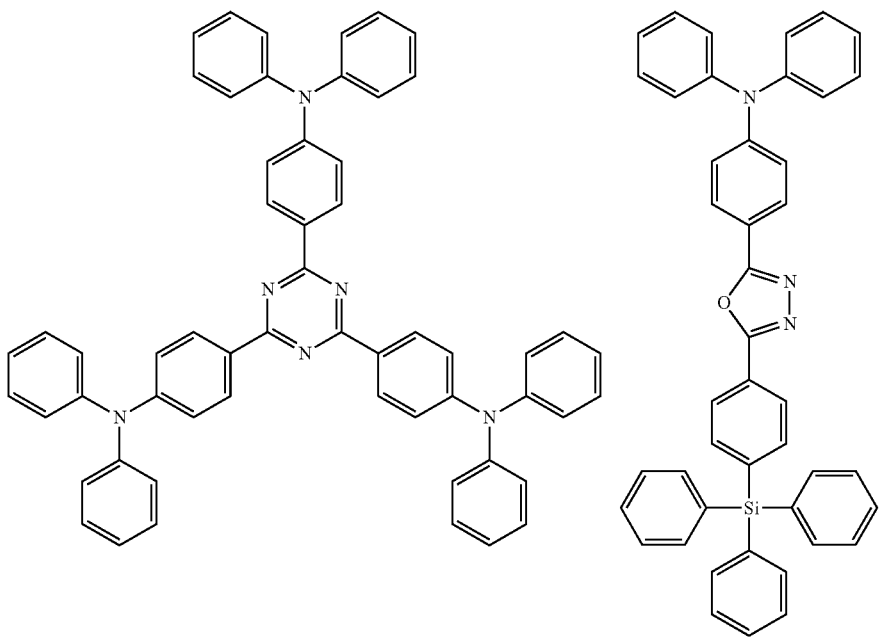

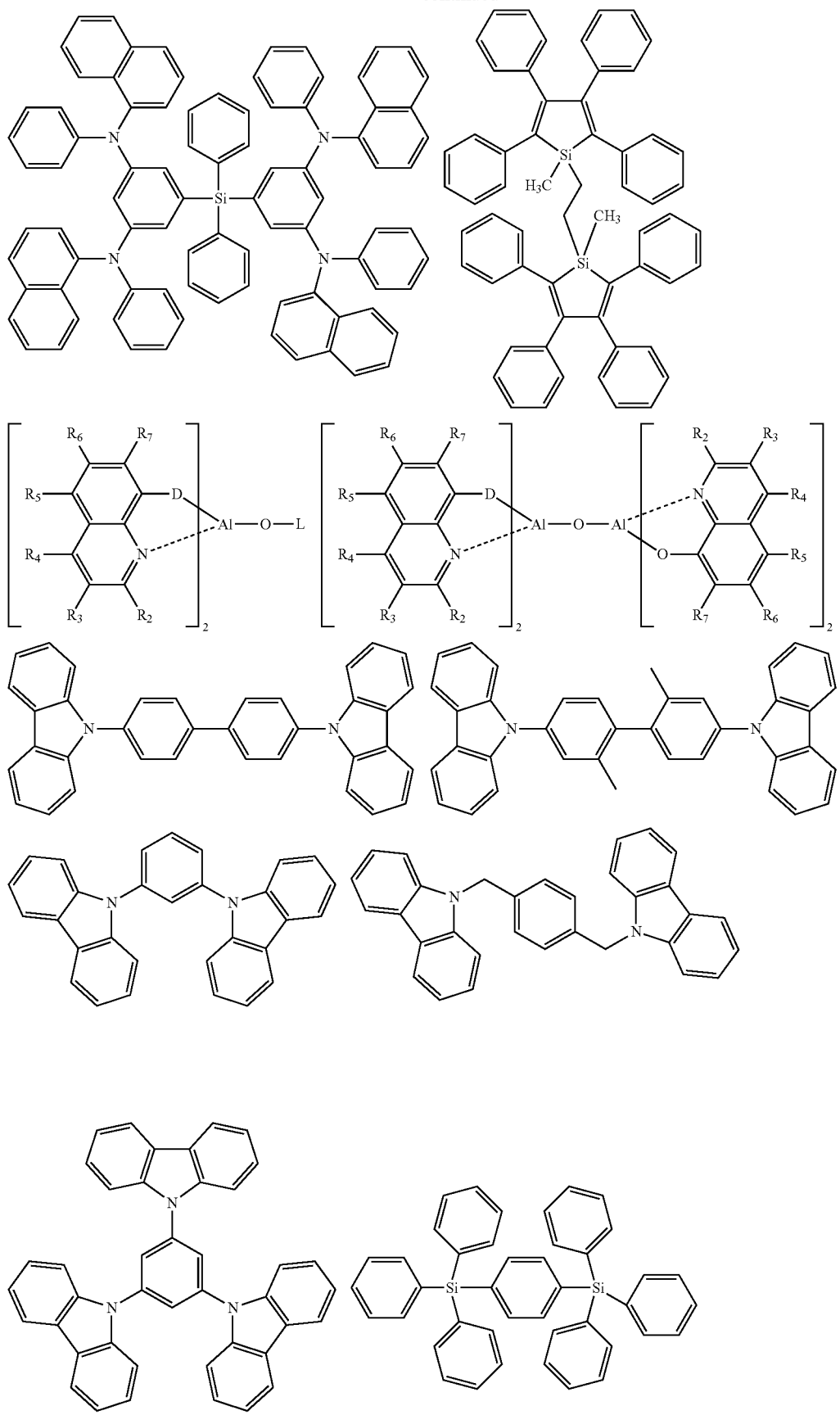

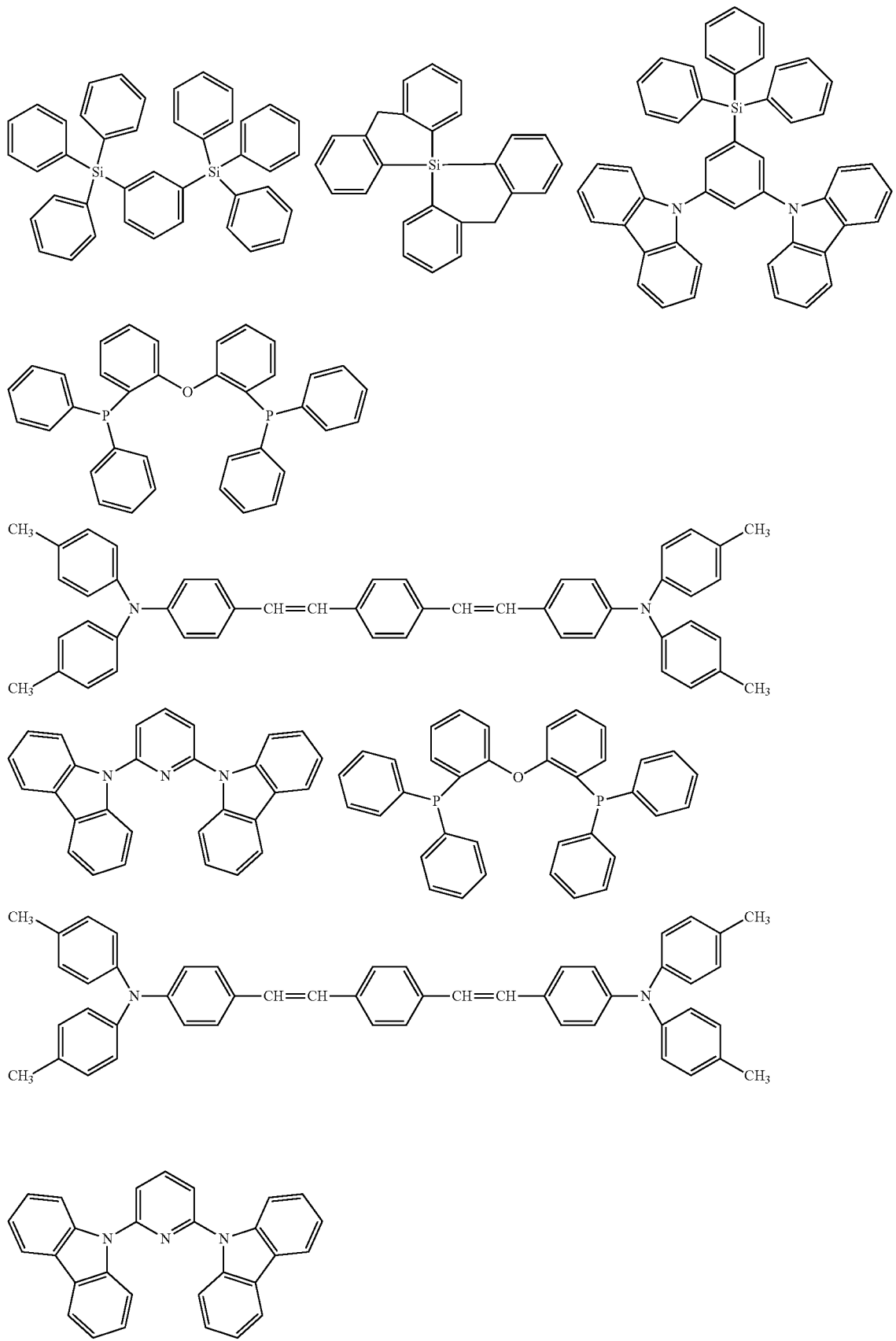

Preferred examples of a compound that may be used as the hole injection material are shown below.
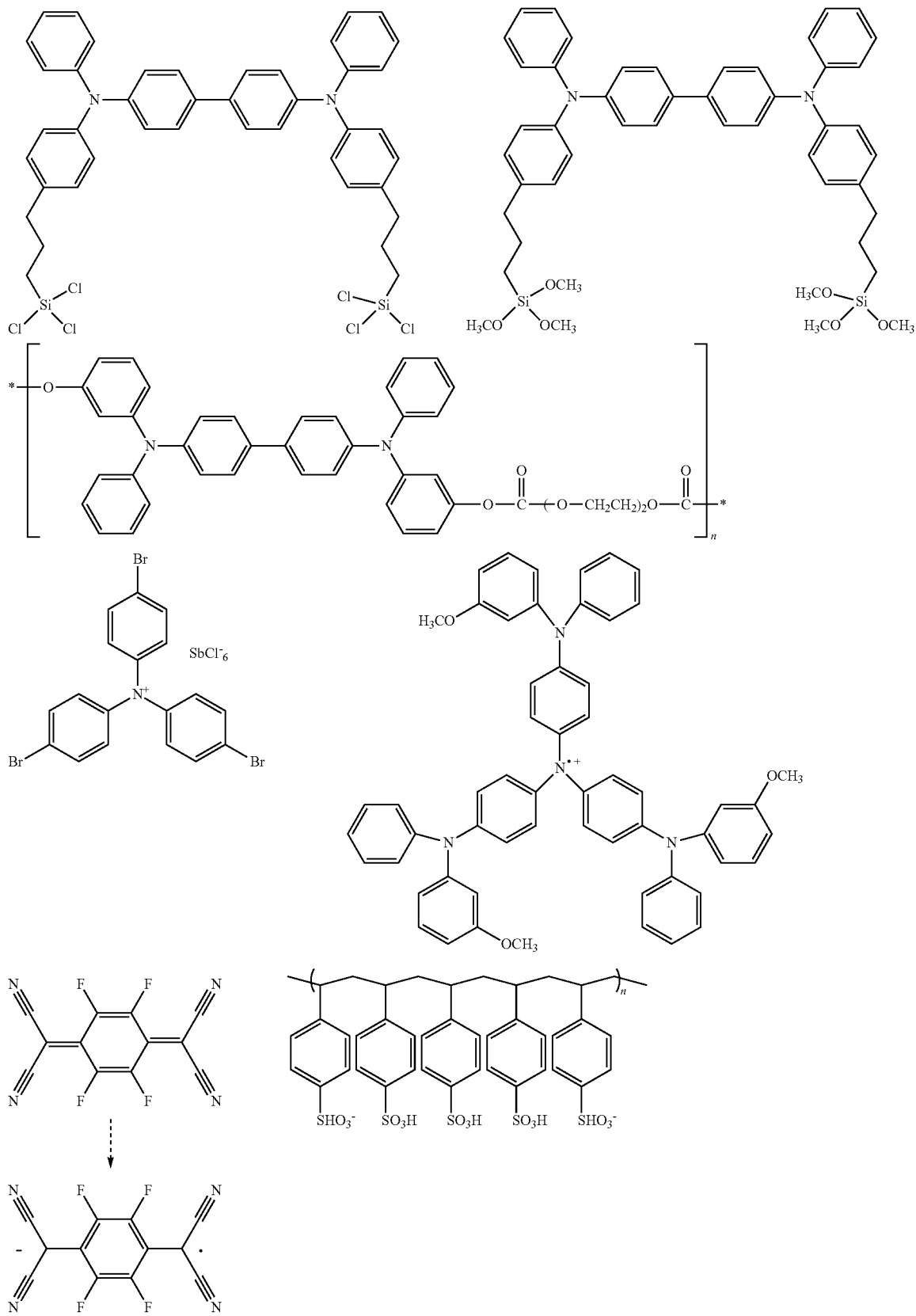

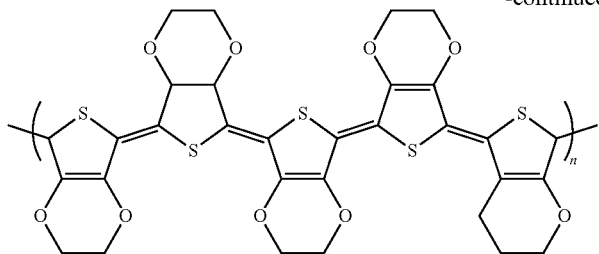
Preferred examples of a compound that may be used as the hole transporting material are shown below.
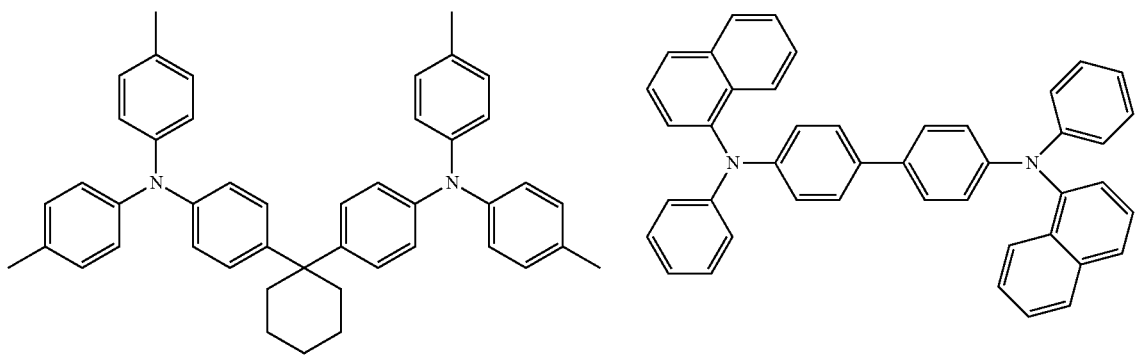
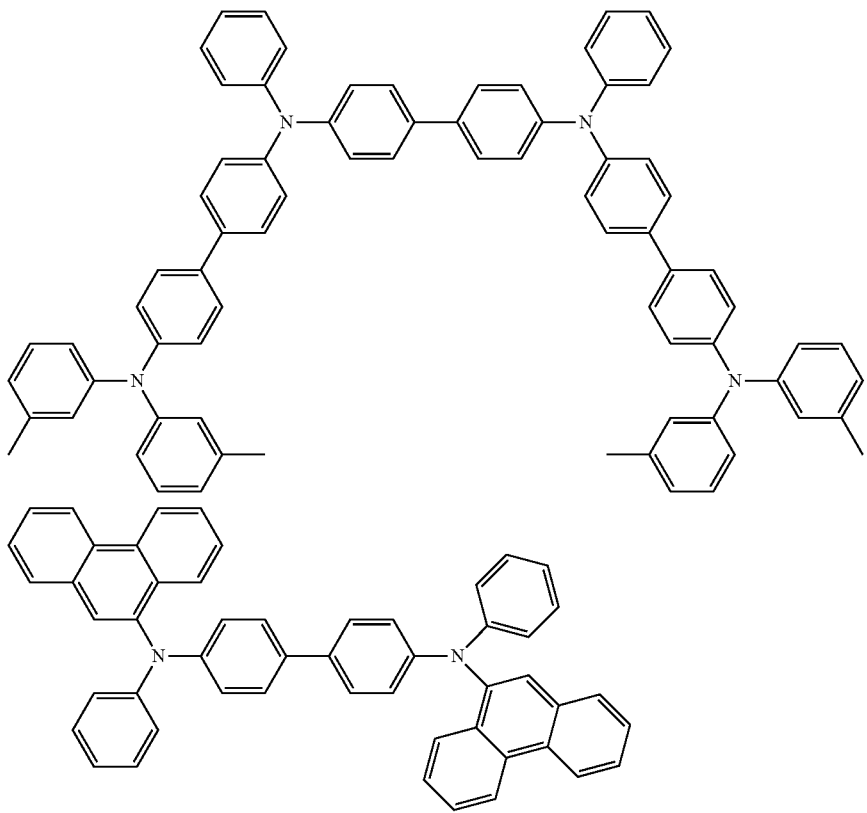

-continued
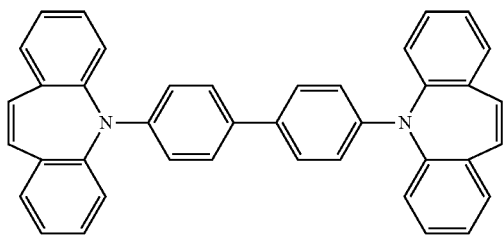
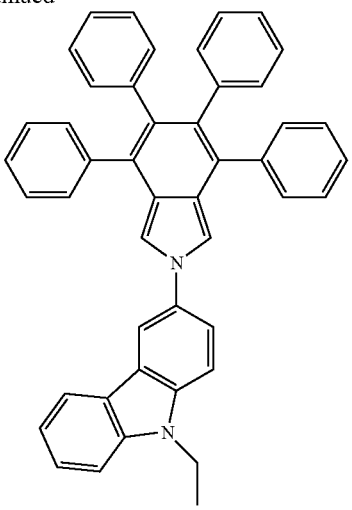
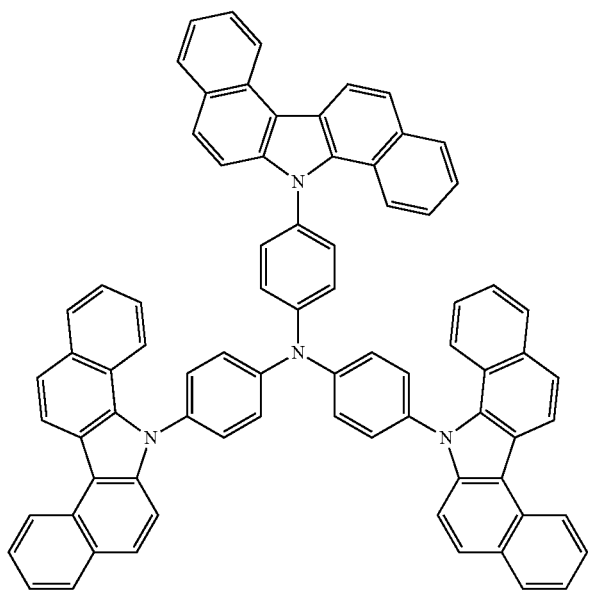
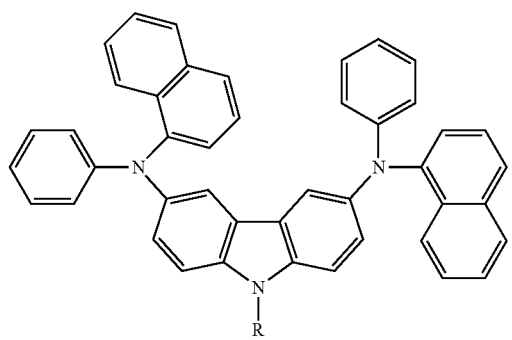
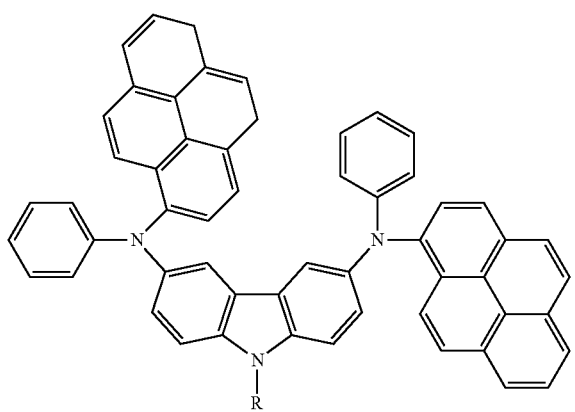

-continued
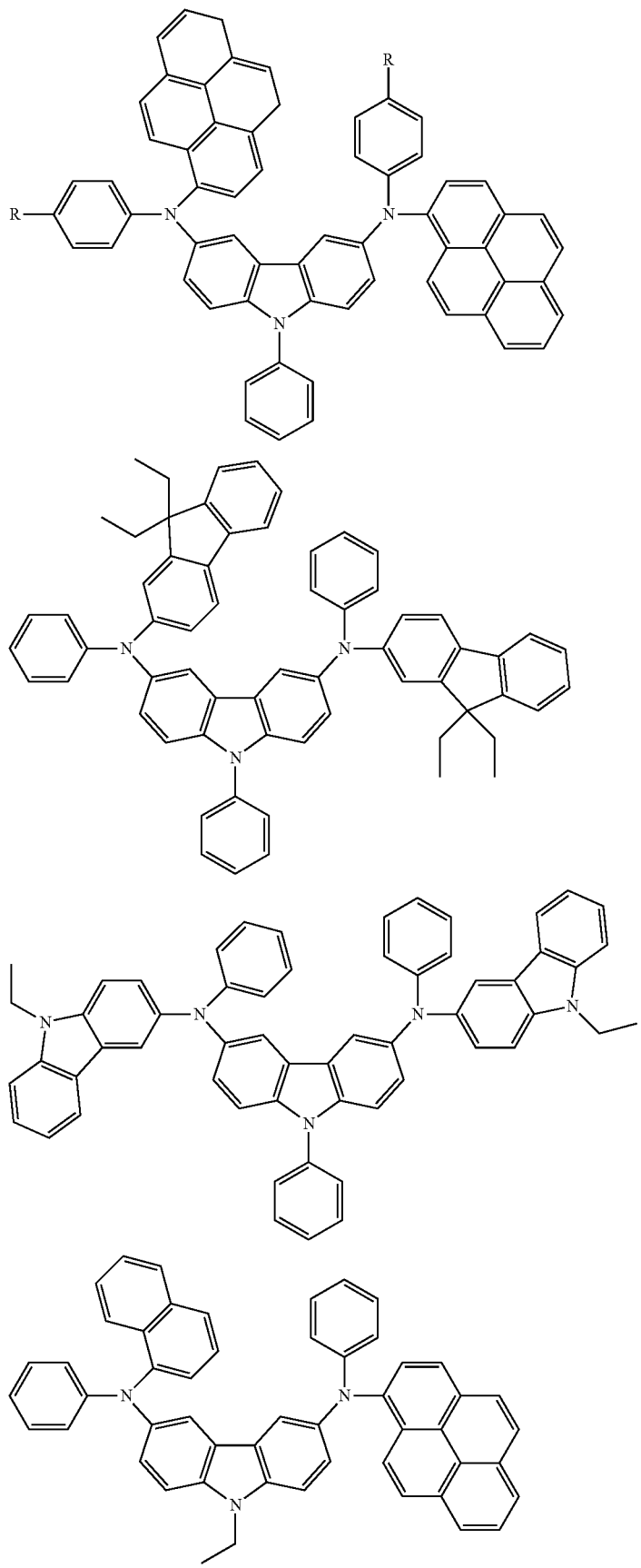

-continued
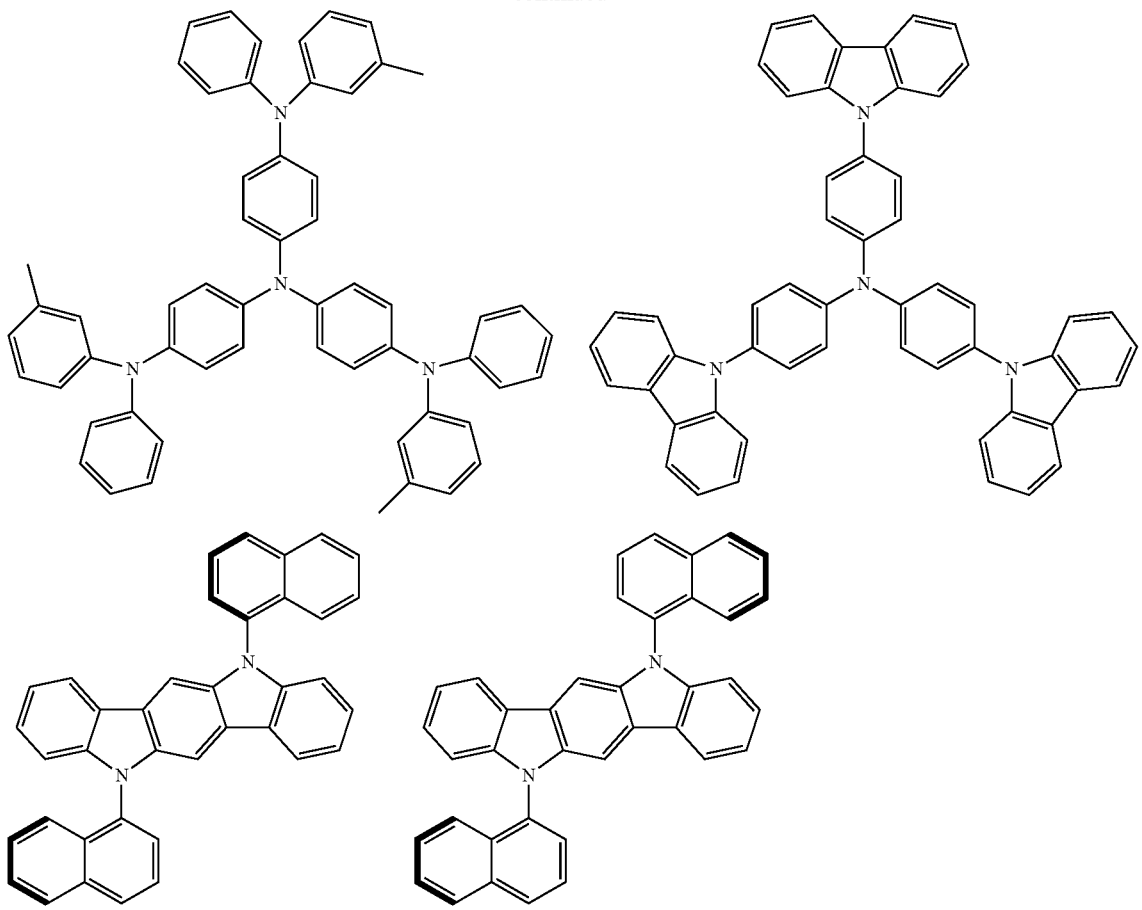
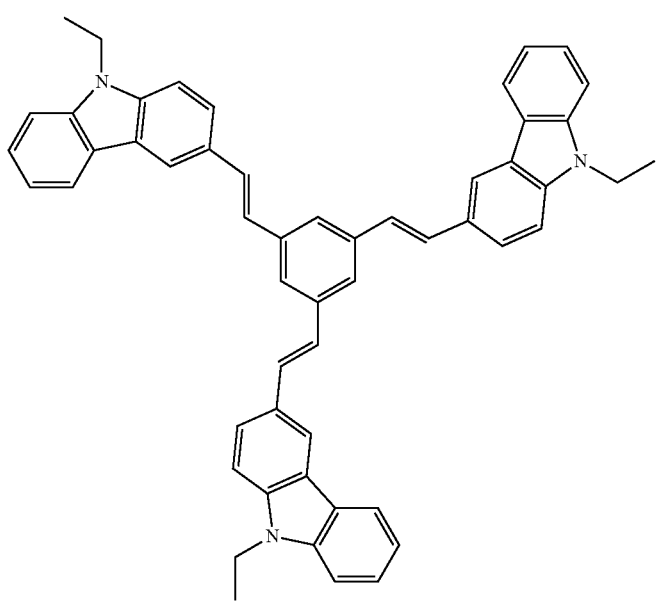

-continued
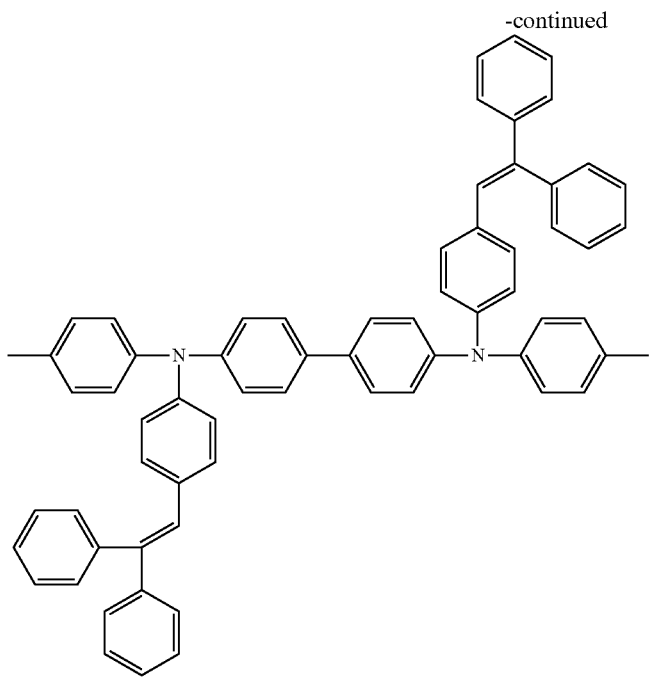
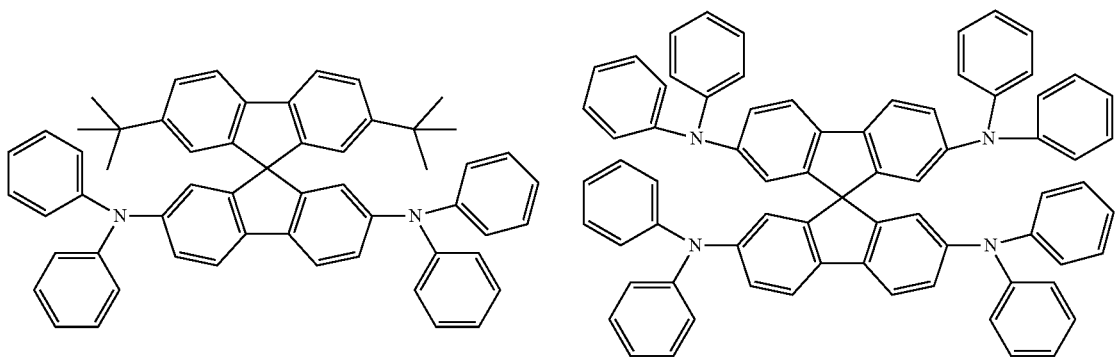
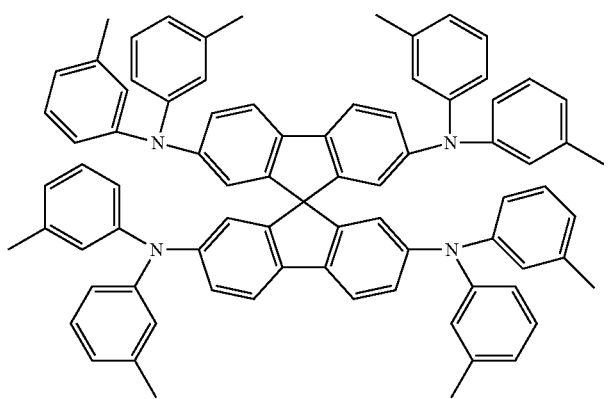

-continued
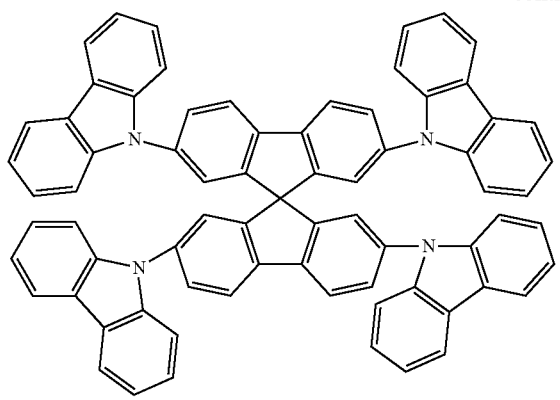
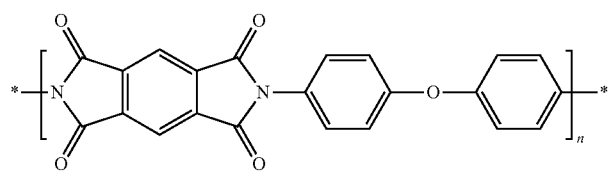
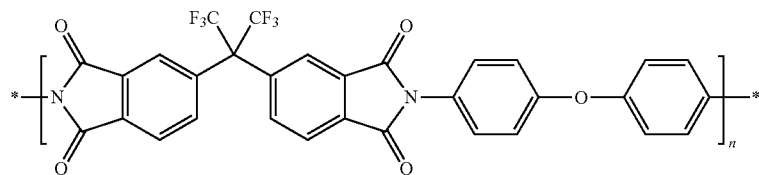
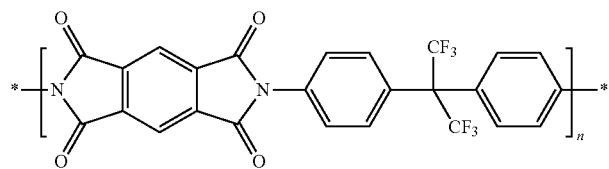
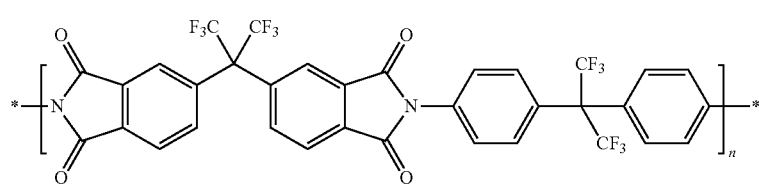
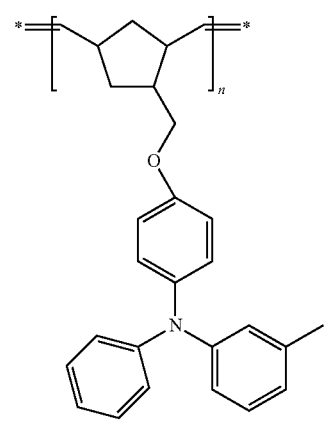

-continued
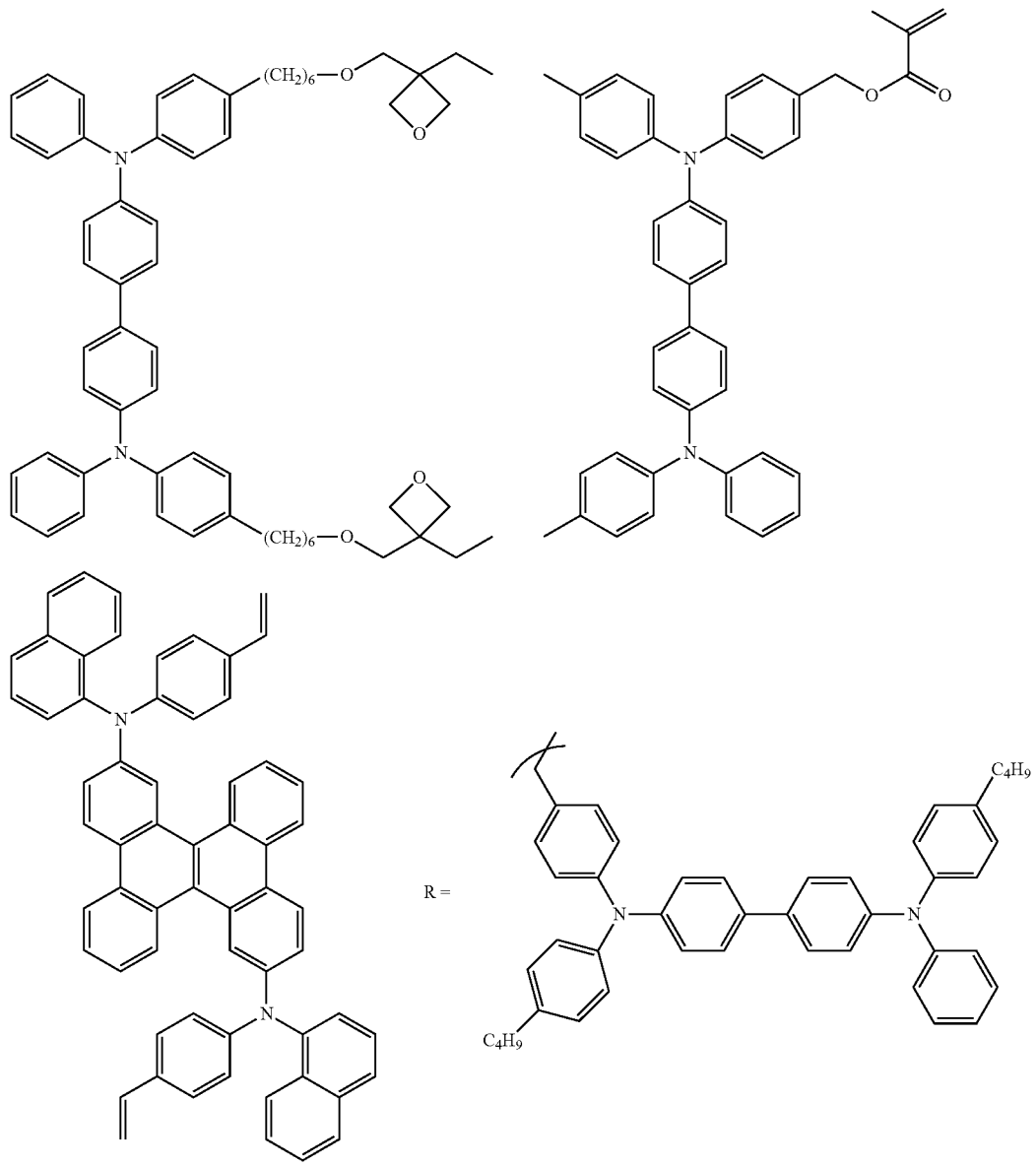
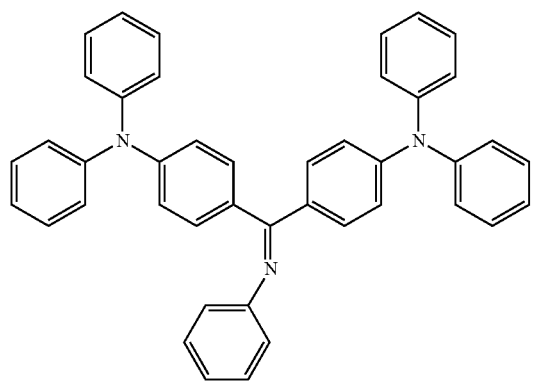

-continued
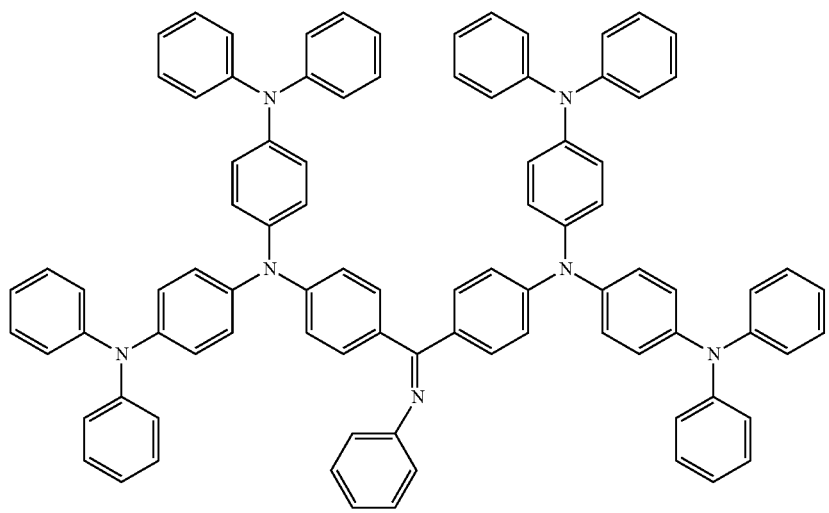
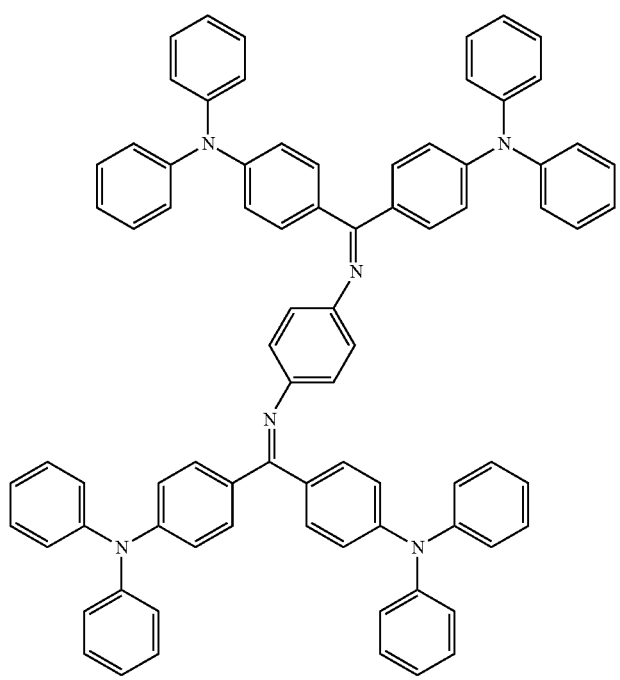

-continued
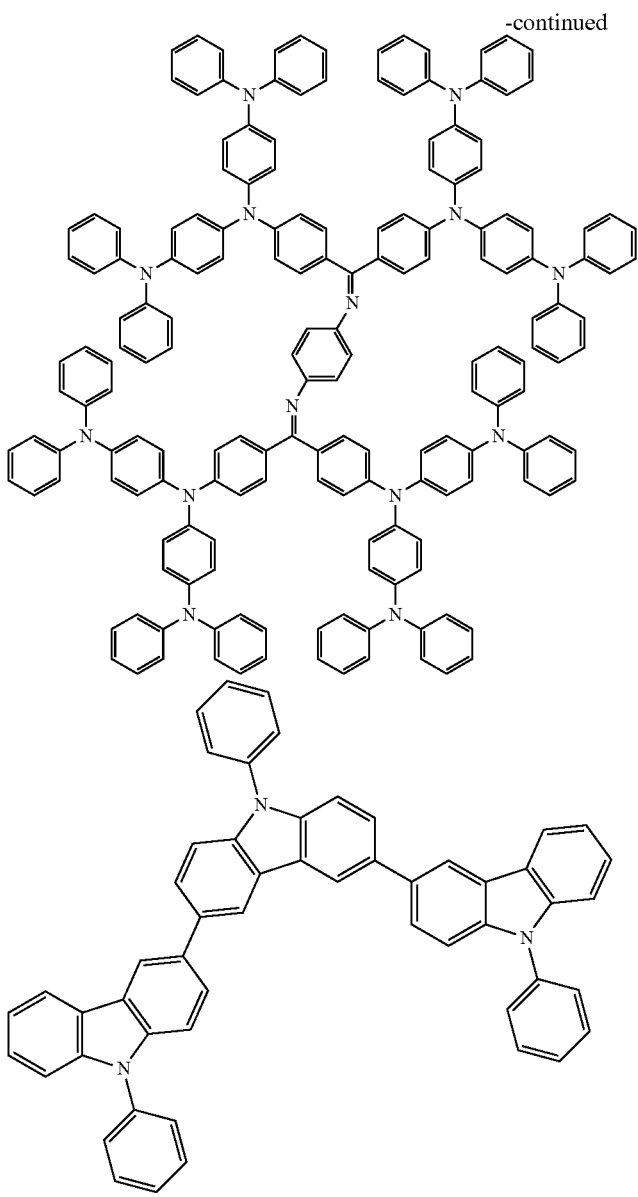
Preferred examples of a compound that may be used as the electron barrier material are shown below.
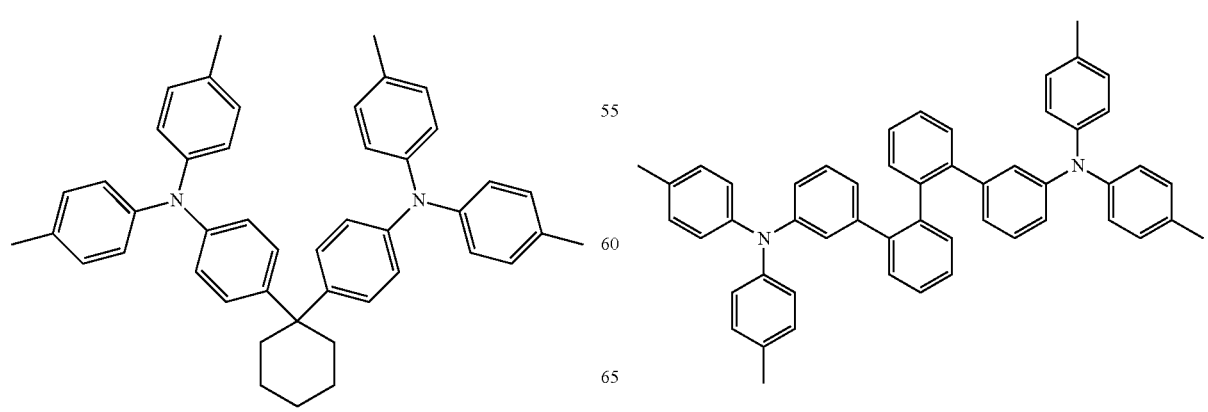
-continued

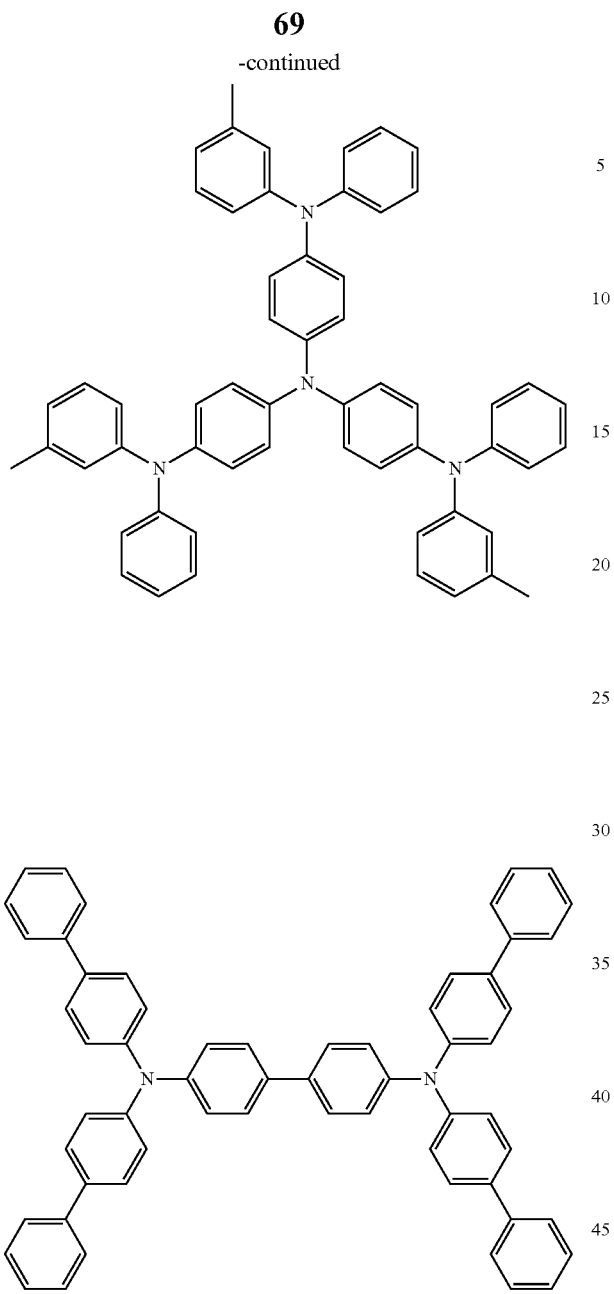
Preferred examples of a compound that may be used as the hole barrier material are shown below.
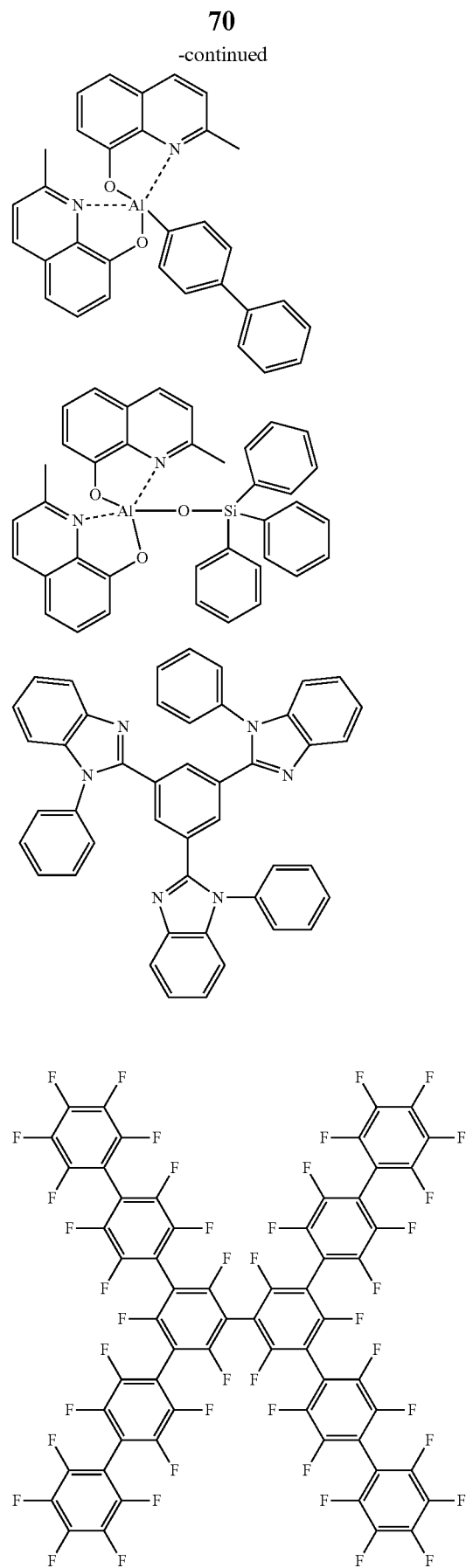

71
-continued
72
-continued
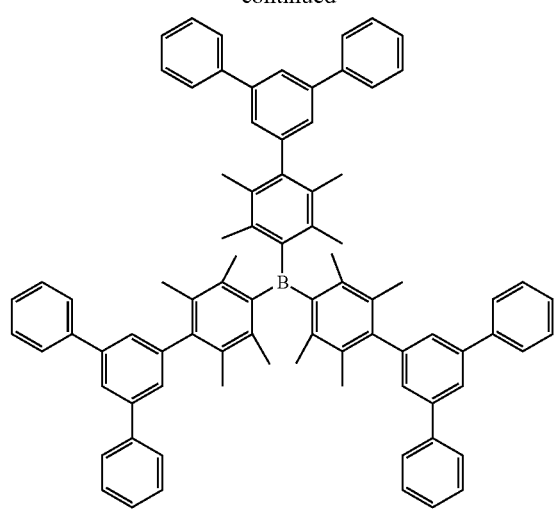
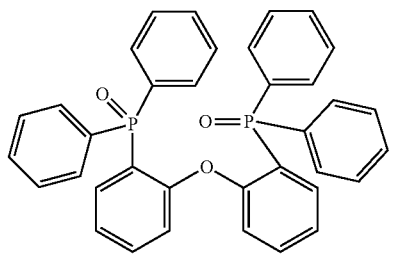
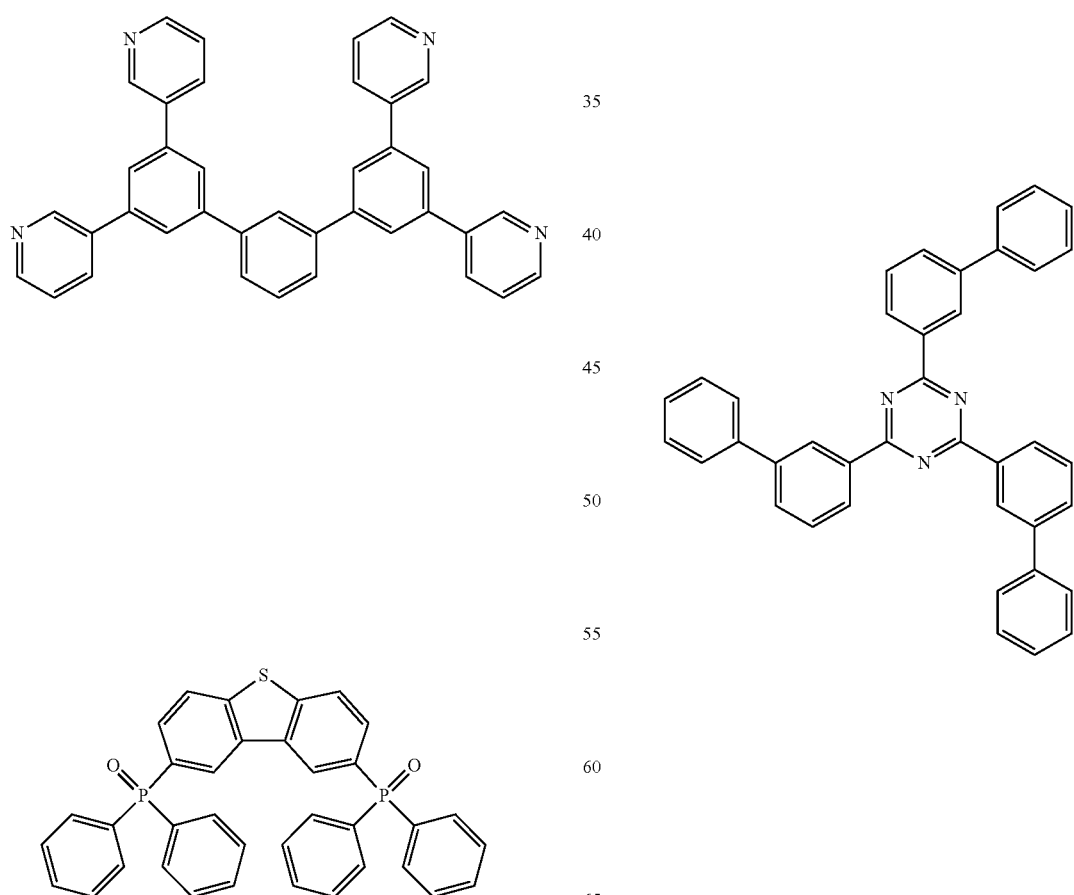
Preferred examples of a compound that may be used as the electron transporting material are shown below.

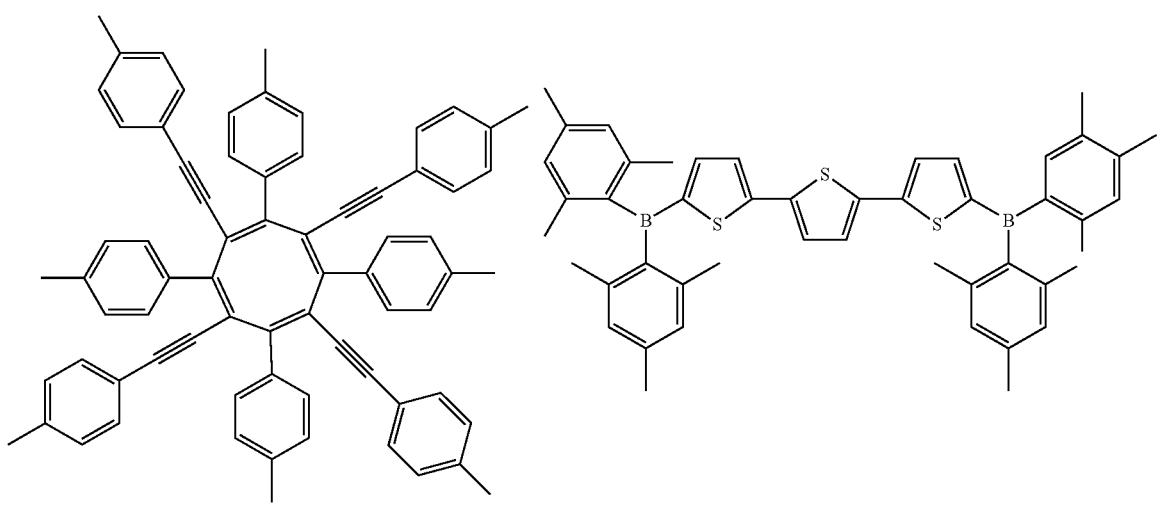
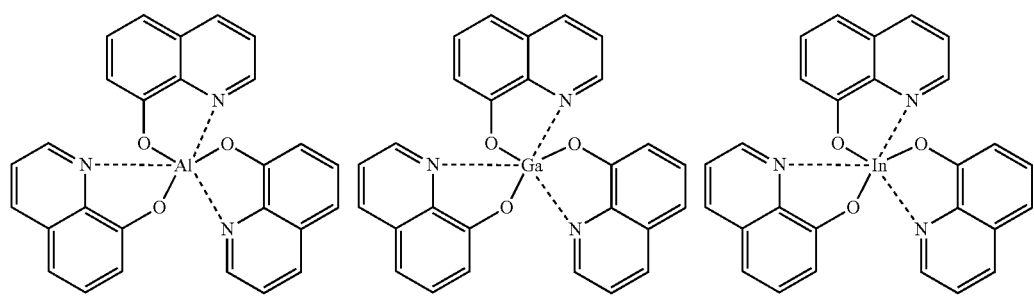
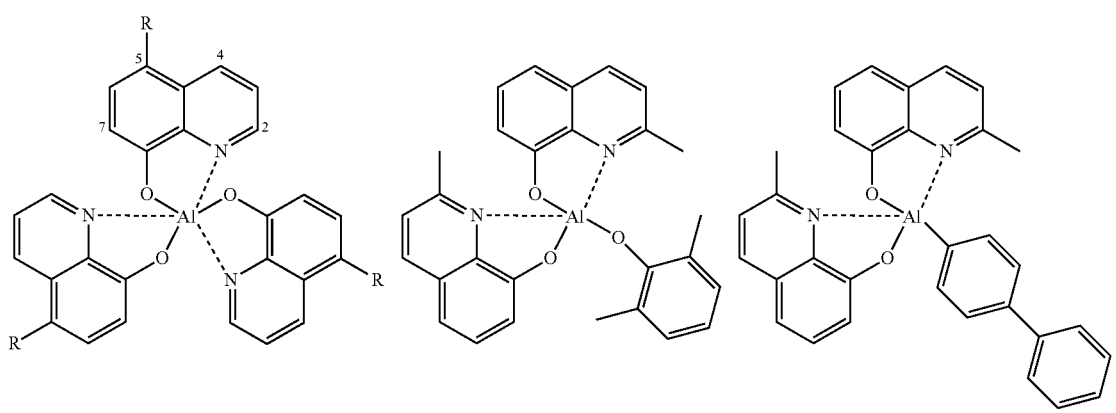
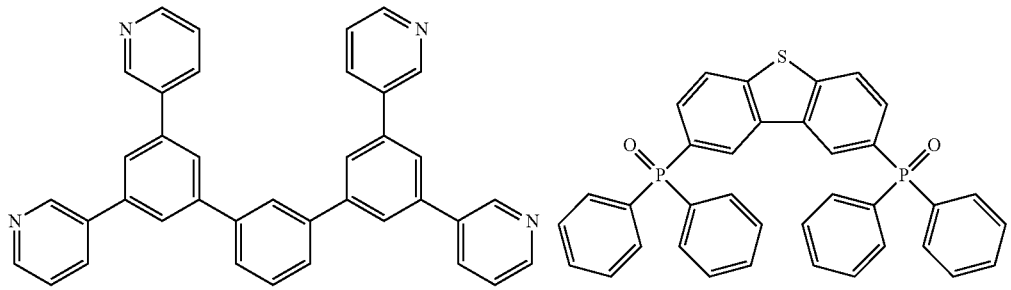

75
-continued
76
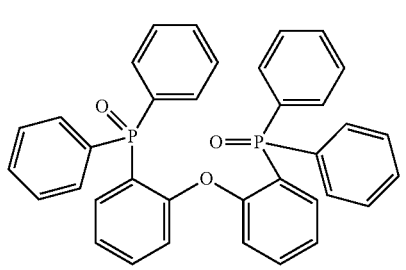 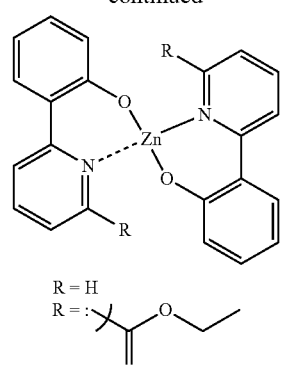 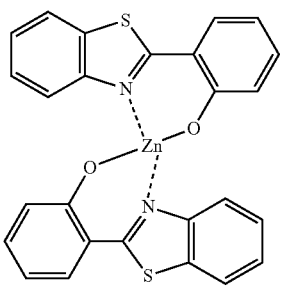
R = H
R = 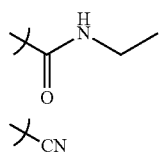
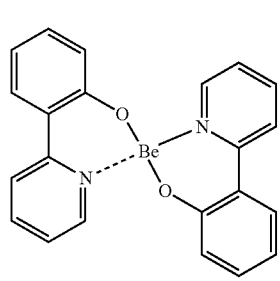 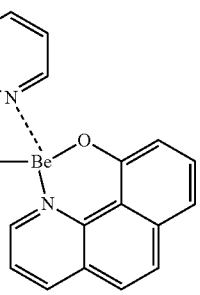 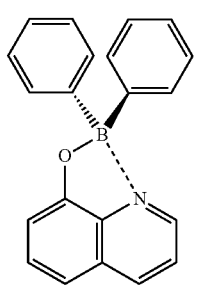
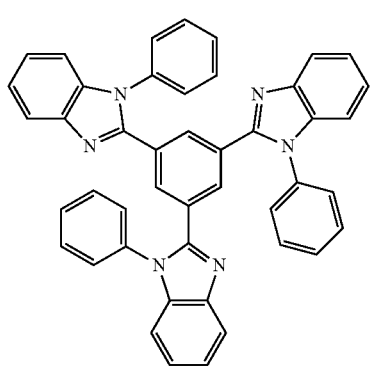 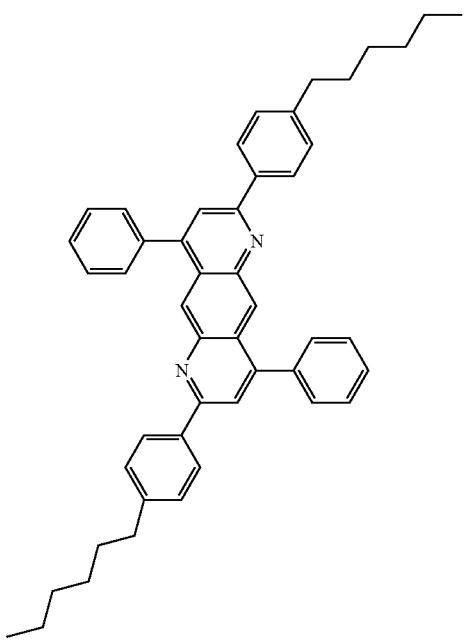

-continued
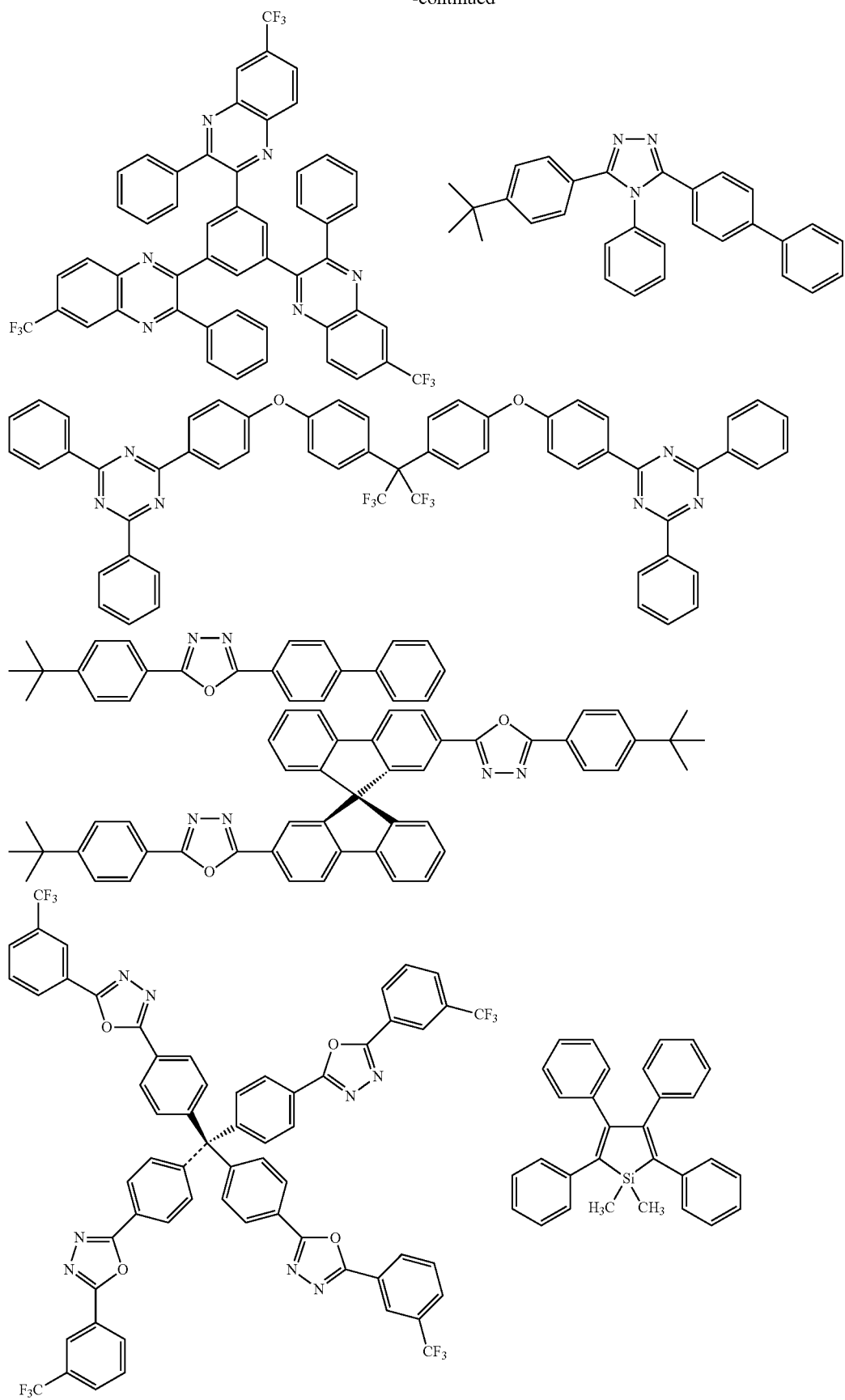

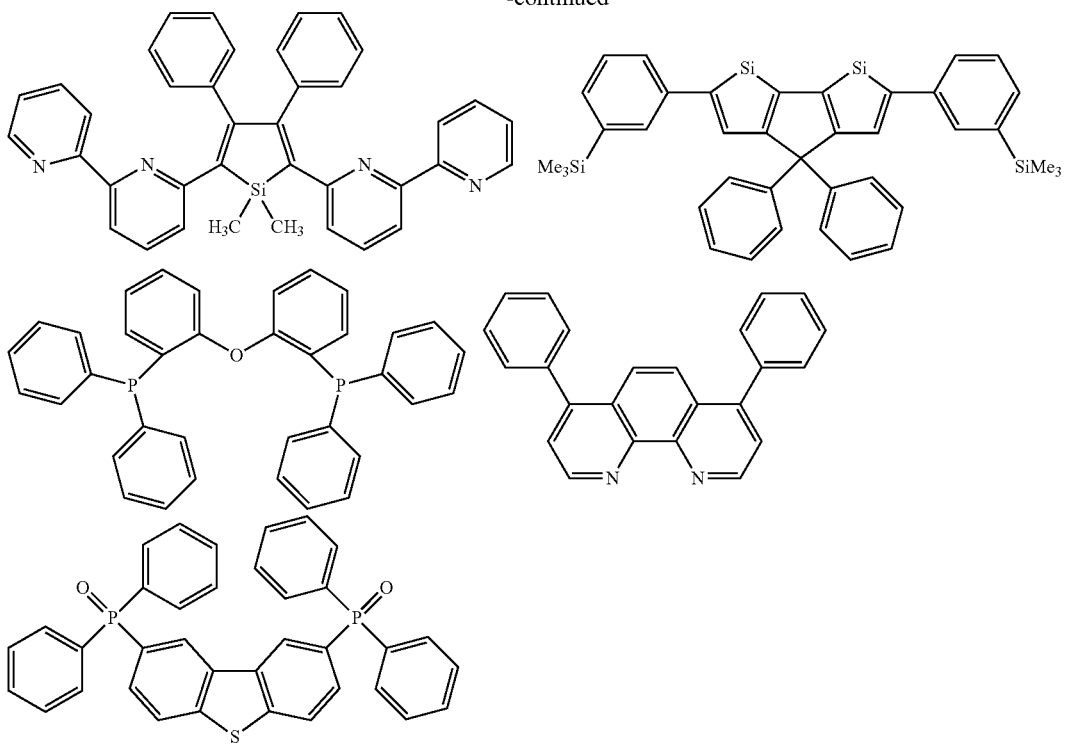
Preferred examples of a compound that may be used as the electron injection material are shown below.
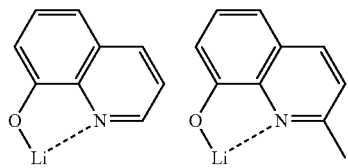
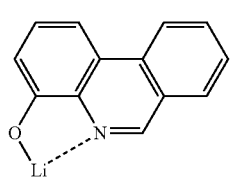
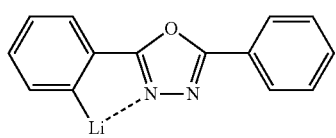
Preferred examples of a compound as a material that may be added are shown below. For example, the compound may be added as a stabilizing material.
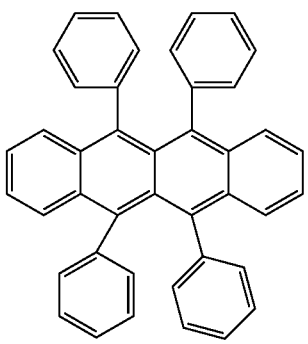
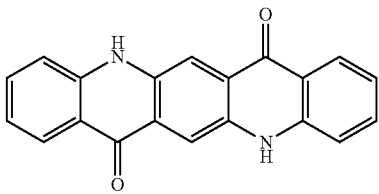

-continued

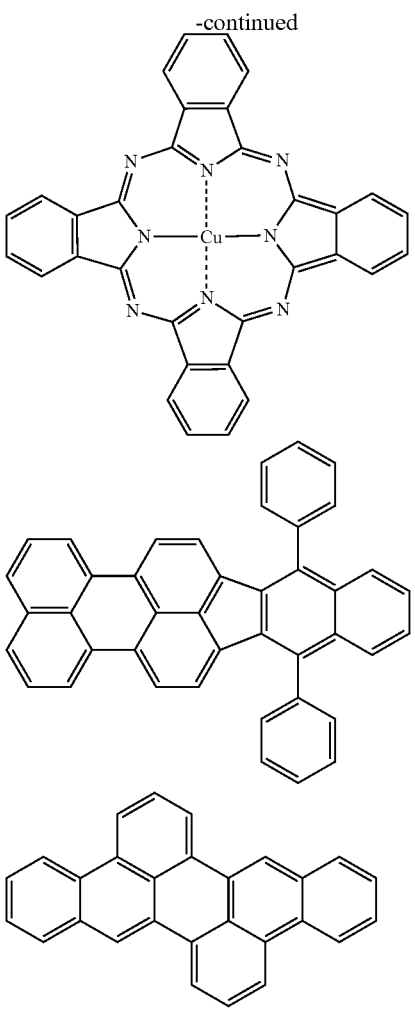

The organic electroluminescent device thus produced by the aforementioned method emits light on application of an electric field between the anode and the cathode of the device obtained. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light emitting device that is largely improved in light emission efficiency may be obtained by adding the organic metal complex represented by the general formula (1) in the light emitting layer. The organic light emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using a source meter (2400 Series, produced by Keithley Instruments Inc.), a semiconductor parameter analyzer (E5273A, produced by Agilent Technologies, Inc.), an optical power meter (1930C, produced by Newport Corporation), an optical spectrometer (USB2000, produced by Ocean Optics, Inc.), a spectroradiometer (SR-3, produced by Topcon Corporation), and a streak camera (Model C4334, produced by Hamamatsu Photonics K.K.).

Synthesis of Organic Metal Complexes

Synthesis Example 1

Synthesis of Compound 1

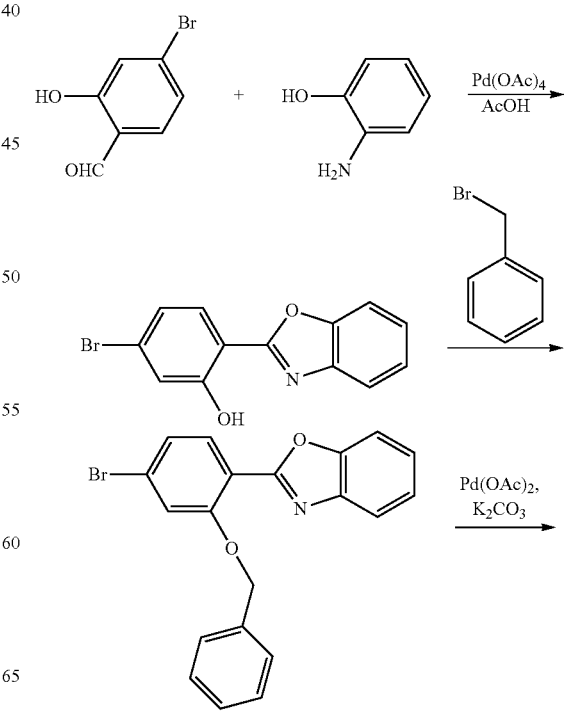

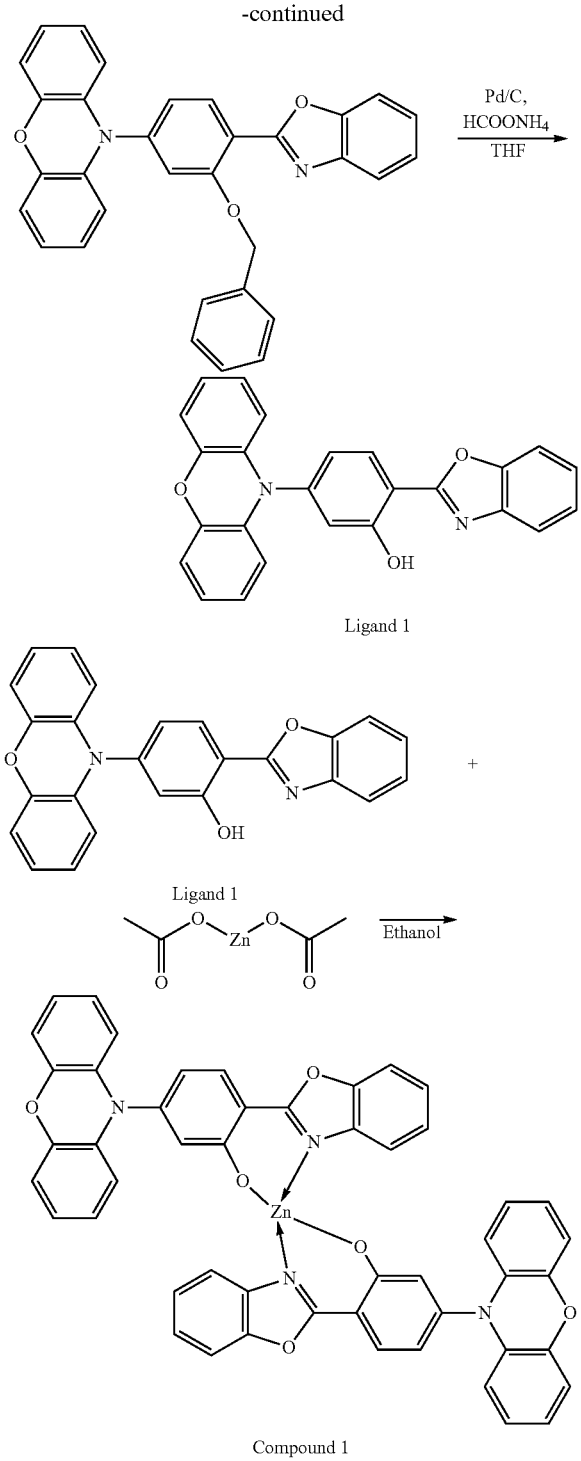

Scheme 1

Synthesis of 2-Benzoxazol-2-yl-4-bromophenol

4-Bromosalicylaldehyde (4.84 g, 24.1 mmol) and 2-aminophenol (3.15 g, 28.8 mmol) were added to acetic acid (120 mL). After stirring for 20 minutes, lead(IV) acetate (11.7 g, 26.4 mmol) was added, and the mixture was stirred for 1 hour and then stirred at 110° C. overnight. After cooling, the reaction mixture was placed in iced water, and neutralized with a sodium hydroxide aqueous solution. The precipitate thus obtained was filtered, and extracted with ethyl acetate. The product was purified by silica gel column chromatography (hexane/dichloromethane=70/30).

Yield amount: 3.25 g
Yield: 46.7%
$^1$H NMR (500 MHz, CDCl$_3$): δ (ppm) 11.6 (1H), 7.88 (d, J=8.5 Hz, 1H), 7.75-7.73 (m, 1H), 7.63-7.60 (m, 1H), 7.41-7.39 (m, 2H), 7.33 (d, J=2.0 Hz, 1H), 7.16 (dd, J=2.0 Hz, J=1.5 Hz, 1H)
MS: m/z=288 ([M−2]$^+$), 290 ([M]$^+$)

Scheme 2

Synthesis of 2-(2-(Benzyloxy)-4-bromophenyl)benzo[d]oxazole

A solution of 2-benzoxazol-2-yl-4-bromophenol (1.00 g, 3.46 mmol) and cesium carbonate (1.18 g, 3.63 mmol) in acetonitrile (17 mL) was stirred. Benzylbromide (0.42 mL, 3.53 mmol) was added to the solution, and the solution was stirred at 80° C. for 2.5 hours. After completing the reaction, the reaction mixture was extracted with dichloromethane. The organic layer obtained was rinsed with a 0.2 N sodium hydroxide aqueous solution and a sodium chloride aqueous solution. The organic layer was concentrated with an evaporator, and the resulting product was recrystallized from hexane.

Yield amount: 1.01 g
Yield: 76.5%
$^1$H NMR (500 MHz, CDCl$_3$): δ (ppm) 8.08 (d, J=8.0 Hz, 1H), 7.84-7.82 (m, 1H), 7.62-7.58 (m, 3H), 7.45-7.42 (m, 2H), 7.40-7.36 (m, 3H), 7.32-7.30 (m, 2H), 5.32 (s, 2H) MS: m/z=378 ([M−2]$^+$), 380 ([M]$^+$)

Scheme 3

Synthesis of 10-(4-(benzo[d]oxazol-2-yl)-3-(benzyloxy)phenyl)-10H-phenoxazine

A solution of 2-(2-(benzyloxy)-4-bromophenyl)benzo[d]oxazole (1.14 g, 3.00 mmol), phenoxazine (0.69 g, 3.75 mmol), palladium acetate (0.07 g, 0.30 mmol), and potassium carbonate (1.24 g, 9.00 mmol) in toluene (15 mL) was deaerated. Tri-tert-butylphosphine (2 M hexane solution, 0.55 mL, 1.10 mmol) was added to the solution, and the solution was refluxed under heating at 100° C. overnight. After completing the reaction, the reaction mixture was extracted with dichloromethane. The extract was concentrated with an evaporator, and then purified by medium pressure column chromatography (hexane/dichloromethane=50/50). The product was recrystallized from methanol/dichloromethane.

Yield amount: 1.36 g
Yield: 67.0%
$^1$H NMR (500 MHz, CDCl$_3$): δ (ppm) 8.39 (d, J=8.5 Hz, 1H), 7.86-7.84 (m, 1H), 7.63-7.61 (m, 1H), 7.54 (d, J=7.5 Hz, 2H), 7.41-7.36 (m, 4H), 7.33-7.30 (m, 1H), 7.12-7.10 (m, 2H), 6.73-6.66 (m, 4H), 6.62-6.58 (m, 2H), 5.97 (dd, J=1.0 Hz, J=1.0 Hz, 2H), 5.30 (s, 2H)+
MS: m/z=481 ([M−1]$^+$), 483 ([M+1]$^+$)

Scheme 4

Synthesis of 2-(Benzo[d]oxazol-2-yl)-5-(10H-phenoxazin-10-yl)phenol 10-(4-(Benzo[d]oxazol-2-yl)-3-(benzyloxy)phenyl)-10H-phenoxazine (3.02 g, 6.25 mmol) and 10% Pd/C (1.42 g, 13.5 mmol) were dissolved in tetrahydrofuran (220 mL), and the solution was stirred. An ammonium formate aqueous solution (7.63 g, 121.0 mmol, 9 mL) was added thereto, and the solution was stirred at 40° C. for 2.5 hours. The product recrystallized from hexane/dichloromethane.

Yield amount: 0.6384 g

Yield: 87.5%

$^1$H NMR (500 MHz, CDCl$_3$): δ (ppm) 11.67 (s, 1H), 8.25 (d, J=8.5 Hz, 1H), 7.79-7.77 (m, 1H), 7.67-7.65 (m, 1H), 7.44-7.42 (m, 2H), 7.16 (d, J=1.5 Hz, 1H), 7.02 (dd, J=1.5 Hz, J=2.0 Hz, 1H), 6.71-6.63 (m, 6H), 6.11 (d, J=6.5 Hz, 2H)

MS: m/z=391 ([M−1]$^+$), 394 ([M+2]$^+$)

Scheme 5

Synthesis of Compound 1

To a suspension solution of 2-(benzo[d]oxazol-2-yl)-5-(10H-phenoxazin-10-yl)phenol (0.89 g, 2.27 mmol) in ethanol (80 mL), zinc acetate dihydrate (0.25 g, 1.16 mmol) was added, and the mixture was heated to 70° C. under stirring for 3 days. After completing the reaction, the precipitate was filtered and rinsed with water and methanol.

Yield amount: 0.9113 g

Yield: 93.0%

MALDI-TOF-MS: m/z=846 ([M−2]$^+$), 848 ([M]$^+$)

Synthesis Example 2

Synthesis of Compound 2

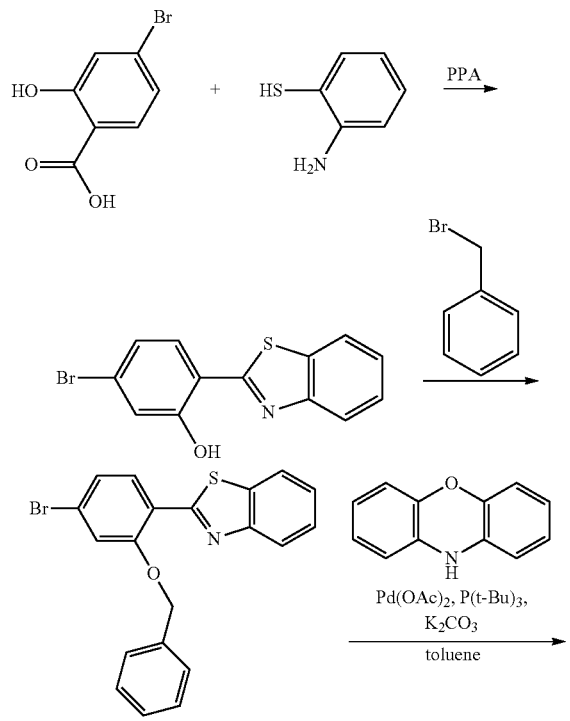

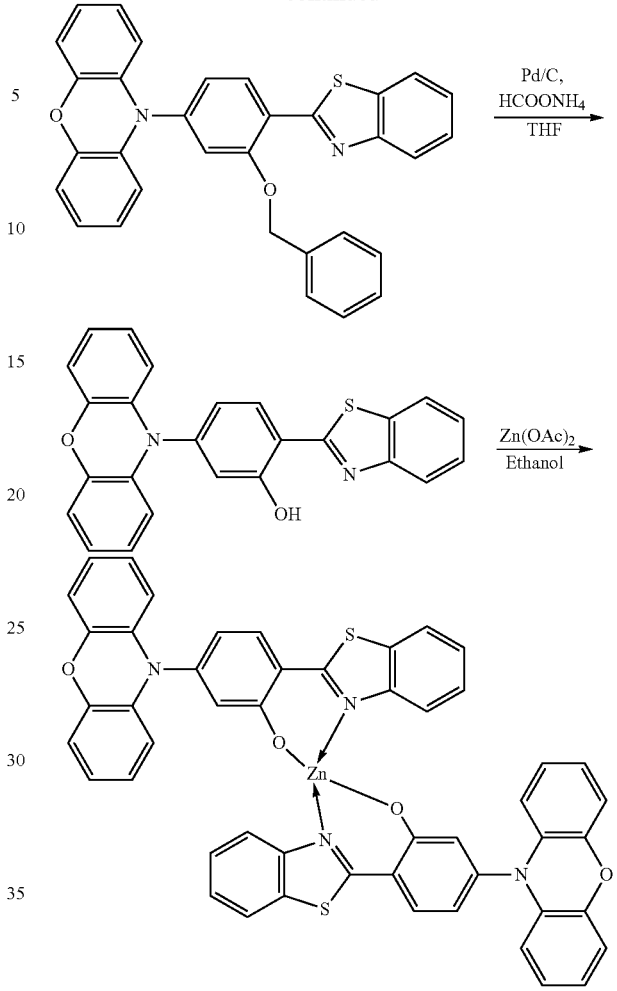

Compound 2

Scheme 1

Synthesis of 2-(Benzo[d]thiazol-2-yl)-5-bromophenol

4-Bromosalicylic acid (3.47 g, 16.0 mmol) and 2-aminothiophenol (2.00 g, 16.0 mmol) were added to polyphosphoric acid (PPA) (10 m), and the mixture was heated to 140° C. under stirring for 24 hours. After completing the reaction, the reaction mixture was cooled, and neutralized with a saturated sodium hydrogen carbonate aqueous solution. The precipitate was filtered and extracted with ethyl acetate. The extract was purified by silica gel column chromatography (chloroform/hexane=1/2).

Yield amount: 0.57 g

Yield: 46.8%

MS: m/z=306 ([M]$^+$), 308 ([M+2]$^+$)

Scheme 2

Synthesis of 2-(2-(Benzyloxy)-4-bromophenyl)benzo[d]thiazole

To a solution of 2-(benzo[d]thiazol-2-yl)-5-bromophenol (1.09 g, 3.55 mmol) and cesium carbonate (1.22 g, 3.73 mmol) in acetonitrile (17 mL), benzylbromide (0.62 g, 3.63 mmol) was added, and the mixture was reacted at 80° C. for 3 hours. After completing the reaction, the filtrate was extracted with dichloromethane, and the organic layer was rinsed with a 0.2 N sodium hydroxide aqueous solution and a sodium chloride aqueous solution. The organic layer was concentrated with an evaporator, and the resulting product was purified by silica gel column chromatography (hexane/dichloromethane=70/30).

Yield amount: 1.14 g
Yield: 80.8%
MS: m/z=395 ([M−1]$^+$)

Scheme 3

Synthesis of 10-(4-(benzo[d]triazol-2-yl)-3-(benzyloxy)phenol)-10H-phenoxazine

A solution of 2-(2-(benzyloxy)-4-bromophenyl)benzo[d]thiazole (1.19 g, 3.00 mmol), phenoxazine (0.69 g, 3.75 mmol), palladium acetate (0.07 g, 0.30 mmol), and potassium carbonate (1.24 g, 9.00 mmol) in toluene (15 mL) was deaerated. Tri-tert-butylphosphine (2 M hexane solution, 0.55 mL, 1.10 mmol) was added to the solution, and the solution was refluxed under heating at 100° C. overnight. After completing the reaction, the reaction mixture was extracted with dichloromethane. The extract was concentrated with an evaporator, and then purified by medium pressure column chromatography (hexane/dichloromethane=50/50). The product was recrystallized from methanol/dichloromethane.

Yield amount: 1.17 g
Yield: 78.2%
MS: m/z=498 ([M]$^+$)

Scheme 4

Synthesis of 2-(Benzo[d]thiazol-2-yl)-5-(10H-phenoxazin-10-yl)phenol 10-(4-(Benzo[d]thiazol-2-yl)-3-(benzyloxy)phenyl)-10H-phenoxazine (0.77 g, 1.54 mmol) and 10% Pd/C (0.35 g, 0.33 mmol) were dissolved in tetrahydrofuran (55 mL), and the solution was stirred. An ammonium formate aqueous solution (0.19 g, 3.00 mmol, 2 mL) was added thereto, and the solution was stirred at 40° C. for 3 hours. The product recrystallized from hexane/dichloromethane.

Yield amount: 0.50 g
Yield: 80.5%
MS: m/z=408 ([M]$^+$)

Scheme 5

Synthesis of Compound 2

To a suspension solution of 2-(benzo[d]thiazol-2-yl)-5-(10H-phenoxazin-10-yl)phenol (0.41 g, 1.00 mmol) in ethanol (40 mL), zinc acetate dihydrate (0.11 g, 0.51 mmol) was added, and the mixture was heated to 70° C. under stirring overnight. After completing the reaction, the precipitate was filtered and rinsed with water and methanol.

Yield amount: 0.34 g
Yield: 77.4%
MALDI-TOF-MS: m/z=878 ([M−2]$^+$), 880 ([M]$^+$)

Synthesis Example 3

Synthesis of Compound 3

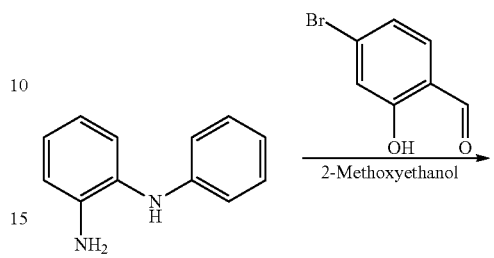

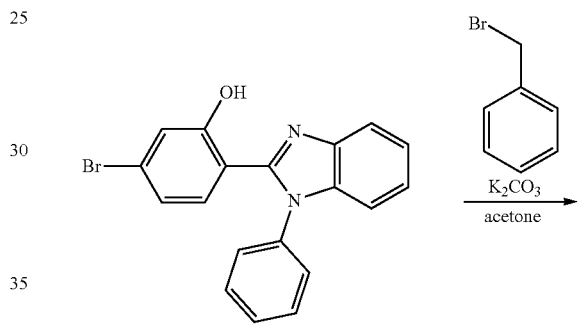

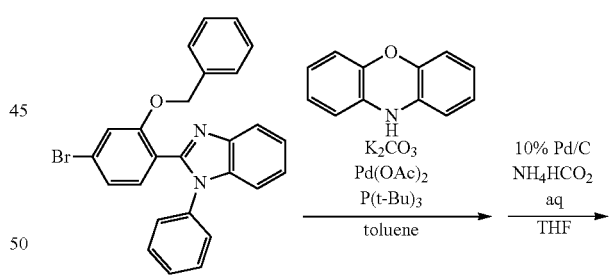

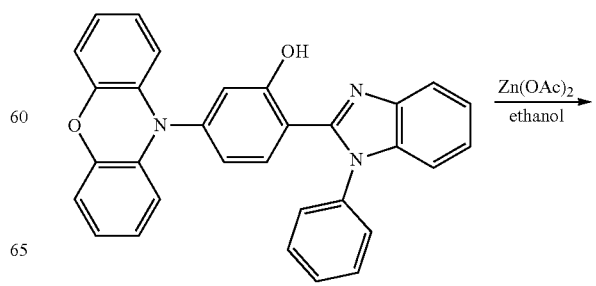

-continued

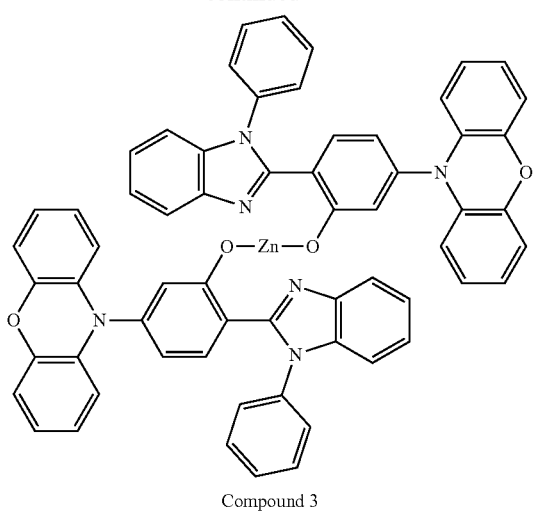

Compound 3

Scheme 1

Synthesis of 5-Bromo-2-(1-phenyl-1H-benzo[d]imidazol-2-yl)phenol

4-Bromo-2-hydroxybenzaldehyde (5.25 g, 26.3 mmol) and N-phenyl-1,2-phenylenediamine (4.81 g, 26.1 mmol) were weighed in a reaction vessel, to which 150 mL of 2-methoxyethanol was added, and the mixture was stirred at 125° C. for 38 hours. The reaction solution was cooled to room temperature, and then the solvent was distilled off under reduced pressure. The resulting solid matter was rinsed with methanol and then dried, thereby providing 4.68 g of white powder 1.

Yield: 49.1%

$^1$H NMR (500 MHz, CDCl$_3$): δ (ppm) 13.83 (b, 1H, O$\underline{H}$), 7.81 (d, 1H, J=8.1 Hz, Ar$\underline{H}$), 7.64-7.61 (m, 3H, Ar$\underline{H}$), 7.42-7.40 (m, 2H, Ar$\underline{H}$), 7.36 (dt, 1H, J$_{ortho}$=7.6 Hz, J$_{meta}$=1.1 Hz, Ar$\underline{H}$), 7.29 (m, 2H, Ar$\underline{H}$), 7.09 (d, 1H, J=8.1 Hz, Ar$\underline{H}$), 6.67 (s, 1H, Ar$\underline{H}$) ppm Scheme 2

Synthesis of 2-(2-(Benzyloxy)-4-bromophenyl)-1-phenyl-1H-benzo[d]imidazole

5-Bromo-2-(1-phenyl-1H-benzo[d]imidazol-2-yl)phenol (4.68 g, 12.9 mmol), potassium carbonate (4.42 g, 32.0 mmol), and benzyl bromide (1.75 mL, 14.8 mmol) were weighed in a reaction vessel, to which 100 mL of acetone was added, and the mixture was stirred in a nitrogen atmosphere at 60° C. for 8 hours. The reaction solution was cooled to room temperature and then filtered, and the solution was distilled off under reduced pressure. Methylene chloride was added to the resulting residue, the mixture was rinsed with water, and the organic layer was dried over anhydrous sodium sulfate. The organic layer was filtered, and the solvent was distilled off under reduced pressure to provide a solid matter, which was dissolved in a small amount of methylene chloride and reprecipitated by adding n-hexane thereto. The solid matter thus deposited was filtered to provide 5.38 g of yellowish white powder.

Yield: 92.3%

$^1$H NMR (500 MHz, CDCl$_3$): δ (ppm) 7.89 (d, 1H, J=8.0 Hz, Ar$\underline{H}$), 7.57 (d, 1H, J=8.1 Hz, Ar$\underline{H}$), 7.35-(m, 10H, Ar$\underline{H}$), 7.07-7.05 (m, 2H, Ar$\underline{H}$), 6.98-6.96 (m, 2H, Ar$\underline{H}$), 6.91 (d, 1H, J$_{meta}$=1.7 Hz, Ar$\underline{H}$), 4.65 (s, 2H, —C$\underline{H}_2$—) ppm Scheme 3

Synthesis of 5-(10H-phenoxazin-10-yl)-2-(1-phenyl-1H-benzo[d]imidazol-2-yl)phenol 2-(2-(Benzyloxy)-4-bromophenyl)-1-phenyl-1H-benzo[d]imidazole (0.91 g, 2.00 mmol), 10H-phenoxazine (0.39 g, 2.82 mmol), potassium carbonate (0.83 g, 6.01 mmol), palladium(II) acetate (0.045 g, 0.200 mmol), tri-tert-butylphosphine (0.12 g, 0.593 mmol), and 15 mL of toluene were placed in a reaction vessel. The solution was deaerated, and then stirred under a light-shielded nitrogen atmosphere at 110° C. for 19 hours. The reaction solution was cooled to room temperature and then filtered, and the solvent was distilled off under reduced pressure. Methylene chloride was added to the resulting residue, the mixture was rinsed with water, and the organic layer was dried over anhydrous sodium sulfate. The solvent was distilled off under reduced pressure to provide a crude product. After removing 10H-phenoxazine from the crude product by column chromatograph (support: SiO$_2$, eluent: methylene chloride), the product was eluted with ethyl acetate, and a compound in the form of a brown oily matter was obtained by distillation under reduced pressure.

The resulting oily product, 0.56 g of 10% palladium-carbon, 3 mL of a 7 M ammonium formate aqueous solution, and 70 mL of tetrahydrofuran were placed in a reaction vessel, and the mixture was stirred in a nitrogen atmosphere at 40° C. for 4 hours, and then cooled to room temperature. The solvent was distilled off under reduced pressure. Methylene chloride was added to the resulting residue and rinsed with water, and the organic layer was dried over anhydrous sodium sulfate. The solvent was distilled off under reduced pressure to provide a crude product, which was dissolved in a small amount of methylene chloride and reprecipitated by adding n-hexane thereto. The solid matter thus deposited was filtered to provide 0.66 g of a compound in the form of yellowish white powder.

Yield: 70.9%

$^1$H NMR (500 MHz, CDCl$_3$): δ (ppm) 14.05 (b, 1H, O$\underline{H}$), 7.85 (d, 1H, J=8.0 Hz, Ar$\underline{H}$), 7.66-7.63 (m, 3H, Ar$\underline{H}$), 7.49-7.47 (m, 2H, ArH), 7.38 (dt, 1H, J$_{ortho}$=7.7 HZ, J$_{meta}$=1.1 Hz, Ar$\underline{H}$), 7.31 (dt, 1H, J$_{ortho}$=7.7 Hz, J$_{meta}$=1.0 Hz, Ar$\underline{H}$), 7.12-7.11 (m, 2H, Ar$\underline{H}$), 7.05 (m, 1H, Ar$\underline{H}$), 6.68-6.58 (m, 6H, Ar$\underline{H}$), 6.50 (dd, 1H, J$_{ortho}$=8.6 HZ, J$_{meta}$=2.2 Hz, Ar$\underline{H}$), 6.05 (dd, J$_{ortho}$=7.7 HZ, J$_{meta}$=1.5 Hz, Ar$\underline{H}$) ppm Scheme 4

Synthesis of Compound 3

5-(10H-phenoxazin-10-yl)-2-(1-phenyl-1H-benzo[d]imidazol-2-yl)phenol (0.612 g, 1.31 mmol), zinc acetate dihydrate (0.128 g, 0.587 mmol), and 70 mL of ethanol were placed in a reaction vessel, and the mixture was stirred in a nitrogen atmosphere at 70° C. for 15 hours. After cooling the reaction solution to room temperature, 200 mL of ultrapure water was added to the reaction solution, which was stirred and then filtered, and the product was dried for 1 day and subjected to sublimation purification, thereby providing 0.231 g of a compound in the form of yellow powder (yield:

35.3%). The sublimation purification was performed by using a sublimation purification equipment (P-100 MK III, Organic Device Raw Material Purification Equipment, produced by ALS Technology Co., Ltd.).

The resulting powder was identified for the structure thereof by using a matrix-assisted laser desorption ionization time of flight mass spectrometer (AXIMA-CFR Plus, produced by Shimadzu Corporation) and an elemental analyzer (Yanaco CHN Corder Type MT-5, produced by Yanagimoto Seisakusho Co., Ltd.).

Anal Calc for $C_{62}H_{40}N_6O_4Zn$: C, 74.60; H, 3.95; N, 8.39
Found: C, 74.59; H, 4.04; N, 8.42
MS: (m/z)=997.61 $[M+H]^+$ Synthesis Example 4

Synthesis of Compound 13

Compound 13

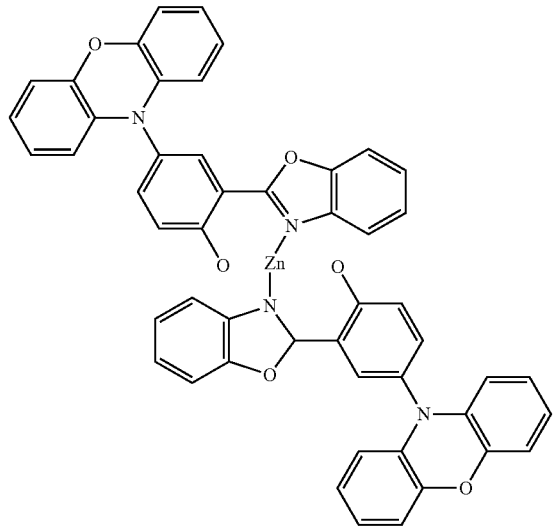

The compound 13 was synthesized in the same manner as in Synthesis Example 1 except that 5-bromo-2-hydroxybenzaldehyde was used instead of 4-bromo-2-hydroxybenzaldehyde.

The production of the target product was confirmed by MALDI-TOF-MS.
m/z=848 $[M]^+$ Synthesis Example 5

Synthesis of Compound 25

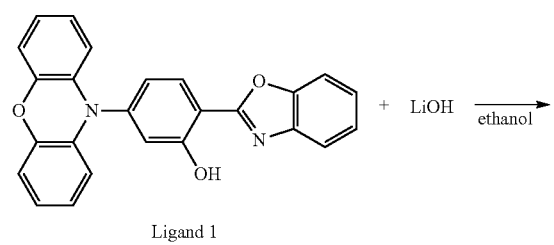

Ligand 1

-continued

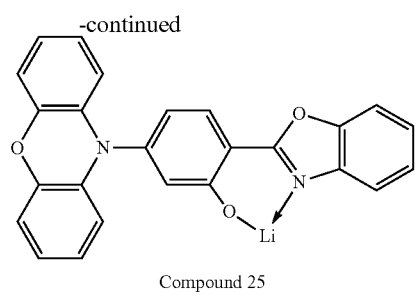

Compound 25

The ligand 1 was synthesized in the same manner as in Synthesis Example 1. The ligand 1 and lithium hydroxide were dissolved in ethanol, and the mixture was stirred to provide the compound 25.

The production of the target product was confirmed by MALDI-TOF-MS.
m/z=398 $[M]^+$ Synthesis Example 6

Synthesis of Compound 51

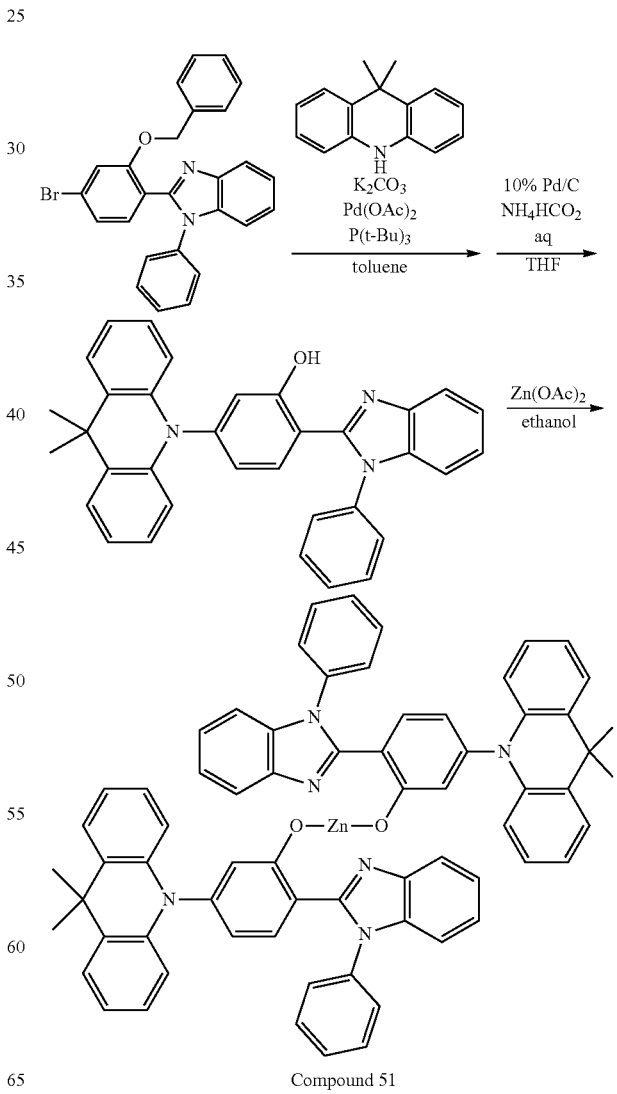

Compound 51

Scheme 1

Synthesis of 5-(9,9-Dimethylacridin-10(9H)-yl)-2-(1-phenyl-1H-benzo[d]imidazol-2-yl)phenol 2-(2-(Benzyloxy)-4-bromophenyl)-1-phenyl-1H-benzo[d]imidazole (2.50 g, 5.50 mmol), 9,9-dimethyl-9,10-dihydroacridine (1.26 g, 6.03 mmol), potassium carbonate (2.28 g, 16.5 mmol), palladium(II) acetate (0.112 g, 0.500 mmol), tri-tert-butylphosphine (0.33 g, 1.63 mmol), and 30 mL of toluene were placed in a reaction vessel. The solution was deaerated, and then stirred under a light-shielded nitrogen atmosphere at 110° C. for 40 hours. The reaction solution was cooled to room temperature and then filtered, and the solvent was distilled off under reduced pressure. Methylene chloride was added to the resulting residue, the mixture was rinsed with water, and the organic layer was dried over anhydrous sodium sulfate. The solvent was distilled off under reduced pressure to provide a crude product. After removing 9,9-dimethyl-9,10-dihydroacridine from the crude product by column chromatograph (support: $SiO_2$, eluent: methylene chloride), the product was eluted with ethyl acetate, and a compound in the form of a brown oily matter was obtained by distilling off the solvent under reduced pressure.

The resulting oily product, 1.0 g of 10% palladium-carbon, 7.8 mL of a 7 M ammonium formate aqueous solution, and 100 mL of tetrahydrofuran were placed in a reaction vessel, and the mixture was stirred in a nitrogen atmosphere at 40° C. for 9 hours, and then cooled to room temperature. The solvent was distilled off under reduced pressure. Methylene chloride was added to the resulting residue and rinsed with water, and the organic layer was dried over anhydrous sodium sulfate. The solvent was distilled off under reduced pressure to provide a crude product, which was dissolved in a small amount of methylene chloride and reprecipitated by adding n-hexane thereto. The solid matter thus deposited was filtered to provide 2.08 g of 5-(9,9-dimethylacridin-10(9H)-yl)-2-(1-phenyl-1H-benzo[d]imidazol-2-yl)phenol in the form of yellowish white powder (yield: 74.2%).

$^1$H NMR (500 MHz, $CDCl_3$): δ (ppm) 14.01 (b, 1H, OH), 7.65 (d, 1H, J=8.1 Hz, ArH), 7.68-7.61 (m, 3H, ArH), 7.51-7.49 (m, 2H, ArH), 7.42 (dd, 2H, $J_{ortho}$=7.7 Hz, $J_{meta}$=1.6 Hz, ArH), 7.39 (dt, 1H, $J_{ortho}$=7.7 Hz, $J_{meta}$=1.1 Hz, ArH), 7.31 (dt, 1H, $J_{ortho}$=7.7 HZ, $J_{meta}$=1.1 HZ, ArH), 7.13 (d, 1H, $J_{meta}$=2.1 Hz, ArH), 7.11 (d, 1H, J=8.1 Hz, Ar H), 7.07 (d, 1H, J=8.5 Hz, ArH), 6.97 (dt, 2H, $J_{ortho}$=7.7 Hz, $J_{meta}$=1.6 Hz ArH), 6.92 (dt, 2H, $J_{ortho}$=7.4 Hz, $J_{meta}$=1.3 Hz ArH), 6.50 (dd, 1H, $J_{ortho}$=8.5 Hz, $J_{meta}$=2.1 Hz, ArH), 6.42 (dd, 2H, $J_{ortho}$=8.2 Hz, $J_{meta}$=1.2 Hz, ArH), 1.64 (s, 6H, CH) ppm

Scheme 2

Synthesis of Compound 51

5-(9,9-Dimethylacridin-10(9H)-yl)-2-(1-phenyl-H-benzo[d]imidazol-2-yl)phenol (0.690 g, 1.40 mmol), zinc acetate dihydrate (0.140 g, 0.640 mmol), and 70 mL of ethanol were placed in a reaction vessel, and the mixture was stirred in a nitrogen atmosphere at 70° C. for 22 hours, and then cooled to room temperature. 200 mL of ultrapure water was added to the reaction solution, which was stirred and then filtered, and the product was dried for 1 day and subjected to sublimation purification, thereby providing 0.366 g of the compound 51 in the form of yellow powder (yield: 54.8%).

The resulting powder was identified for the structure thereof by using the matrix-assisted laser desorption ionization time of flight mass spectrometer and the elemental analyzer.

Anal Calc for $C_{68}H_{52}N_6O_2Zn$: C, 77.74; H, 4.99; N, 8.00
Found: C, 77.82; H, 4.86; N, 8.01
MS: (m/z)=1,033.91 $[M-CH_3]^+$

Synthesis Example 7

Synthesis of Compound 55

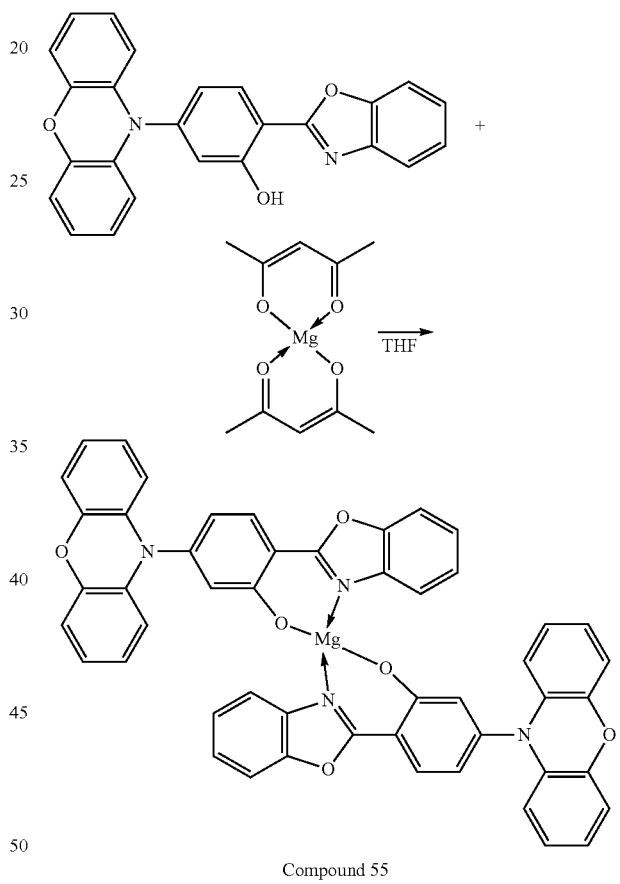

Compound 55

The ligand 1 was obtained in the same manner as in Synthesis Example 1. The ligand 1 (0.39 g, 1.00 mmol) and magnesium acetylacetonate (0.11 g, 0.5 mmol) were dissolved in tetrahydrofuran (6 mL), and the solution was heated under heating to provide the compound 55. The production of the target product was confirmed by MALDI-TOF-MS.

Yield amount: 0.32 g
Yield: 80.5%
m/z=807 ($[M]^+$)

Synthesis Example 8

Synthesis of Compound 67

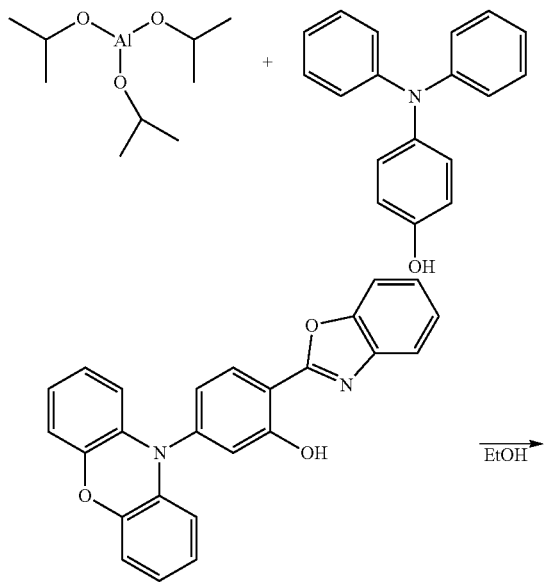

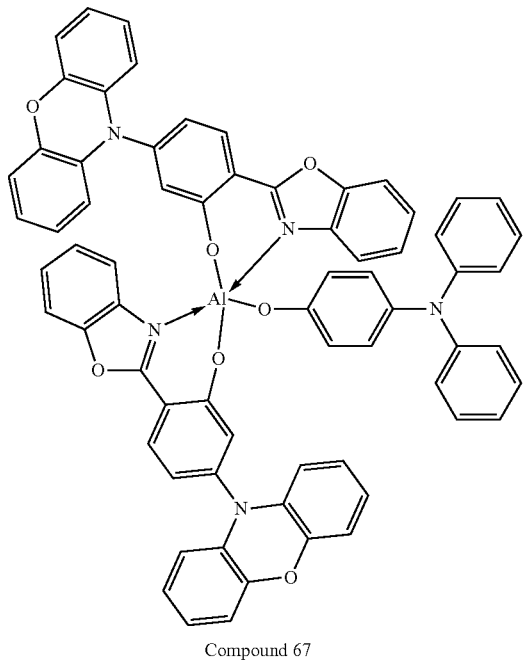

Compound 67

An ethanol solution of aluminum triisopropoxide (0.10 g, 0.5 mmol) and 4-(diphenylamino)phenol (0.39 g, 1.5 mmol) having been deaerated and substituted with nitrogen was stirred at 85° C. for 1 hour. 2-(Benzo[d]oxazol-2-yl)-5-(10H-phenoxazin-10-yl)phenol (0.39 g, 1.00 mmol) was added to the solution, which was heated under stirring for 3 hours. After completing the reaction, the product was filtered and rinsed with ethanol.

The production of the target product was confirmed by MALDI-TOF-MS.

m/z=1,077 ([M+7]$^+$), 809 ([M−261 (TPA)]$^+$)

Measurement Method of $\Delta E_{ST}$

The difference ($\Delta E_{ST}$) between the singlet energy ($E_{S1}$) and the triplet energy ($E_{T1}$) of the materials used in the following examples was obtained in such a manner that the singlet energy ($E_{S1}$) and the triplet energy ($E_{T1}$) were measured in the following manners, and the difference ($\Delta E_{ST}$) was obtained by the expression, $\Delta E_{ST} = E_{S1} - E_{T1}$.

(1) Singlet Energy $E_{S1}$

The compound to be measured and mCBP were vapor-co-deposited to a thickness of 100 nm on a Si substrate to make a concentration of the compound to be measured of 6% by weight, which was designated as a specimen. The specimen was measured for a fluorescence spectrum at ordinary temperature (300 K). The light emission was accumulated from immediately after the incidence of excitation light to after 100 nsec from the incidence, thereby providing a fluorescence spectrum with the fluorescence intensity as the ordinate and the wavelength as the abscissa. In the fluorescence spectrum, the ordinate was the light emission, and the abscissa was the wavelength. A tangent line was drawn for the downfalling part of the light emission spectrum on the short wavelength side, and the wavelength λedge (nm) of the intersection point of the tangent line and the abscissa was obtained. The wavelength value was converted to an energy value according to the following conversion expression to provide the singlet energy $E_{S1}$.

$E_{S1}(\text{eV}) = 1{,}239.85/\lambda\text{edge}$   Conversion Expression

The light emission spectrum was measured with a nitrogen laser (MNL200, produced by Lasertechnik Berlin GmbH) as an excitation light source and a streak camera (C4334, produced by Hamamatsu Photonics K.K.) as a detector.

(2) Triplet Energy $E_{T1}$

The same specimen as used for the singlet energy $E_{S1}$ was cooled to 5 K, the specimen for measuring phosphorescent light was irradiated with excitation light (337 nm), and the phosphorescence intensity was measured with a streak camera. The light emission was accumulated from immediately after 1 msec from the incidence of excitation light to after 10 msec from the incidence, thereby providing a phosphorescence spectrum with the phosphorescence intensity as the ordinate and the wavelength as the abscissa. A tangent line was drawn for the upstanding part of the phosphorescence spectrum on the short wavelength side, and the wavelength λedge (nm) of the intersection point of the tangent line and the abscissa was obtained. The wavelength value was converted to an energy value according to the following conversion expression to provide the triplet energy $E_{T1}$.

$E_{T1}(\text{eV}) = 1{,}239.85/\lambda\text{edge}$   Conversion Expression

The tangent line for the upstanding part of the phosphorescence spectrum on the short wavelength side was drawn in the following manner. Over the range in the phosphorescence spectrum curve of from the short wavelength end to the maximum peak value closest to the short wavelength end among the maximum peak values of the spectrum, a tangent line was assumed while moving within the range toward the long wavelength side. The gradient of the tangent line was increased while the curve was standing up (i.e., the value of the ordinate was increased). The tangent line that was drawn at the point where the gradient thereof became maximum was designated as the tangent line for the upstanding part of the phosphorescence spectrum on the short wavelength side.

A maximum peak having a peak intensity that was 10% or less of the maximum peak intensity of the spectrum was not included in the maximum peak values and thus was not designated as the maximum peak value closest to the short wavelength end, and the tangent line that was drawn at the point where the gradient became maximum that was closest to the maximum peak value closest to the short wavelength end was designated as the tangent line for the upstanding part of the phosphorescence spectrum on the short wavelength side.

Evaluation of Optical Characteristics of Organic Metal Complexes

Example 1

Evaluation of Optical Characteristics of Compound 1

A toluene solution of the compound 1 (concentration: $1.0 \times 10^{-5}$ mol/L) was prepared in a glove box under an Ar atmosphere.

Figure 2:
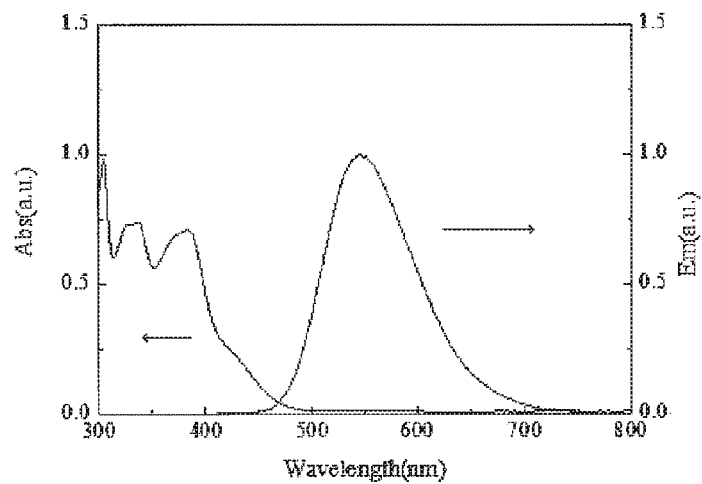
FIG. 2 is the light absorption spectrum and the light emission spectrum of the compound 1 in Example 1.
Figure 3:
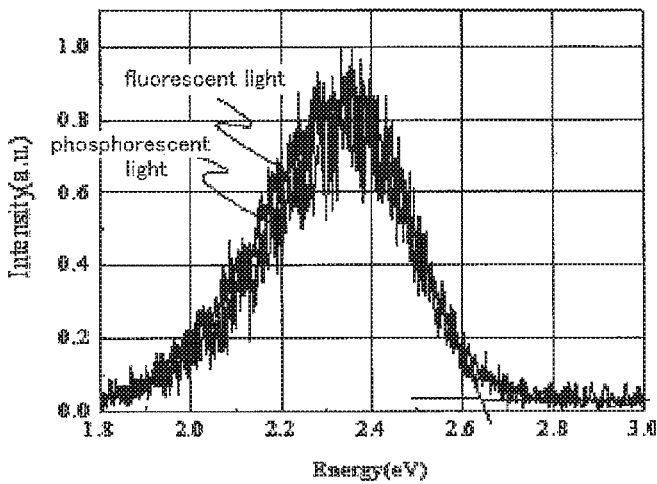
FIG. 3 is the prompt fluorescence spectrum and the phosphorescence spectrum of the compound 1 in Example 1.
Figure 4:
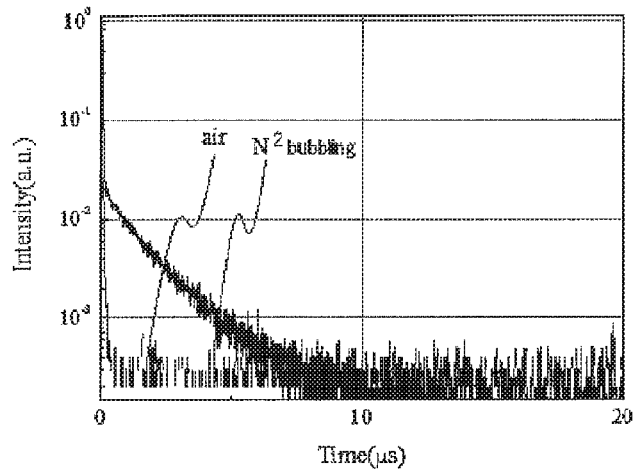
FIG. 4 is the transient decay curves of the compound 1 in Example 1.

For the solution of the compound 1, the results of measurement of the light absorption spectrum and the light emission spectrum with excitation light of 420 nm are shown in FIG. 2, the results of measurement of the prompt fluorescence spectrum and the phosphorescence spectrum are shown in FIG. 3, and the transient decay curves are shown in FIG. 4.

It was understood from FIG. 3 that the compound 1 had $\Delta E_{ST}$ of approximately 0 eV.

It was understood from FIG. 4 that delayed fluorescent light was confirmed in the solution of the compound 1 bubbled with nitrogen, and the photoluminescence quantum efficiency thereof was 62.4%. On the other hand, substantially none of the delayed fluorescent light was confirmed in the solution of the compound 1 without bubbling with nitrogen, and the photoluminescence quantum efficiency was 28.8%. It is estimated that the reason why the solution of the compound 1 without bubbling with nitrogen exhibits a low photoluminescence quantum efficiency is that the compound 1 is a fluorescent substance that exhibits delayed fluorescent light, and in the solution without bubbling with nitrogen, the intersystem crossing of the excitons in the triplet excited state to the singlet excited state is inhibited by oxygen.

Example 2

Evaluation of Optical Characteristics of Compound 2

A solution of the compound 2 was prepared in the same manner as in Example 1 except that the compound 2 was used instead of the compound 1.

Figure 5:
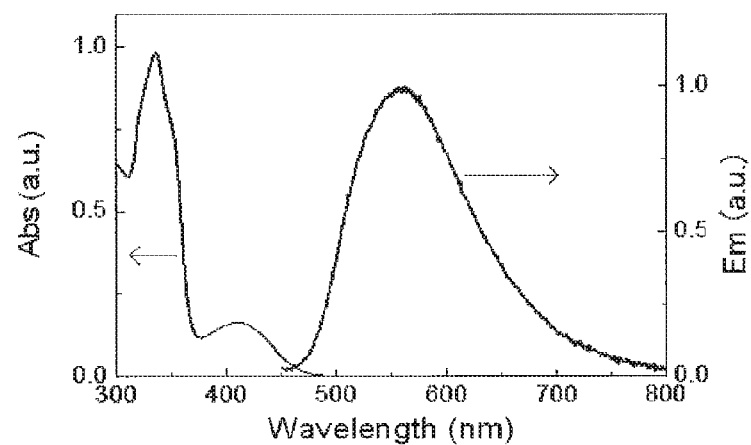
FIG. 5 is the light absorption spectrum and the light emission spectrum of the compound 2 in Example 2.
Figure 6:
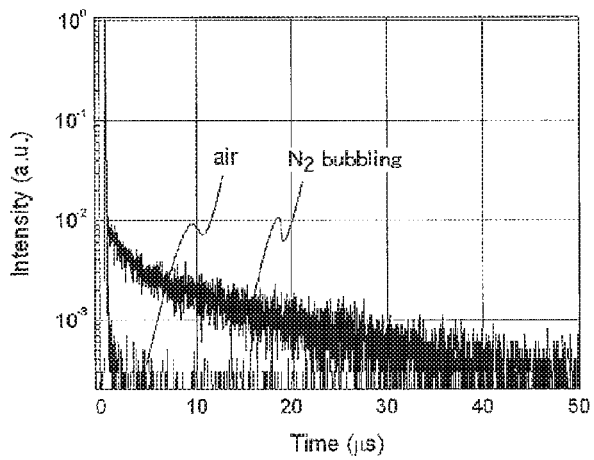
FIG. 6 is the transient decay curves of the compound 2 in Example 2.

For the solution of the compound 2, the results of measurement of the light absorption spectrum and the light emission spectrum with excitation light of 420 nm are shown in FIG. 5, and the transient decay curves are shown in FIG. 6.

It was understood from FIG. 6 that delayed fluorescent light was confirmed in the solution of the compound 2 bubbled with nitrogen, and substantially none of the delayed fluorescent light was confirmed in the solution of the compound 2 without bubbling with nitrogen. It is estimated that the reason why the solution of the compound 2 without bubbling with nitrogen exhibits a low photoluminescence quantum efficiency is that the compound 2 is a fluorescent substance that exhibits delayed fluorescent light, and in the solution without bubbling with nitrogen, the intersystem crossing of the excitons in the triplet excited state to the singlet excited state is inhibited by oxygen.

Example 3

Evaluation of Optical Characteristics of Compound 3

A solution of the compound 3 was prepared in the same manner as in Example 1 except that the compound 3 was used instead of the compound 1.

Figure 7:
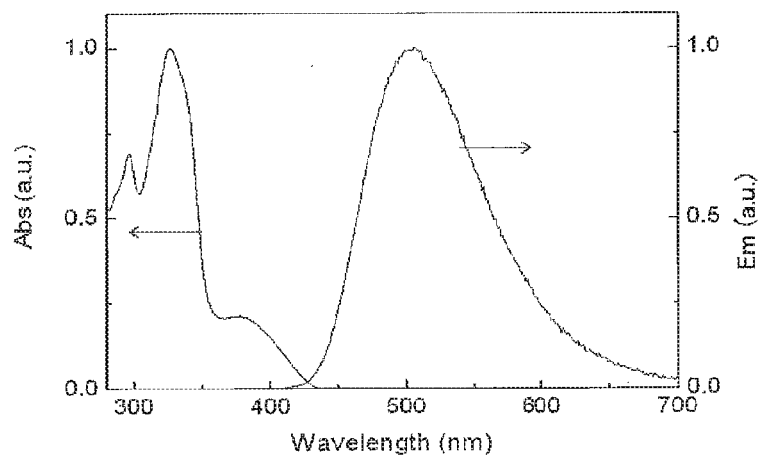
FIG. 7 is the light absorption spectrum and the light emission spectrum of the compound 3 in Example 3.
Figure 8:
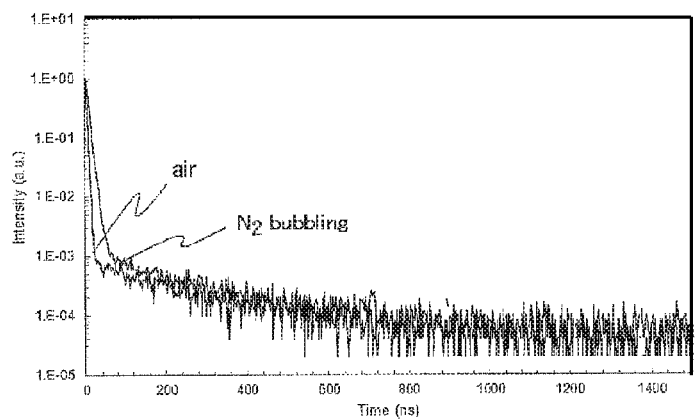
FIG. 8 is the transient decay curves of the compound 3 in Example 3.

For the solution of the compound 3, the results of measurement of the light absorption spectrum and the light emission spectrum with excitation light of 420 nm are shown in FIG. 7, and the transient decay curves are shown in FIG. 8.

It was understood from FIG. 8 that delayed fluorescent light was confirmed in the solution of the compound 3 bubbled with nitrogen, and substantially none of the delayed fluorescent light was confirmed in the solution of the compound 3 without bubbling with nitrogen. It is estimated that the reason why the solution of the compound 3 without bubbling with nitrogen exhibits a low photoluminescence quantum efficiency is that the compound 3 is a fluorescent substance that exhibits delayed fluorescent light, and in the solution without bubbling with nitrogen, the intersystem crossing of the excitons in the triplet excited state to the singlet excited state is inhibited by oxygen.

Example 4

Evaluation of Optical Characteristics of Compound 13

A solution of the compound 13 was prepared in the same manner as in Example 1 except that the compound 13 was used instead of the compound 1.

Figure 9:
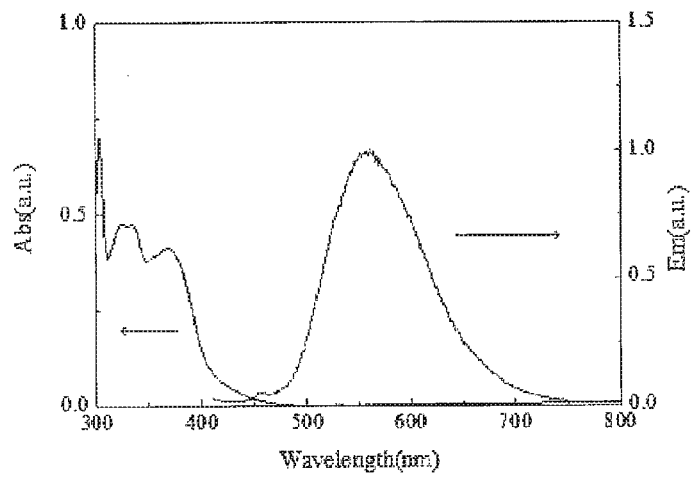
FIG. 9 is the light absorption spectrum and the light emission spectrum of the compound 13 in Example 4.
Figure 10:
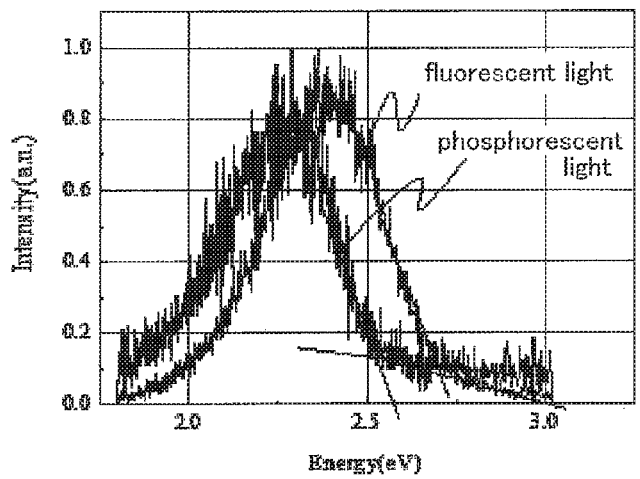
FIG. 10 is the prompt fluorescence spectrum and the phosphorescence spectrum of the compound 13 in Example 4.
Figure 11:
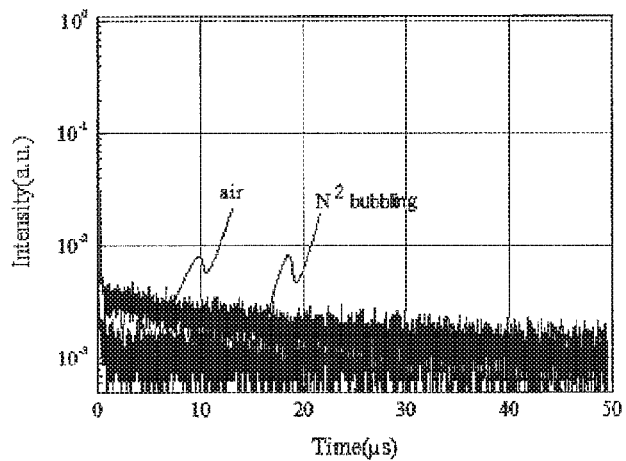
FIG. 11 is the transient decay curves of the compound 13 in Example 4.

For the solution of the compound 13, the results of measurement of the light absorption spectrum and the light emission spectrum with excitation light of 420 nm are shown in FIG. 9, the results of measurement of the prompt fluorescence spectrum and the phosphorescence spectrum are shown in FIG. 10, and the transient decay curves are shown in FIG. 11.

It was understood from FIG. 10 that the compound 13 had $\Delta E_{ST}$ of 0.18 eV, and the ligand had $\Delta E_{ST}$ of 0.16 eV.

It was understood from FIG. 11 that delayed fluorescent light was confirmed in the solution of the compound 13 bubbled with nitrogen, and the photoluminescence quantum efficiency thereof was 36.2%. On the other hand, substantially none of the delayed fluorescent light was confirmed in the solution of the compound 13 without bubbling with nitrogen, and the photoluminescence quantum efficiency thereof was 12.5%. It is estimated that the reason why the solution of the compound 13 without bubbling with nitrogen exhibits a low photoluminescence quantum efficiency is that the compound 13 is a fluorescent substance that exhibits delayed fluorescent light, and in the solution without bubbling with nitrogen, the intersystem crossing of the excitons in the triplet excited state to the singlet excited state is inhibited by oxygen.

Example 5

Evaluation of Optical Characteristics of Compound 25

A solution of the compound 25 was prepared in the same manner as in Example 1 except that the compound 25 was used instead of the compound 1.

Figure 12:
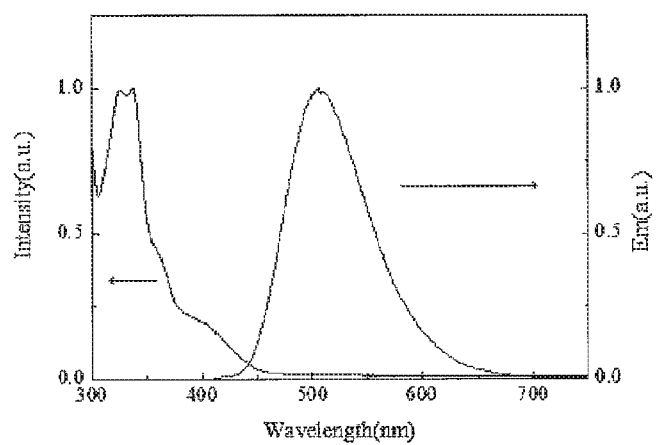
FIG. 12 is the light absorption spectrum and the light emission spectrum of the compound 25 in Example 5.
Figure 13:
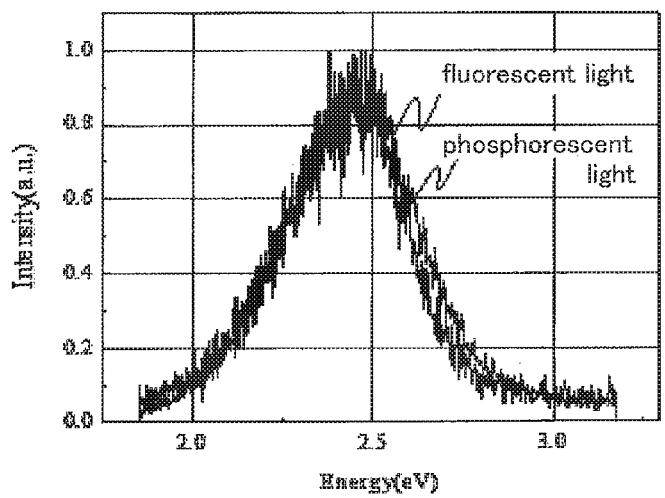
FIG. 13 is the prompt fluorescence spectrum and the phosphorescence spectrum of the compound 25 in Example 5.
Figure 14:
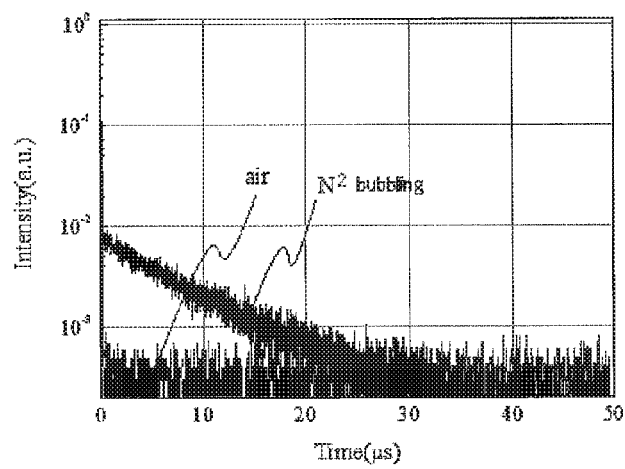
FIG. 14 is the transient decay curves of the compound 25 in Example 5.

For the solution of the compound 25, the results of measurement of the light absorption spectrum and the light emission spectrum with excitation light of 400 nm are shown in FIG. 12, the results of measurement of the prompt fluorescence spectrum and the phosphorescence spectrum are shown in FIG. 13, and the transient decay curves are shown in FIG. 14.

It was understood from FIG. 13 that the compound 25 had $\Delta E_{ST}$ of 0.05 eV, and the ligand had $\Delta E_{ST}$ of 0.14 eV.

It was understood from FIG. 14 that delayed fluorescent light was confirmed in the solution of the compound 25 bubbled with nitrogen, and the photoluminescence quantum efficiency thereof was 58.5%. On the other hand, substantially none of the delayed fluorescent light was confirmed in the solution of the compound 25 without bubbling with nitrogen, and the photoluminescence quantum efficiency thereof was 17.7%. It is estimated that the reason why the solution of the compound 25 without bubbling with nitrogen exhibits a low photoluminescence quantum efficiency is that the compound 25 is a fluorescent substance that exhibits delayed fluorescent light, and in the solution without bubbling with nitrogen, the intersystem crossing of the excitons in the triplet excited state to the singlet excited state is inhibited by oxygen.

Example 6

Evaluation of Optical Characteristics of Compound 51

A solution of the compound 51 was prepared in the same manner as in Example 1 except that the compound 51 was used instead of the compound 1.

Figure 15:
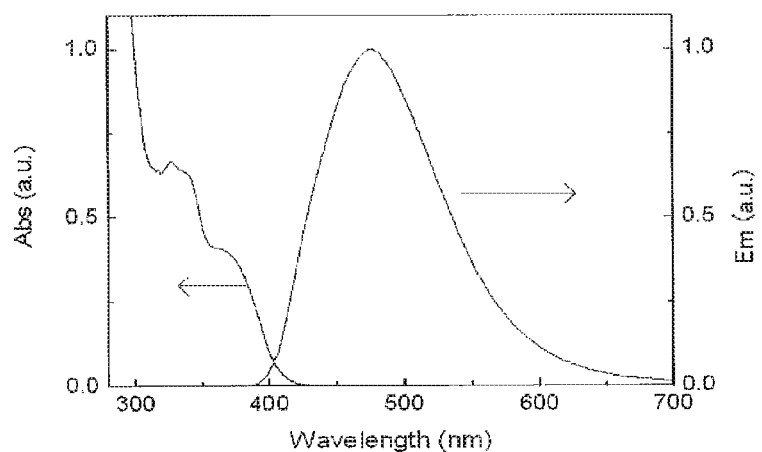
FIG. 15 is the light absorption spectrum and the light emission spectrum of the compound 51 in Example 6.
Figure 16:
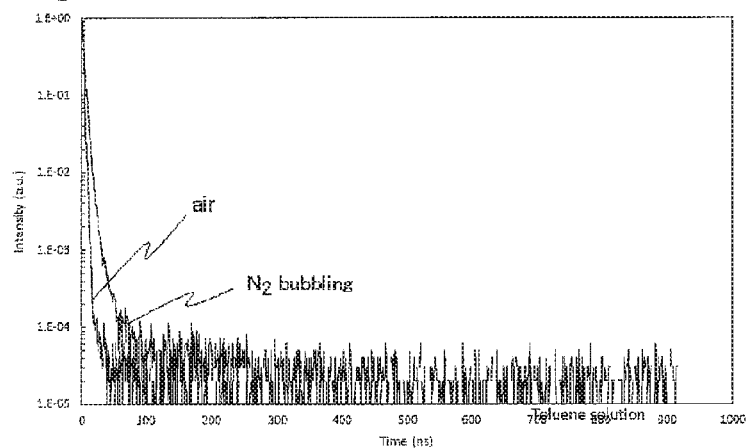
FIG. 16 is the transient decay curves of the compound 51 in Example 6.

For the solution of the compound 51, the results of measurement of the light absorption spectrum and the light emission spectrum with excitation light of 420 nm are shown in FIG. 15, and the transient decay curves are shown in FIG. 16.

It was understood from FIG. 16 that delayed fluorescent light was confirmed in the solution of the compound 51 bubbled with nitrogen, and substantially none of the delayed fluorescent light was confirmed in the solution of the compound 51 without bubbling with nitrogen. It is estimated that the reason why the solution of the compound 51 without bubbling with nitrogen exhibits a low photoluminescence quantum efficiency is that the compound 51 is a fluorescent substance that exhibits delayed fluorescent light, and in the solution without bubbling with nitrogen, the intersystem crossing of the excitons in the triplet excited state to the singlet excited state is inhibited by oxygen.

Example 7

Evaluation of Optical Characteristics of Compound 55

A solution of the compound 55 was prepared in the same manner as in Example 1 except that the compound 55 was used instead of the compound 1.

Figure 17:
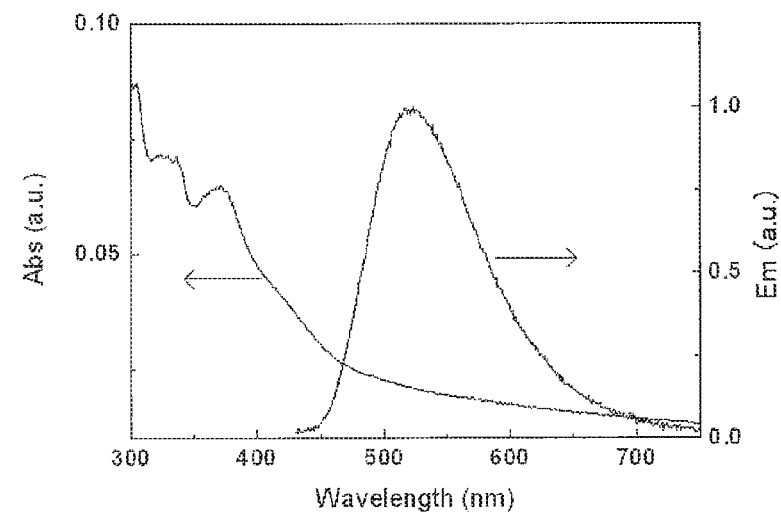
FIG. 17 is the light absorption spectrum and the light emission spectrum of the compound 55 in Example 7.
Figure 18:
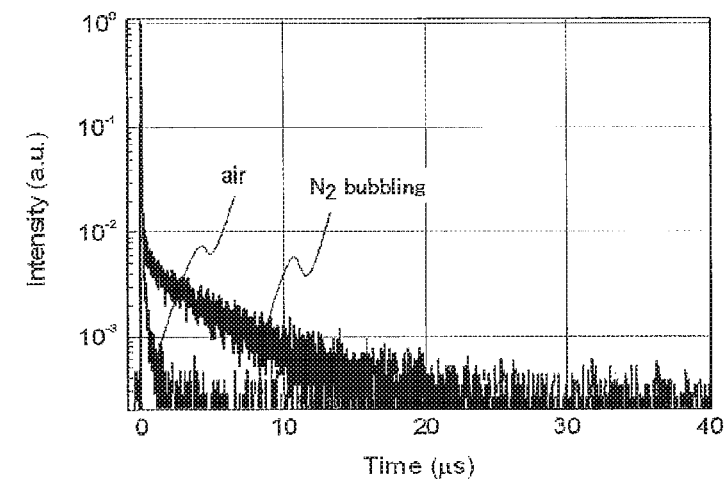
FIG. 18 is the transient decay curves of the compound 55 in Example 7.

For the solution of the compound 55, the results of measurement of the light absorption spectrum and the light emission spectrum with excitation light of 420 nm are shown in FIG. 17, and the transient decay curves are shown in FIG. 18.

It was understood from FIG. 18 that delayed fluorescent light was confirmed in the solution of the compound 55 bubbled with nitrogen, and substantially none of the delayed fluorescent light was confirmed in the solution of the compound 55 without bubbling with nitrogen. It is estimated that the reason why the solution of the compound 55 without bubbling with nitrogen exhibits a low photoluminescence quantum efficiency is that the compound 55 is a fluorescent substance that exhibits delayed fluorescent light, and in the solution without bubbling with nitrogen, the intersystem crossing of the excitons in the triplet excited state to the singlet excited state is inhibited by oxygen.

Example 8

Evaluation of Optical Characteristics of Compound 67

A solution of the compound 67 was prepared in the same manner as in Example 1 except that the compound 67 was used instead of the compound 1.

Figure 19:
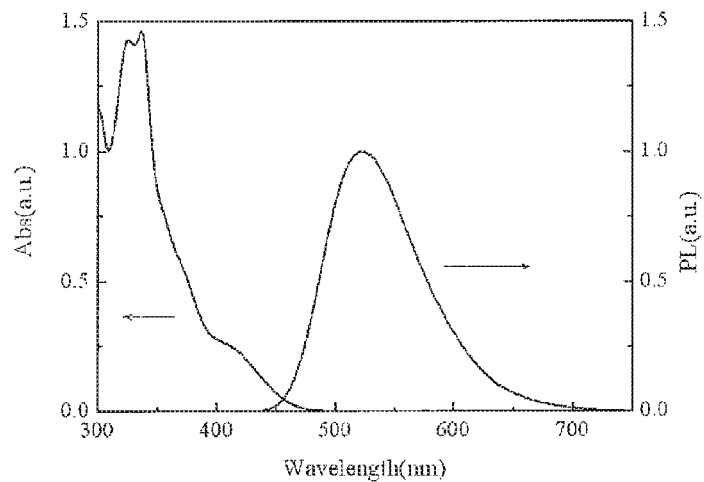
FIG. 19 is the light absorption spectrum and the light emission spectrum of the compound 67 in Example 8.
Figure 20:
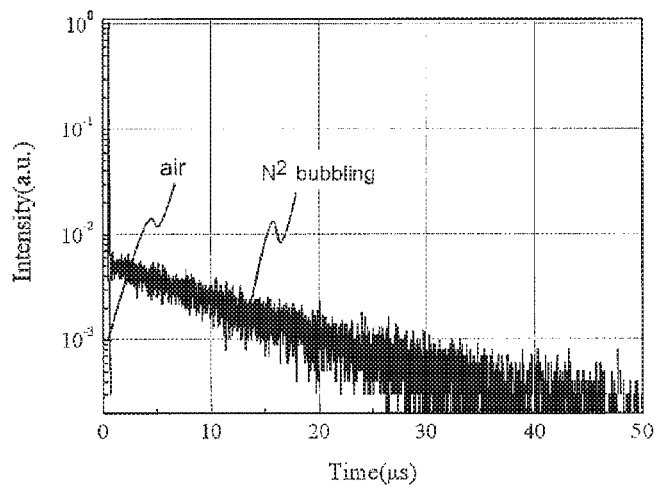
FIG. 20 is the transient decay curves of the compound 67 in Example 8.

For the solution of the compound 67, the results of measurement of the light absorption spectrum and the light emission spectrum with excitation light of 400 nm are shown in FIG. 19, and the transient decay curves are shown in FIG. 20. It was understood from FIG. 20 that delayed fluorescent light was confirmed in the solution of the compound 67 bubbled with nitrogen, and the photoluminescence quantum efficiency thereof was 69.2%. On the other hand, substantially none of the delayed fluorescent light was confirmed in the solution of the compound 67 without bubbling with nitrogen, and the photoluminescence quantum efficiency thereof was 15.8%. It is estimated that the reason why the solution of the compound 67 without bubbling with nitrogen exhibits a low photoluminescence quantum efficiency is that the compound 67 is a fluorescent substance that exhibits delayed fluorescent light, and in the solution without bubbling with nitrogen, the intersystem crossing of the excitons in the triplet excited state to the singlet excited state is inhibited by oxygen.

Comparative Example 1

Evaluation of Optical Characteristics of Comparative Compound A

A solution of the comparative compound A having the following structure was prepared in the same manner as in Example 1 except that the comparative compound A was used instead of the compound 1.

Figure 21:
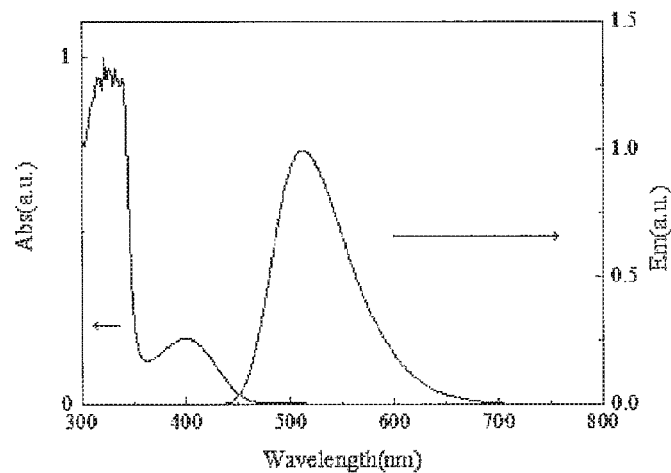
FIG. 21 is the light absorption spectrum and the light emission spectrum of the comparative compound A in Comparative Example 1.
Figure 22:
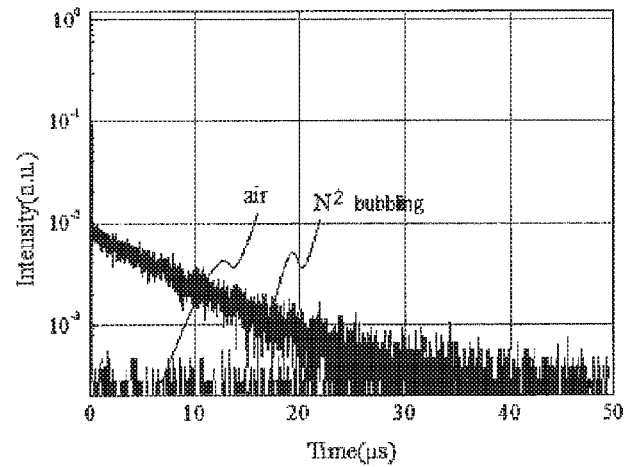
FIG. 22 is the transient decay curves of the comparative compound A in Comparative Example 1.

For the solution of the comparative compound A, the results of measurement of the light absorption spectrum and the light emission spectrum with excitation light of 400 nm are shown in FIG. 21, and the transient decay curves are shown in FIG. 22.

It was understood from FIG. 22 that delayed fluorescent light was confirmed in the solution of the comparative compound A bubbled with nitrogen, and the photoluminescence quantum efficiency thereof was 37.3% for the solution bubbled with nitrogen and 17.7% for the solution without bubbling with nitrogen, which were lower than the compounds of Examples.

Comparative Compound A

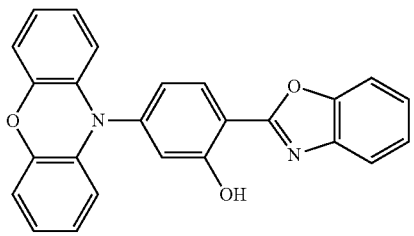

Comparative Example 2

Evaluation of Optical Characteristics of Comparative Compound B

A solution of the comparative compound B having the following structure was prepared in the same manner as in Example 1 except that the comparative compound B was used instead of the compound 1.

Figure 23:
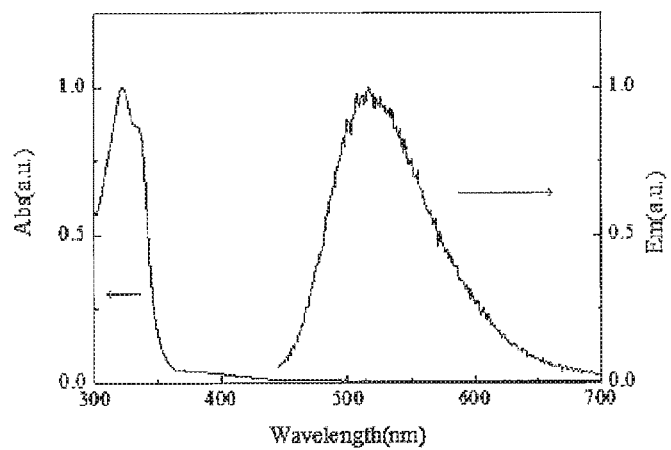
FIG. 23 is the light absorption spectrum and the light emission spectrum of the comparative compound B in Comparative Example 2.
Figure 24:
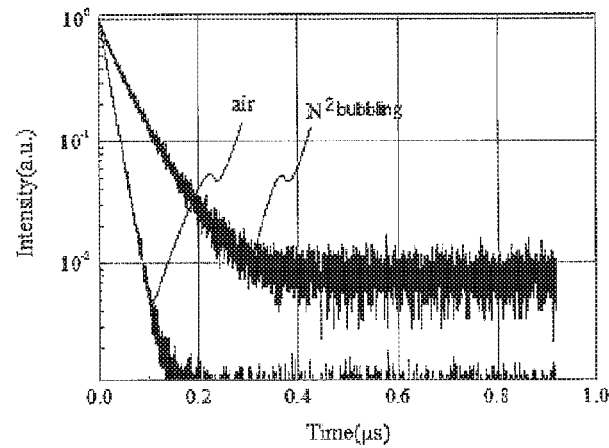
FIG. 24 is the transient decay curves of the comparative compound B in Comparative Example 2.

For the solution of the comparative compound B, the results of measurement of the light absorption spectrum and the light emission spectrum with excitation light of 380 nm are shown in FIG. 23, and the transient decay curves are shown in FIG. 24. It was understood from FIG. 24 that delayed fluorescent light was confirmed in the solution of the comparative compound B bubbled with nitrogen, and the photoluminescence quantum efficiency thereof was 38.9% for the solution bubbled with nitrogen and 7.5% for the solution without bubbling with nitrogen, which were lower than the compounds of Examples.

Comparative Compound B

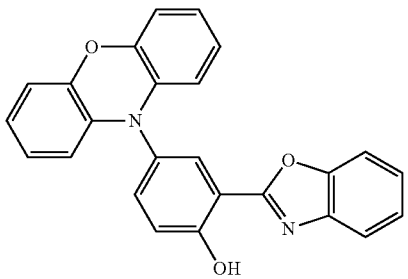

Production and Evaluation of Thin Films

Example 9

Figure 25:
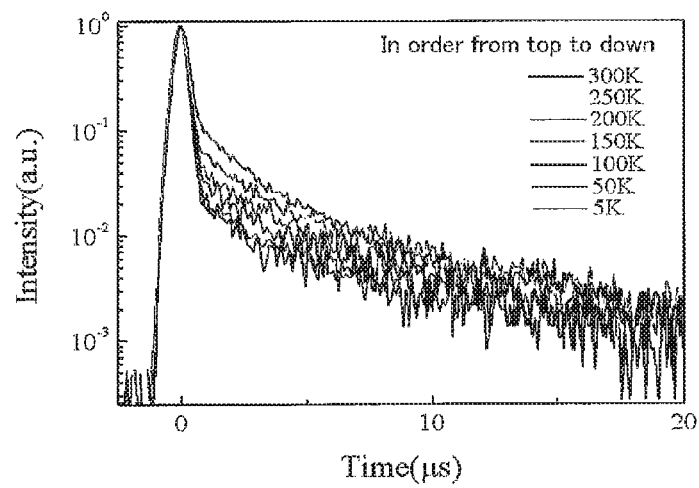
FIG. 25 is the transient decay curves of the thin film of the compound 1 in Example 9.

The compound 1 and mCBP were vapor-deposited from separate vapor deposition sources on a quartz substrate by a vacuum vapor deposition method under a condition of a vacuum degree of $10^{-4}$ Pa or less to form a vapor-co-deposited thin film having a thickness of 100 nm having a concentration of the compound 1 of 0.6% by weight. The results of the measurement of the transient decay curves of photoluminescence of the thin film by excitation light of 325 nm at 5 K, 50 K, 100 K, 150 K, 200 K, 250 K, and 300 K are shown in FIG. 25. It was confirmed that the compound 1 was a thermal activation type delayed fluorescent material.

Example 10

Figure 26:
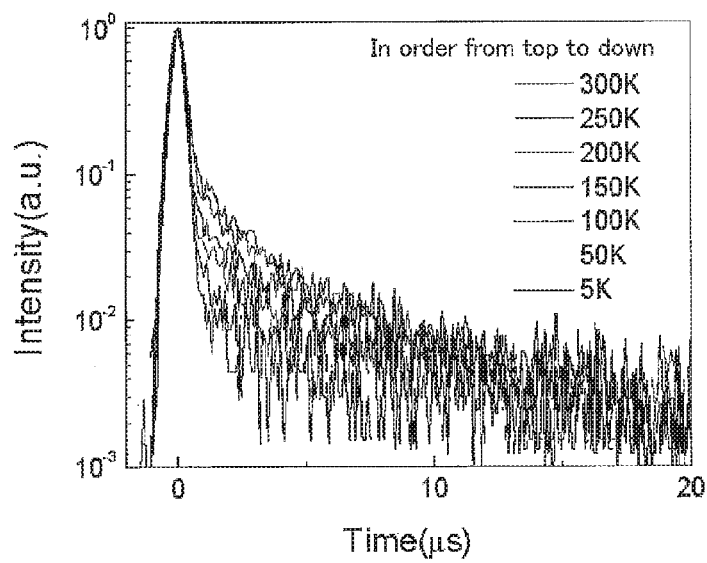
FIG. 26 is the transient decay curves of the thin film of the compound 2 in Example 10.
Figure 27:
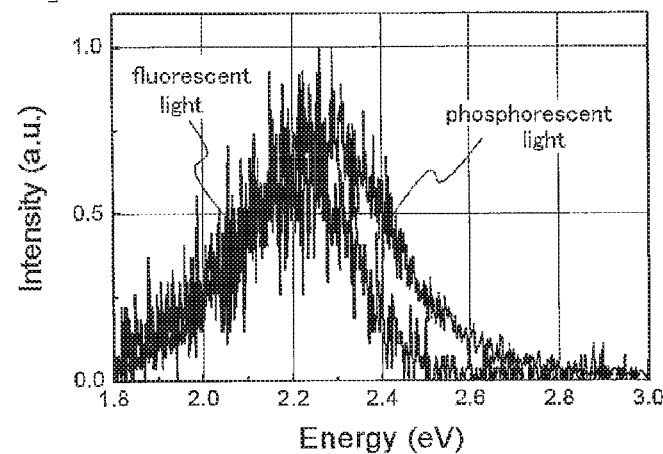
FIG. 27 is the prompt fluorescence spectrum and the phosphorescence spectrum of the compound 2 in Example 10.

A thin film was produced and evaluated in the same manner as in Example 9 except that the compound 2 was used instead of the compound 1. The transient decay curves of the compound 2 are shown in FIG. 26, and the results of the measurement of the prompt fluorescence spectrum and the phosphorescence spectrum thereof are shown in FIG. 27. It was confirmed that the compound 2 had $\Delta E_{ST}$ of 0.14 eV, and the compound 2 was a thermal activation type delayed fluorescent material.

Example 11

Figure 28:
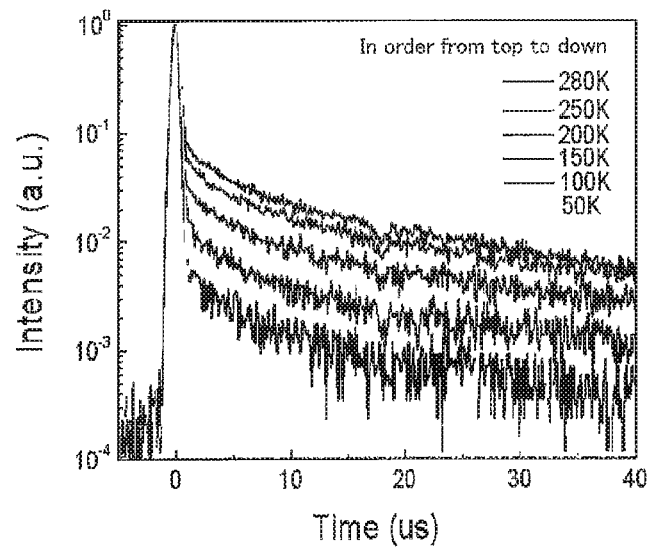
FIG. 28 is the transient decay curves of the thin film of the compound 3 in Example 11.
Figure 29:
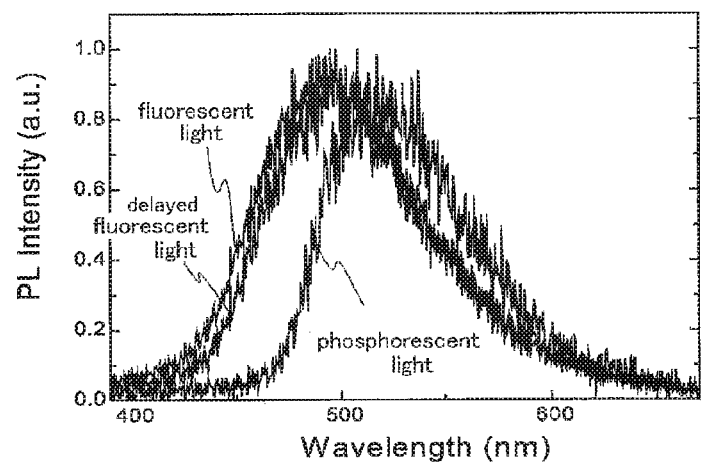
FIG. 29 is the fluorescence spectrum and the phosphorescence spectrum of the compound 3 in Example 11.

A thin film was produced and evaluated in the same manner as in Example 9 except that the compound 3 was used instead of the compound 1. The transient decay curves of the compound 3 are shown in FIG. 28, and the results of the measurement of the fluorescence spectrum and the phosphorescence spectrum thereof are shown in FIG. 29. It was confirmed that the compound 3 had $\Delta E_{ST}$ of 0.12 eV, and the compound 3 was a thermal activation type delayed fluorescent material.

Example 12

Figure 30:
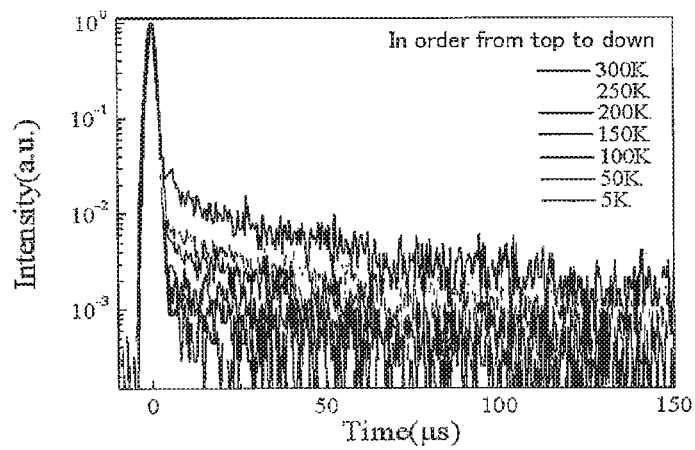
FIG. 30 is the transient decay curves of the thin film of the compound 13 in Example 12.

A thin film was produced and evaluated in the same manner as in Example 9 except that the compound 13 was used instead of the compound 1. The transient decay curves of the compound 13 are shown in FIG. 30. It was confirmed that the compound 13 was a thermal activation type delayed fluorescent material.

Example 13

Figure 31:
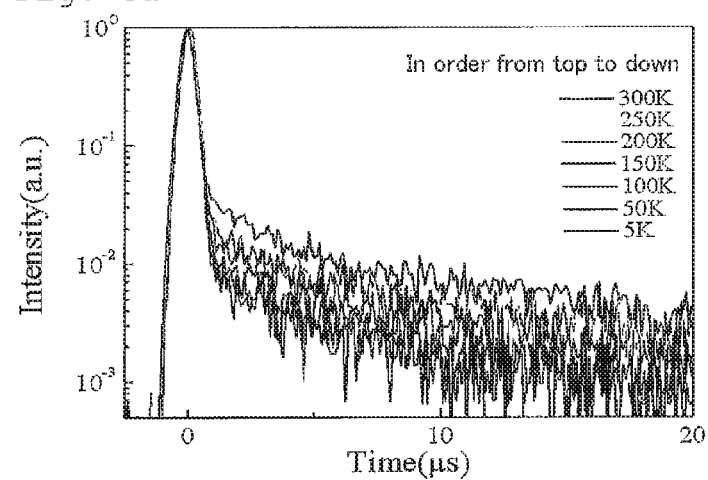
FIG. 31 is the transient decay curves of the thin film of the compound 25 in Example 13.

A thin film was produced and evaluated in the same manner as in Example 9 except that the compound 25 was used instead of the compound 1. The transient decay curves of the compound 25 are shown in FIG. 31. It was confirmed that the compound 25 was a thermal activation type delayed fluorescent material.

Example 14

Figure 32:
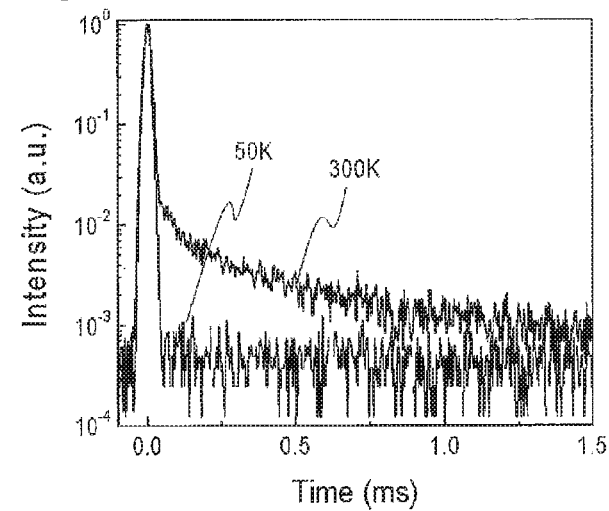
FIG. 32 is the transient decay curves of the thin film of the compound 51 in Example 14.
Figure 33:
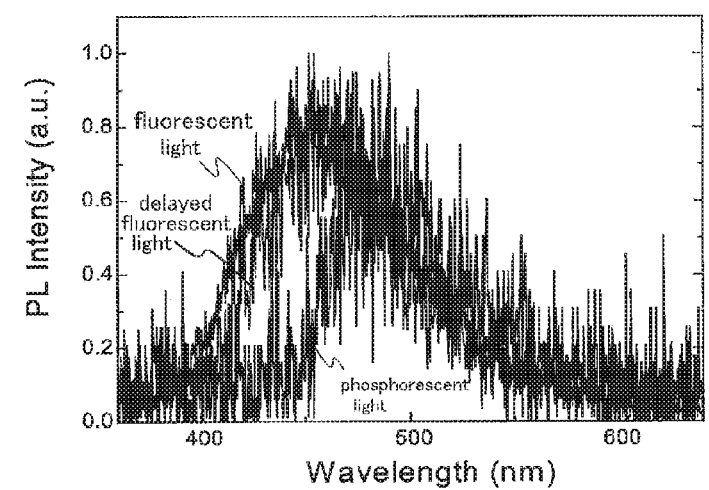
FIG. 33 is the fluorescence spectrum and the phosphorescence spectrum of the compound 51 in Example 14.

A thin film was produced and evaluated in the same manner as in Example 9 except that the compound 51 was used instead of the compound 1. The transient decay curves of the compound 51 are shown in FIG. 32, and the results of the measurement of the fluorescence spectrum and the phosphorescence spectrum thereof are shown in FIG. 33. It was confirmed that the compound 51 had $\Delta E_{ST}$ of 0.33 eV, and the compound 51 was a thermal activation type delayed fluorescent material.

Example 15

Figure 34:
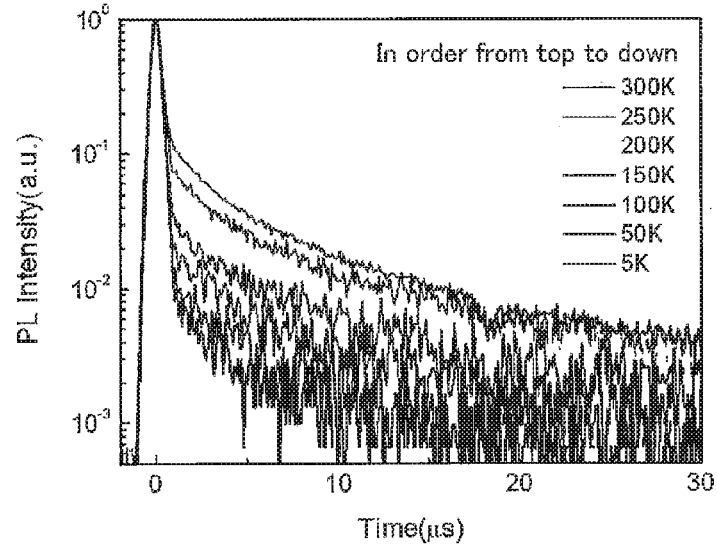
FIG. 34 is the transient decay curves of the thin film of the compound 55 in Example 15.
Figure 35:
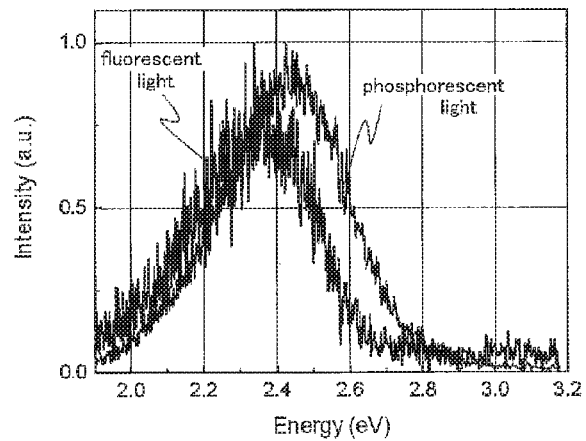
FIG. 35 is the prompt fluorescence spectrum and the phosphorescence spectrum of the compound 55 in Example 15.

A thin film was produced and evaluated in the same manner as in Example 9 except that the compound 55 was used instead of the compound 1. The transient decay curves of the compound 55 are shown in FIG. 34, and the results of the measurement of the prompt fluorescence spectrum and the phosphorescence spectrum thereof are shown in FIG. 35. It was confirmed that the compound 55 had $\Delta E_{ST}$ of 0.14 eV, and the compound 55 was a thermal activation type delayed fluorescent material.

Example 16

Figure 36:
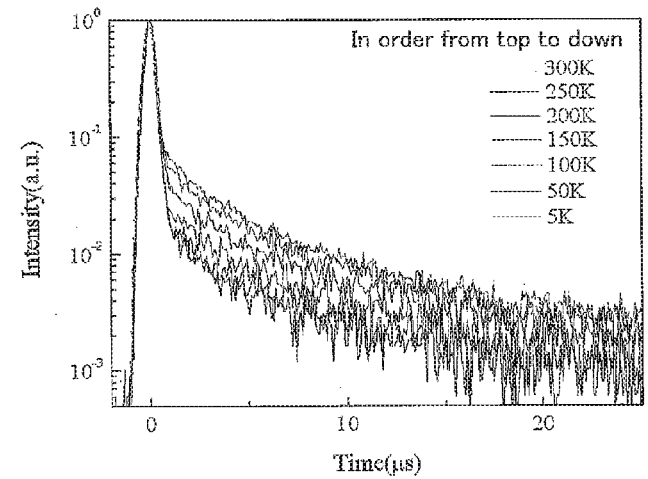
FIG. 36 is the transient decay curves of the thin film of the compound 67 in Example 16.
Figure 37:
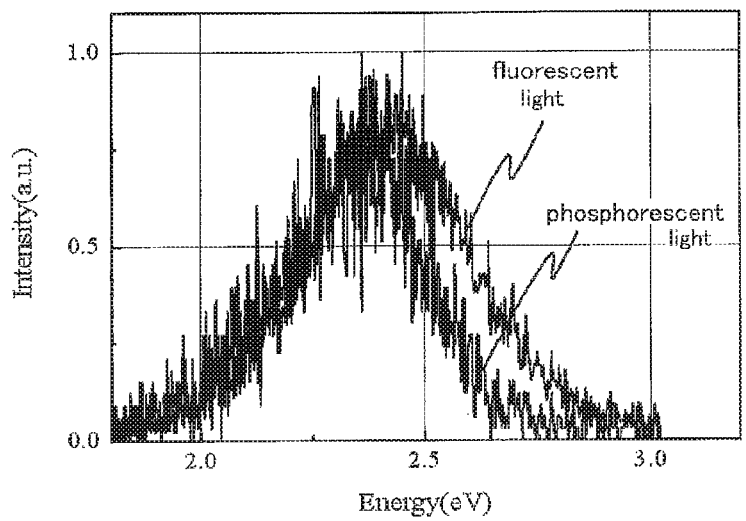
FIG. 37 is the prompt fluorescence spectrum and the phosphorescence spectrum of the compound 67 in Example 16.

A thin film was produced and evaluated in the same manner as in Example 9 except that the compound 67 was used instead of the compound 1, and the thin film was produced by spin casting by using the compound 67 with mCBP as a host material. The transient decay curves of the compound 67 are shown in FIG. 36. It was confirmed that the compound 67 was a thermal activation type delayed fluorescent material. The results of the measurement of the prompt fluorescence spectrum and the phosphorescence spectrum of the compound 67 are shown in FIG. 37. It was understood from FIG. 37 that the compound 67 had $\Delta E_{ST}$ of 0.13 eV.

Comparative Examples 3 to 6

Thin films were produced and evaluated in the same manner as in Example 16 except that the comparative compounds C to F were used instead of the compound 1. No delayed fluorescent light component was confirmed in the transient decay curves of the comparative compounds C to F. $\Delta E_{ST}$ was 0.59 eV for the comparative compound C, 0.58 eV for the comparative compound D, 0.45 eV for the comparative compound E, and 0.43 eV for the comparative compound F, all of which were larger than 0.2 eV.

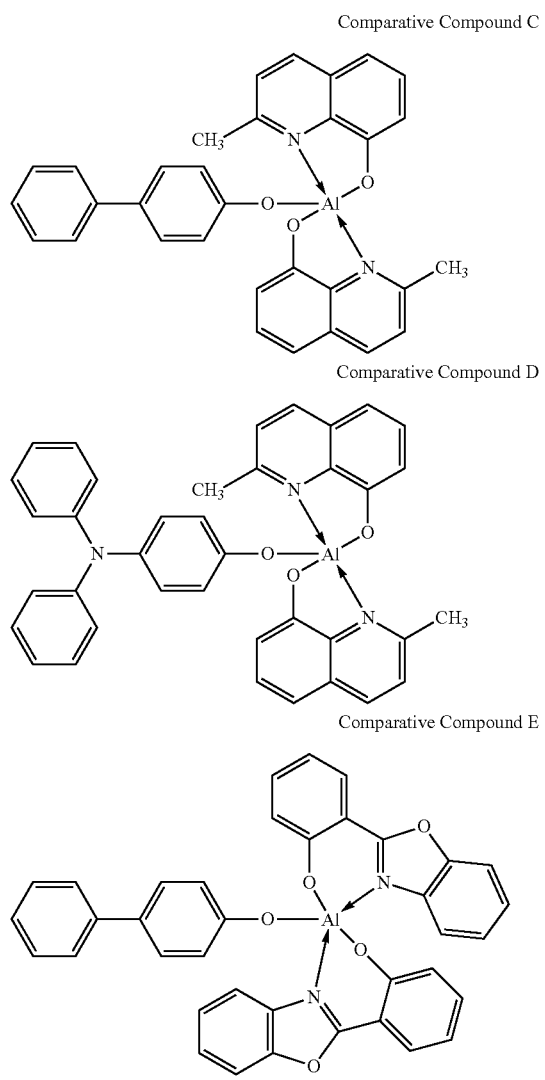

Comparative Compound C

Comparative Compound D

Comparative Compound E

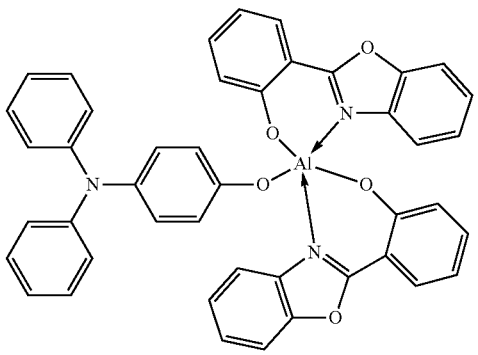

Comparative Compound F

Production and Evaluation of Organic Electroluminescent Devices

Example 17

Production and Evaluation of Organic Electroluminescent Device Using Compound 1

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 35 nm on ITO. Subsequently, the compound 1 and mCBP were co-deposited thereon from separate vapor deposition sources to form a layer having a thickness of 15 nm, which was designated as a light emitting layer. At this time, the concentration of the compound 1 was 6.0% by weight. TPBi was then formed to a thickness of 65 nm, further lithium fluoride (LiF) was vacuum vapor-deposited to a thickness of 0.8 nm, and then aluminum (Al) was vapor-deposited to a thickness of 80 nm to form a cathode, thereby completing an organic electroluminescent device.

Figure 38:
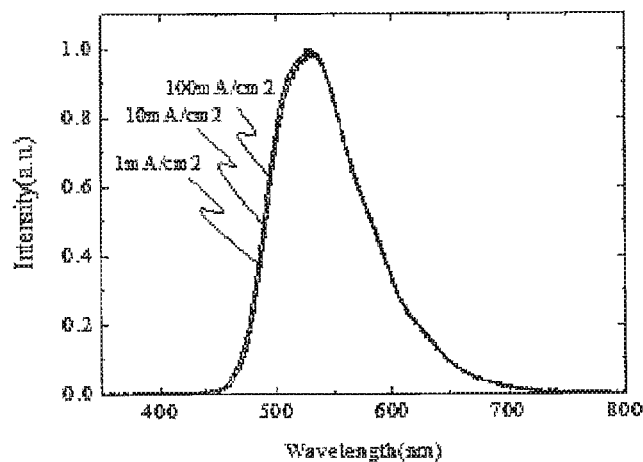
FIG. 38 is the light emission spectra of the organic electroluminescent device of the compound 1 in Example 17.
Figure 39:
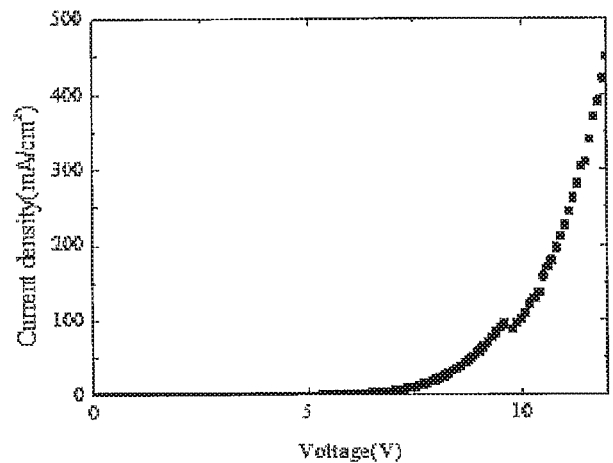
FIG. 39 is a graph showing the voltage-current density characteristics of the organic electroluminescent device of the compound 1 in Example 17.
Figure 40:
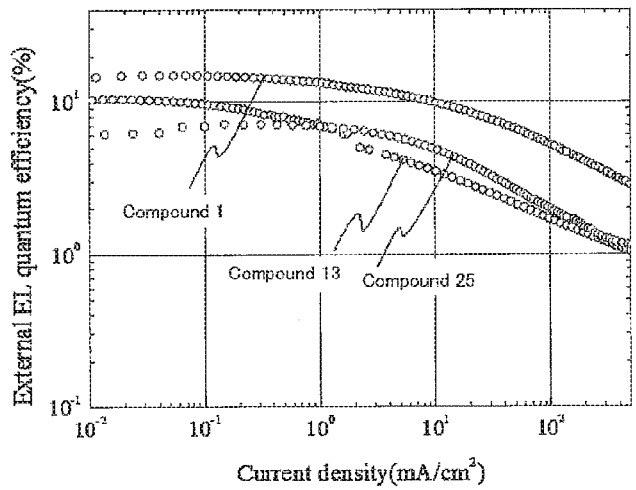
FIG. 40 is a graph showing the current density-external quantum efficiency characteristics of the organic electroluminescent devices of the compound 1 in Example 17, the compound 13 in Example 20, and the compound 25 in Example 21.

FIG. 38 shows the light emission spectra of the organic electroluminescent device thus produced, FIG. 39 shows the voltage-current density characteristics thereof, and FIG. 40 shows the current density-external quantum efficiency characteristics thereof. The organic electroluminescent device using the compound 1 as a light emitting material exhibited a high external quantum efficiency of 15.0%. If an ideally balanced organic electroluminescent device is produced by using a fluorescent material having a light emission quantum efficiency of 100%, the external quantum efficiency of the fluorescent light emission may be from 5 to 7.5% assuming that the light extraction efficiency is from 20 to 30%. It has been ordinarily considered that this value is the theoretical limit value of an external quantum efficiency of an organic electroluminescent device using a fluorescent material. The organic electroluminescent device of the invention using the compound 1 is considerably excellent in such a point that a high external quantum efficiency that exceeds the theoretical limit value is achieved.

Example 18

Production and Evaluation of Organic Electroluminescent Device Using Compound 2

An organic electroluminescent device was produced in the same manner as in Example 17 except that the compound 2 was used instead of the compound 1.

Figure 41:
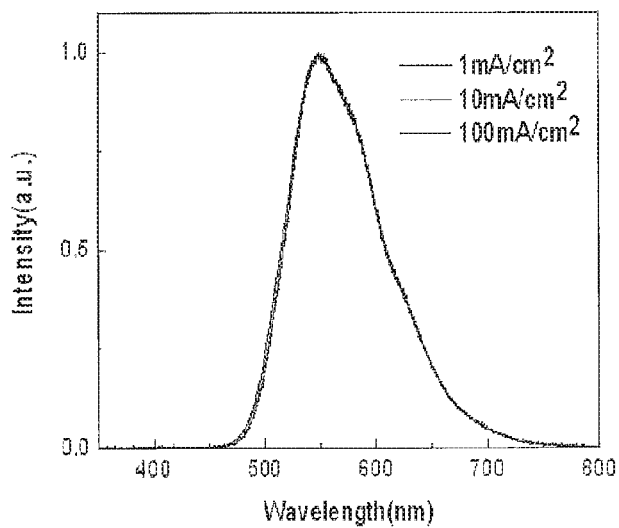
FIG. 41 is the light emission spectra of the organic electroluminescent device of the compound 2 in Example 18.
Figure 42:
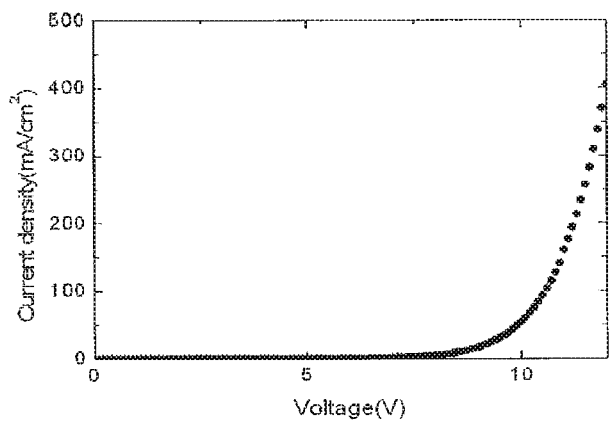
FIG. 42 is a graph showing the voltage-current density characteristics of the organic electroluminescent device of the compound 2 in Example 18.
Figure 43:
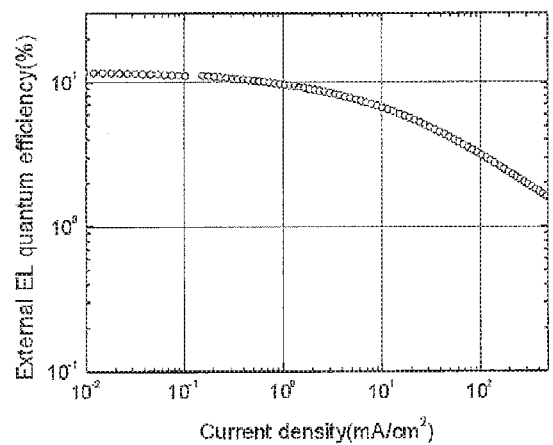
FIG. 43 is a graph showing the current density-external quantum efficiency characteristics of the organic electroluminescent device of the compound 2 in Example 18.

FIG. 41 shows the light emission spectra of the organic electroluminescent device thus produced, FIG. 42 shows the voltage-current density characteristics thereof, and FIG. 43 shows the current density-external quantum efficiency characteristics thereof. The organic electroluminescent device using the compound 2 as a light emitting material exhibited a high external quantum efficiency of 11.6%.

Example 19

Production and Evaluation of Organic Electroluminescent Device Using Compound 3

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 35 nm on ITO, and mCP was formed to a thickness of 10 nm thereon. Subsequently, the compound 3 and mCP were co-deposited thereon from separate vapor deposition sources to form a layer having a thickness of 30 nm, which was designated as a light emitting layer. At this time, the concentration of the compound 3 was 10.0% by weight. PPT was formed to a thickness of 10 nm, TPBi was then formed to a thickness of 25 nm, further lithium fluoride (LiF) was vacuum vapor-deposited to a thickness of 0.8 nm, and then aluminum (Al) was vapor-deposited to a thickness of 80 nm to form a cathode, thereby completing an organic electroluminescent device.

Figure 44:
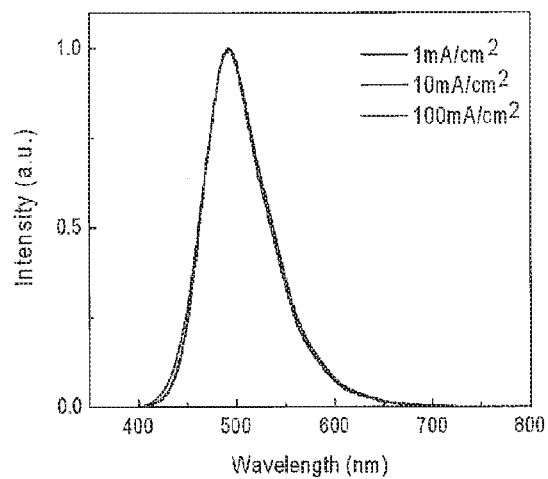
FIG. 44 is the light emission spectra of the organic electroluminescent device of the compound 3 in Example 19.
Figure 45:
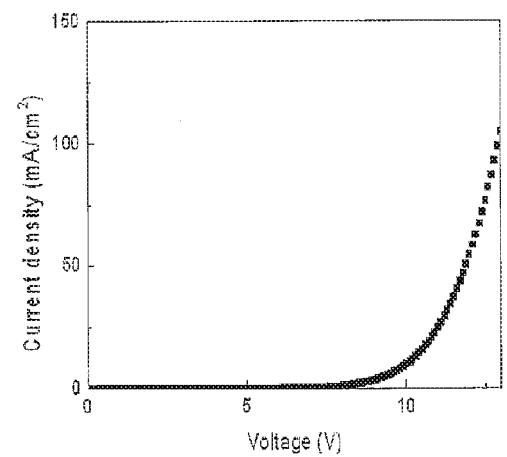
FIG. 45 is a graph showing the voltage-current density characteristics of the organic electroluminescent device of the compound 3 in Example 19.
Figure 46:
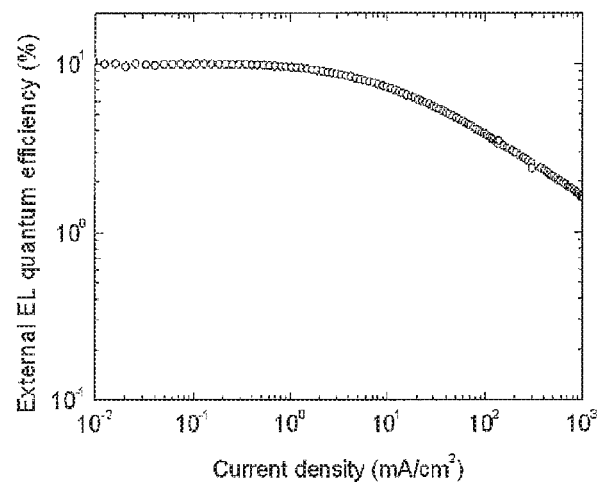
FIG. 46 is a graph showing the current density-external quantum efficiency characteristics of the organic electroluminescent device of the compound 3 in Example 19.

FIG. 44 shows the light emission spectra of the organic electroluminescent device thus produced, FIG. 45 shows the voltage-current density characteristics thereof, and FIG. 46 shows the current density-external quantum efficiency characteristics thereof. The organic electroluminescent device using the compound 3 as a light emitting material exhibited a high external quantum efficiency of 10.1%.

Example 20

Production and Evaluation of Organic Electroluminescent Device Using Compound 13

An organic electroluminescent device was produced in the same manner as in Example 17 except that the compound 13 was used instead of the compound 1.

Figure 47:
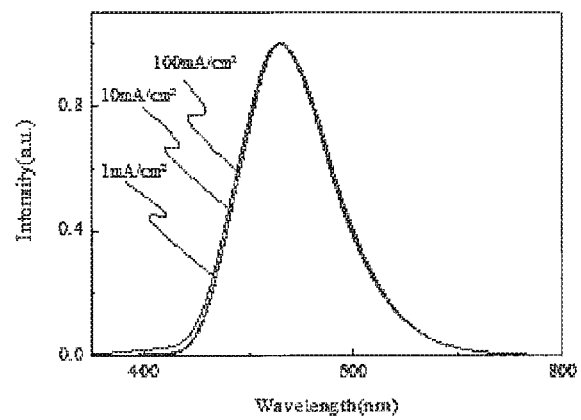
FIG. 47 is the light emission spectra of the organic electroluminescent device of the compound 13 in Example 20.
Figure 48:
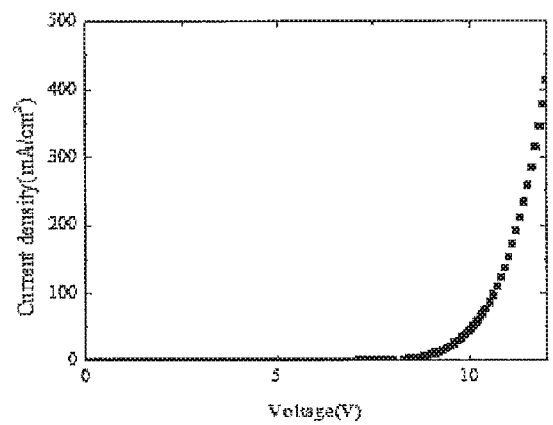
FIG. 48 is a graph showing the voltage-current density characteristics of the organic electroluminescent device of the compound 13 in Example 20.

FIG. 47 shows the light emission spectra of the organic electroluminescent device thus produced, FIG. 48 shows the voltage-current density characteristics thereof, and FIG. 40 referred above shows the current density-external quantum efficiency characteristics thereof. The organic electroluminescent device using the compound 13 as a light emitting material exhibited a high external quantum efficiency of 10.4%.

Example 21

Production and Evaluation of Organic Electroluminescent Device Using Compound 25

An organic electroluminescent device was produced in the same manner as in Example 17 except that the compound 25 was used instead of the compound 1.

Figure 49:
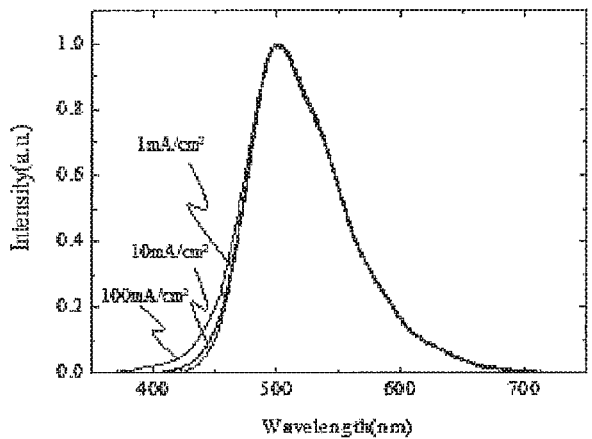
FIG. 49 is the light emission spectra of the organic electroluminescent device of the compound 25 in Example 21.
Figure 50:
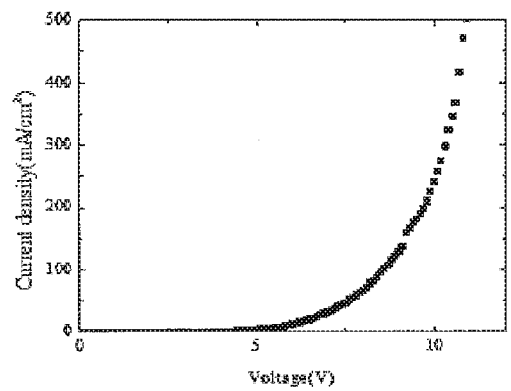
FIG. 50 is a graph showing the voltage-current density characteristics of the organic electroluminescent device of the compound 25 in Example 21.

FIG. 49 shows the light emission spectra of the organic electroluminescent device thus produced, FIG. 50 shows the voltage-current density characteristics thereof, and FIG. 40 referred above shows the current density-external quantum efficiency characteristics thereof. The organic electroluminescent device using the compound 25 as a light emitting material exhibited a high external quantum efficiency of 7.1%.

Example 22

Production and Evaluation of Organic Electroluminescent Device Using Compound 51

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, α-NPD was formed to a thickness of 35 nm on ITO, and mCBP was formed to a thickness of 10 nm thereon. Subsequently, the compound 51 and mCP were co-deposited thereon from separate vapor deposition sources to form a layer having a thickness of 30 nm, which was designated as a light emitting layer. At this time, the concentration of the compound 51 was 10.0% by weight. TPBi was then formed to a thickness of 25 nm, further lithium fluoride (LiF) was vacuum vapor-deposited to a thickness of 0.8 nm, and then aluminum (Al) was vapor-deposited to a thickness of 80 nm to form a cathode, thereby completing an organic electroluminescent device. Light emission of the organic electroluminescent device thus produced was confirmed.

Example 23

Production and Evaluation of Organic Electroluminescent Device Using Compound 55

An organic electroluminescent device was produced in the same manner as in Example 17 except that the compound 55 was used instead of the compound 1, provided that the concentration of the compound 55 in the light emitting layer was changed to 10.0% by weight, and the thickness of the light emitting layer was changed to 30 nm.

Figure 51:
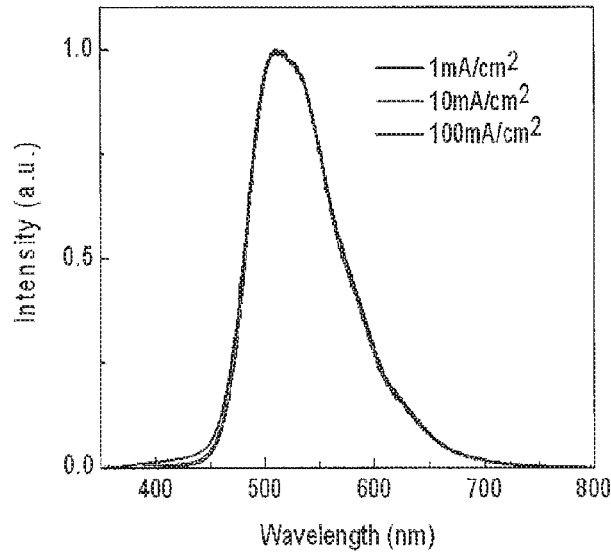
FIG. 51 is the light emission spectra of the organic electroluminescent device of the compound 55 in Example 23.
Figure 52:
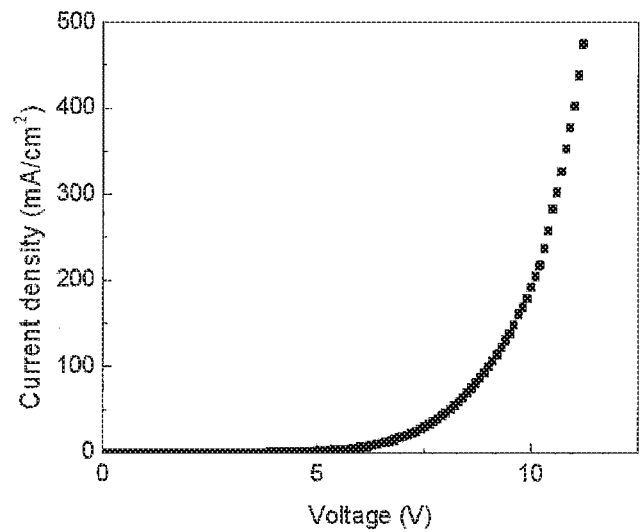
FIG. 52 is a graph showing the voltage-current density characteristics of the organic electroluminescent device of the compound 55 in Example 23.
Figure 53:
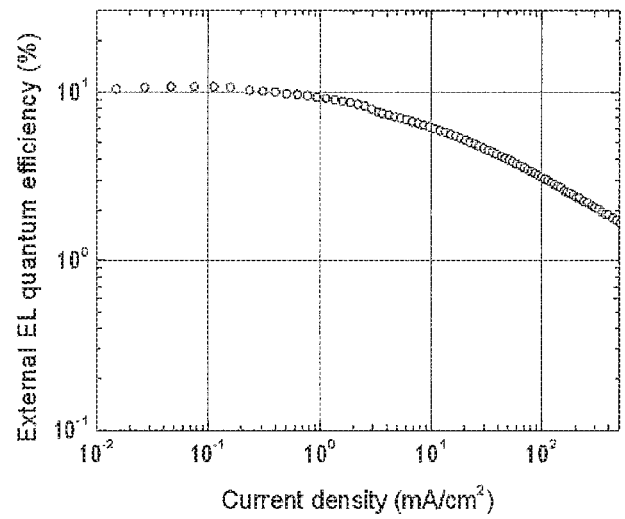
FIG. 53 is a graph showing the current density-external quantum efficiency characteristics of the organic electroluminescent device of the compound 55 in Example 23.

FIG. 51 shows the light emission spectra of the organic electroluminescent device thus produced, FIG. 52 shows the voltage-current density characteristics thereof, and FIG. 53 shows the current density-external quantum efficiency characteristics thereof. The organic electroluminescent device using the compound 55 as a light emitting material exhibited a high external quantum efficiency of 10.7%.

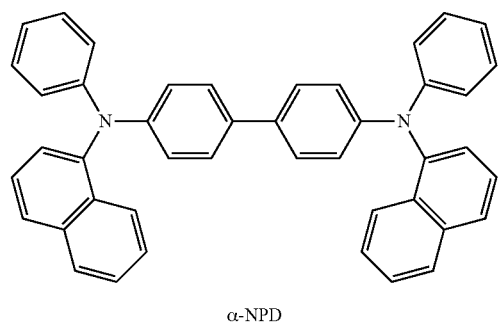

α-NPD

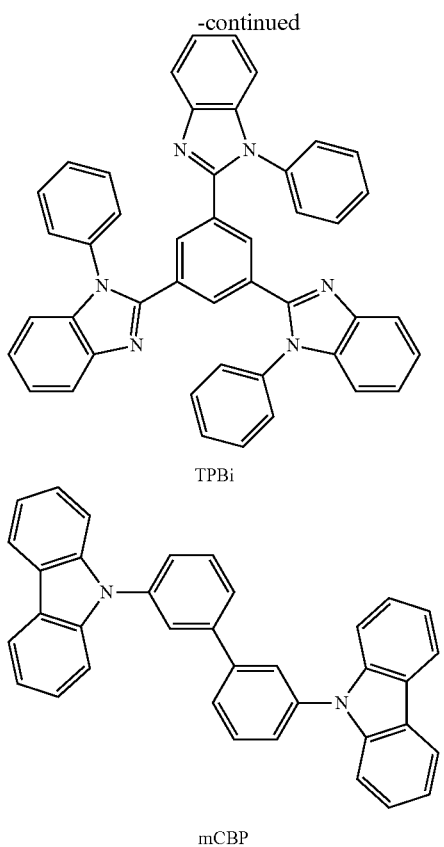

TPBi mCBP

INDUSTRIAL APPLICABILITY

The compound of the invention is useful as a light emitting material. Accordingly, the compound of the invention may be effectively used as a light emitting material of an organic light emitting device, such as an organic electroluminescent device. The compound of the invention includes a compound that emits delayed fluorescent light, and thus may be capable of providing an organic light emitting device having a high light emission efficiency. Thus, the invention has high industrial applicability.

REFERENCE SIGNS LIST 1 substrate
2 anode
3 hole injection layer
4 hole transporting layer
5 light emitting layer
6 electron transporting layer
7 cathode

The invention claimed is:

1. An organic metal complex represented by the following Formula (1):

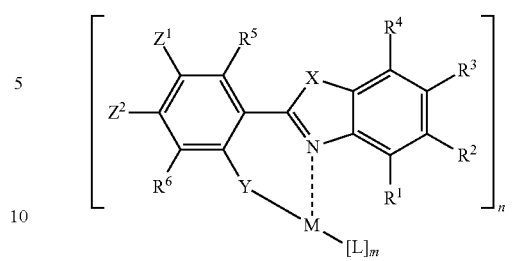

Formula (1)

wherein, in Formula (1), X represents an oxygen atom, a sulfur atom, or —N($R^7$)—; Y represents an oxygen atom, a sulfur atom, or —N(—$SO_2$—$R^8$)—; $R^1$ to $R^8$ each independently represent a hydrogen atom, an alkyl group which may be substituted by an alkoxy group, an aryl group or an aryloxy group, or an aryl group which may be substituted by an alkyl group, an alkoxy group, an aryl group or an aryloxy group; $Z^1$ and $Z^2$ each independently represent a hydrogen atom, an alkyl group which may be substituted by an alkoxy group, an aryl group or an aryloxy group, an aryl group which may be substituted by an alkyl group, an alkoxy group, an aryl group or an aryloxy group, or a group represented by any of the following Formulae (A) to (E), provided that at least one of $Z^1$ and $Z^2$ represents a group represented by any of the following Formulae (A) to (E); M represents lithium, sodium, potassium, rubidium, cesium, beryllium, magnesium, calcium, strontium, barium, copper, silver, gold, zinc, cadmium, mercury, boron, aluminum, gallium, indium, or thallium; L represents a ligand that is not encompassed by the following formula:

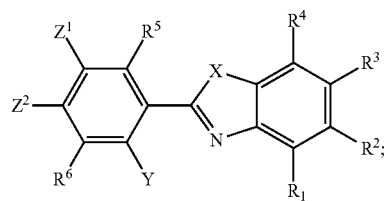

n represents an integer of from 1 to 3; and m represents an integer of from 0 to 2:

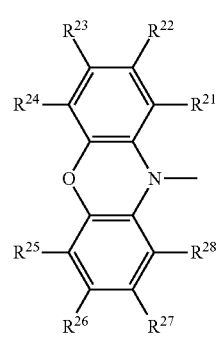

Formula (A)

-continued

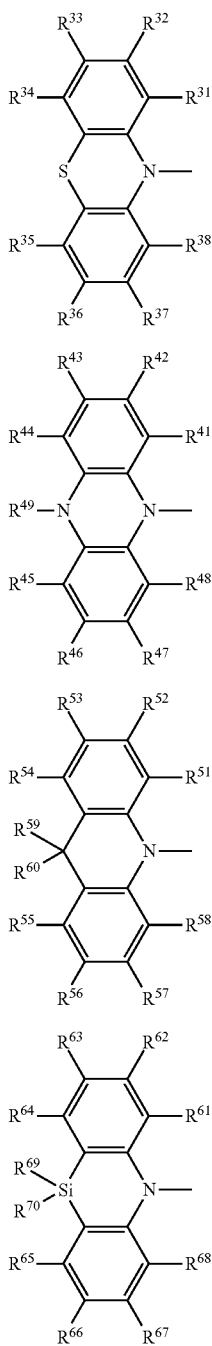

Formula (B)

Formula (C)

Formula (D)

Formula (E)

wherein, in Formulae (A) to (E), $R^{21}$ to $R^{28}$, $R^{31}$ to $R^{38}$, $R^{41}$ to $R^{49}$, and $R^{51}$ to $R^{70}$ each independently represent a hydrogen atom or a substituent, provided that $R^{21}$ and $R^{22}$, $R^{22}$ and $R^{23}$, $R^{23}$ and $R^{24}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$ $R^{51}$, and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{59}$ and $R^{60}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, and $R^{69}$ and $R^{70}$ each may be bonded to each other to form a cyclic structure.

2. The organic metal complex according to claim 1, wherein, in Formula (1), $Z^2$ represents a group represented by any of the Formulae (A) to (E).

3. The organic metal complex according to claim 1, wherein, in Formula (1), $Z^1$ represents a group represented by any of the Formulae (A) to (E).

4. The organic metal complex according to claim 1, wherein, in Formula (1), $Z^1$ or $Z^2$ represents a group represented by the Formula (A) or the Formula (B).

5. The organic metal complex according to claim 1, wherein, in Formula (1), M represents Zn or Li.

6. The organic metal complex according to claim 1, wherein, in Formula (1), Y represents an oxygen atom.

7. The organic metal complex according to claim 1, wherein, in Formula (1), m represents 1 or 2.

8. The organic metal complex according to claim 7, wherein L represents a substituted or unsubstituted aryloxy ligand.

9. The organic metal complex according to claim 8, wherein L represents an aryloxy ligand substituted with a substituted or unsubstituted diarylamino group.

10. A light emitting material comprising the organic metal complex according to claim 1.

11. A delayed fluorescent material comprising the organic metal complex according to claim 1.

12. An organic light emitting device comprising the light emitting material according to claim 10.

13. The organic light emitting device according to claim 12, wherein the organic light emitting device emits delayed fluorescent light.

14. The organic light emitting device according to claim 12, wherein the organic light emitting device is an organic electroluminescent device.

* * * * *